(12) United States Patent
Christel et al.

(10) Patent No.: US 6,369,893 B1
(45) Date of Patent: Apr. 9, 2002

(54) MULTI-CHANNEL OPTICAL DETECTION SYSTEM

(75) Inventors: Lee A. Christel, Palo Alto; M. Allen Northrup, Berkeley; Kurt E. Petersen, San Jose; William A. McMillan, Cupertino; Gregory T. A. Kovacs, Stanford; Steven J. Young, Los Gatos; Ronald Chang, Redwood City; Douglas B. Dority, Mill Valley; Raymond T. Hebert, Los Gatos; Gregory J. Kintz, Mountain View, all of CA (US)

(73) Assignee: Cepheid, Sunnyvale, CA (US)

( * ) Notice: Subject to any disclaimer, the term of this patent is extended or adjusted under 35 U.S.C. 154(b) by 0 days.

(21) Appl. No.: 09/314,605

(22) Filed: May 19, 1999

Related U.S. Application Data

(63) Continuation-in-part of application No. 09/081,260, filed on May 19, 1998, now abandoned, and a continuation-in-part of application No. 09/194,374, filed on Jul. 25, 2000.

(51) Int. Cl.[7] .............................................. G01N 21/64
(52) U.S. Cl. ................ 356/417; 250/458.1; 422/82.08; 436/172
(58) Field of Search .................. 356/317, 318, 356/417; 250/458.1, 459.1, 461.1, 461.2; 422/82.08, 82.07; 436/172

(56) References Cited

U.S. PATENT DOCUMENTS

| | | | |
|---|---|---|---|
| 3,708,886 A | | 1/1973 | Ogle ................................ 34/5 |
| 4,056,724 A | | 11/1977 | Harte .......................... 250/328 |
| 4,192,429 A | | 3/1980 | Yerman ....................... 215/307 |
| 4,432,644 A | * | 2/1984 | Demers et al. ............. 356/316 |
| 4,552,458 A | | 11/1985 | Lowne ........................ 356/446 |
| 4,580,059 A | * | 4/1986 | Wolfbeis et al. ......... 250/458.1 |

(List continued on next page.)

FOREIGN PATENT DOCUMENTS

| | | |
|---|---|---|
| EP | 0318255 | 5/1989 |
| EP | 1045038 | 10/2000 |
| WO | WO 97/41421 | 11/1997 |
| WO | WO 98/38487 | 9/1998 |

OTHER PUBLICATIONS

Wittwer, C.T. et al. The Light Cycler™: A Microvolume Multisample Fluorimeter with Rapid Temperature Control, *BioTechniques* 22:176–181; Jan. 1997.

*Primary Examiner*—F. L. Evans
(74) *Attorney, Agent, or Firm*—Heller Ehrman White & McAuliffe LLP

(57) ABSTRACT

An apparatus for thermally controlling and optically interrogating a reaction mixture includes a vessel [2] having a chamber [10] for holding the mixture. The apparatus also includes a heat-exchanging module [37] having a pair of opposing thermal plates [34A, 34B] for receiving the vessel [2] between them and for heating/and or cooling the mixture contained in the vessel. The module [37] also includes optical excitation and detection assemblies [46,48] positioned to optically interrogate the mixture. The excitation assembly [46] includes multiple light sources [100] and a set of filters for sequentially illuminating labeled analytes in the mixture with excitation beams in multiple excitation wavelength ranges. The detection assembly [48] includes multiple detectors [102] and a second set of filters for detecting light emitted from the chamber [10] in multiple emission wavelength ranges. The optics assemblies [46,48] thus provide a multi-channel system for detecting a plurality of different target analytes in the mixture.

54 Claims, 27 Drawing Sheets

U.S. PATENT DOCUMENTS

| | | | |
|---|---|---|---|
| 4,810,653 A | 3/1989 | Hefler et al. | 435/285.1 |
| 4,900,934 A | 2/1990 | Peeters et al. | 250/461.2 |
| 4,902,624 A | 2/1990 | Columbus et al. | 435/285.1 |
| 5,038,852 A | 8/1991 | Johnson et al. | 165/12 |
| 5,333,675 A | 8/1994 | Mullis et al. | 165/12 |
| 5,376,313 A | 12/1994 | Kanewske, III et al. | 264/1.1 |
| 5,422,726 A | 6/1995 | Tyler | 356/417 |
| 5,439,647 A | 8/1995 | Saini | 422/82.11 |
| 5,460,780 A | 10/1995 | Devaney, Jr. et al. | 422/99 |
| 5,475,610 A | 12/1995 | Atwood et al. | 364/500 |
| 5,543,026 A | 8/1996 | Hoff et al. | 204/612 |
| 5,580,794 A | 12/1996 | Ljungmann | 156/363 |
| 5,589,136 A | 12/1996 | Northrup et al. | 422/102 |
| 5,596,414 A | 1/1997 | Tyler | 356/417 |
| 5,656,493 A | 8/1997 | Mullis et al. | 435/286.1 |
| 5,675,155 A | 10/1997 | Pentoney, Jr. et al. | 250/458.1 |
| 5,721,136 A | 2/1998 | Finney et al. | 435/287.2 |
| 5,783,148 A | 7/1998 | Cottingham | 422/56 |
| 5,784,157 A * | 7/1998 | Gorfinkel et al. | 356/417 |
| 5,786,182 A | 7/1998 | Catanzariti et al. | 435/91.1 |
| 5,811,296 A | 9/1998 | Chemelli et al. | 435/287.2 |
| 5,863,790 A | 1/1999 | Bolea | 435/287.4 |
| 5,928,907 A | 7/1999 | Woudenberg et al. | 435/91.2 |
| 5,958,349 A | 9/1999 | Petersen et al. | 422/198 |
| 6,015,667 A | 1/2000 | Sharaf | 435/6 |
| 6,015,674 A | 1/2000 | Woudenberg et al. | 435/6 |
| 6,043,880 A | 3/2000 | Andrews et al. | 356/311 |
| 6,140,054 A | 10/2000 | Wittwer et al. | 435/6 |
| 6,144,448 A | 11/2000 | Mitoma | 356/317 |

* cited by examiner

FIG. 18

MULTI-CHANNEL OPTICAL DETECTION SYSTEM

RELATED APPLICATION INFORMATION

This application is a continuation-in-part of U.S. application Ser. No. 09/081,260 filed May 19, 1998, now abandoned, and U.S. application Ser. No. 09/194,374 filed Jul. 25, 2000. This application is also related to U.S. application Ser. No. 09/275,061 filed Mar. 23, 1999. All of these applications are incorporated by reference herein.

This invention was made with Government support under contract DAAM01-96-C-0061 awarded by the U.S. Army. The Government has certain rights in the invention.

TECHNICAL FIELD OF THE INVENTION

The present invention relates generally to optical detection systems, and in particular to a multi-channel detection system for the real-time detection of a plurality of different analytes in a fluid sample.

BACKGROUND OF THE INVENTION

There are many applications in the field of chemical processing in which it is desirable to precisely control the temperature of reaction mixtures (e.g., biological samples mixed with chemicals or reagents), to induce rapid temperature transitions in the mixtures, and to detect target analytes in the mixtures. Applications for such heat-exchanging chemical reactions may encompass organic, inorganic, biochemical and molecular reactions, and the like. Examples of thermal chemical reactions include nucleic acid amplification, thermal cycling amplification, such as polymerase chain reaction (PCR), ligase chain reaction (LCR), self-sustained sequence replication, enzyme kinetic studies, homogeneous ligand binding assays, and more complex biochemical mechanistic studies that require complex temperature changes.

A preferred detection technique for chemical or biochemical analysis is optical interrogation, typically using fluorescence or chemiluminescence measurements. For ligand-binding assays, time-resolved fluorescence, fluorescence polarization, or optical absorption are often used. For PCR assays, fluorescence chemistries are often employed.

Conventional instruments for conducting thermal reactions and for optically detecting the reaction products typically incorporate a block of metal having as many as ninety-six conical reaction tubes. The metal block is heated and cooled either by a Peltier heating/cooling apparatus or by a closed-loop liquid heating/cooling system in which liquid flows through channels machined into the block. Such instruments incorporating a metal block are described in U.S. Pat. No. 5,038,852 to Johnson, U.S. Pat. No. 5,333,675 to Mullis, and U.S. Pat. No. 5,475,610 to Atwood.

These conventional instruments have several disadvantages. First, due to the large thermal mass of a metal block, the heating and cooling rates in these instruments are limited to about 1° C./sec resulting in longer processing times. For example, in a typical PCR application, fifty cycles may require two or more hours to complete. With these relatively slow heating and cooling rates, it has been observed that some processes requiring precise temperature control are inefficient. For example, reactions may occur at the intermediate temperatures, creating unwanted and interfering side products, such as PCR "primer-dimers" or anomalous amplicons, which are detrimental to the analytical process. Poor control of temperature also results in over-consumption of reagents necessary for the intended reaction.

Another disadvantage of these conventional instruments is that they typically do not permit real-time optical detection or continuous optical monitoring of the chemical reaction. For example, in the Perkin Elmer 7700 (ATC) instrument, optical fluorescence detection is accomplished by guiding an optical fiber to each of ninety-six reaction sites in a metal block. A central high power laser sequentially excites each reaction site and captures the fluorescence signal through the optical fiber. Since all of the reaction sites are sequentially excited by a single laser and since the fluorescence is detected by a single spectrometer and photomultiplier tube, simultaneous monitoring of each reaction site is not possible.

Some of the instrumentation for newer processes requiring real-time optical monitoring of a chemical reaction has only recently become available. One such instrument is the MATCI device disclosed by Northrup et al in U.S. Pat. No. 5,589,136. This device uses a modular approach to PCR thermal cycling and optical analysis. Each chemical reaction is performed in its own silicon sleeve and each sleeve has its own associated optical excitation source and fluorescence detector. Using a light-emitting diode (LED) and a solid-state detector, real-time optical data is obtained from a compact, low-power module. The device includes only one light source and one detector for each module, however, so that the simultaneous detection of multiple analytes is not possible.

Another analysis instrument is available from Idaho Technologies and described by Wittwer et al. in *"The LightCycler™: A Microvolume Multisample Fluorimeter with Rapid Temperature Control"*, BioTechniques, Vol. 22, pgs. 176–181, January 1997. The instrument includes a circular carousel with a stepper motor for holding up to twenty-four samples and for sequentially positioning each of the samples over an optics assembly. The temperature of the samples is controlled by a central heating cartridge and a fan positioned in a central chamber of the carousel.

In operation, the samples are placed in capillaries which are held by the carousel, and each sample is interrogated through a capillary tip by epi-illumination. The light source is a blue LED that is reflected off a first dichroic filter towards the sample. Light is focused to and collected from the capillary tip by an epi-illumination lens. Light emitted from the capillary tip passes through the first dichroic filter, is filtered by one or more additional dichroic filters, and is focused to photodiodes for detection.

Although this instrument permits detection of multiple analytes in a sample undergoing chemical reaction, it has several disadvantages. First, the illumination beams and the emitted light beams have relatively short optical path lengths through the sample volume and share the same path below the capillary tip. This may cause fluorescent emissions from the sample to be weak, leading to poor optical detection sensitivity. Second, the instrument only provides illumination light in one excitation wavelength range. Different fluorescent dyes have different optimal excitation wavelength ranges, however, so that the instrument cannot provide excitation beams in the optimal excitation wavelength range for each of multiple fluorescent dyes in the reaction fluid. Third, the use of dichroic filters may significantly decrease the optical sensitivity of the instrument. Each dichroic filter decreases the intensity of the emitted light by about half, so that the emitted light beams may be weak by the time they reach the detectors. For these reasons, the instrument may exhibit poor sensitivity in detecting fluorescently labeled analytes in the samples.

U.S. Pat. No. 5,675,155 issued to Pentoney et al. discloses another detection system for sequentially and repetitively scanning a plurality of sample volumes and for detecting radiation emitting from each of the samples. The system includes a plurality of coplanar side-by-side capillaries each containing a sample volume. The system also includes an electromagnetic radiation source, a mirror aligned to receive and reflect electromagnetic radiation, a scanner for moving the mirror, a filter wheel for filtering electromagnetic radiation collected from the samples, and a detector aligned to receive the filtered radiation. The sample volume in each capillary column contains fluorescently-labeled samples separated on an electrophoretic medium.

In operation, the radiation source, preferably a laser, directs an excitation beam onto the mirror. The reflected excitation beam passes through a focusing lens and onto a sample volume of a first capillary within the capillary array. Fluorescence emission radiation from the sample is collected and passed through a first filter of the filter wheel which is selected to block light at the wavelength of the laser source and to transmit fluorescence emitted by a first fluorescent dye in the sample volume. Fluorescence transmitted through the first filter is then detected by the detector. A motor then rotates the filter wheel to bring a second filter into the fluorescence emission beam. The second filter transmits fluorescence emitted by a second fluorescence dye, and the fluorescence is measured by the detector. The same process is repeated with third and fourth filters of the filter wheel to measure the fluorescent emission of third and fourth dyes in the sample volume. The entire four-step operation is then performed sequentially and repeatedly with each capillary column in the array.

Although this system permits the detection of multiple fluorescent dyes in a sample volume, it has several disadvantages in its use of a moving mirror and a rotating filter wheel. These moving parts typically result in a high cost of the optical system, high maintenance requirements, low reliability, high power consumption, and potential vibratory interference with the optical measurements.

SUMMARY

The present invention overcomes the disadvantages of the prior art by providing an improved system for thermally controlling and optically interrogating reaction mixtures (e.g., biological samples mixed with chemicals or reagents). In contrast to the prior art devices described above, the system of the present invention provides excitation light to each mixture in multiple, distinct excitation wavelength ranges. This ensures that the optimal excitation wavelength range is provided for each of a plurality of analytes in the mixture having different fluorescent, phosphorescent, chemiluminescent, or electrochemiluminescent labels. In addition, the system permits the simultaneous, real-time detection of multiple analytes in the mixture without requiring any moving parts, e.g., carousels or optical filter wheels. Because it has no moving parts, the system of the present invention typically has a lower cost, lower maintenance requirements, higher reliability, and lower power consumption than the prior art devices described above.

The system of the present invention also overcomes the disadvantages of the prior art by providing for extremely rapid and accurate temperature changes of the reaction mixtures. Such tight control of temperature inhibits side reactions, such as the formation of unwanted bubbles or the degradation of components at certain temperatures, that would otherwise interfere with optical detection and analysis. The system is therefore useful in thermally sensitive chemical processes, such as polymerase chain reaction (PCR), ligase chain reaction (LCR), self-sustained sequence replication, enzyme kinetic studies, homogeneous ligand binding assays, and more complex biochemical mechanistic studies that require complex temperature changes.

In a preferred embodiment, the invention provides a system for independently thermally controlling and optically interrogating a plurality of reaction mixtures. The system includes a plurality of reaction vessels, each of the vessels having a reaction chamber for holding one of the mixtures. Each of the vessels also includes first and second optically transmissive walls defining a portion of its chamber. The optically transmissive walls are angularly offset from each other to allow optical excitation of the mixture through the first wall and optical detection of labeled analytes through the second wall.

The system also includes a corresponding plurality of heat-exchanging modules for receiving the vessels. Each module includes a pair of opposing thermal plates positioned to receive one of the vessels between them. At least one of the plates, and preferably both of the plates, has a heating element coupled thereto for heating the reaction mixture contained in the vessel. Each module also includes first and second optics assemblies positioned such that when the vessel is placed between the plates, the first and second optics assemblies are in optical communication with the first and second optically transmissive walls of the vessel, respectively.

The first optics assembly includes a first housing having a first optical window, and at least two light sources for transmitting excitation beams to the reaction mixture through the first window. The first optics assembly also includes a first set of filters for filtering the excitation beams such that each of the beams transmitted to the reaction mixture has a substantially distinct excitation wavelength range. In operation, the light sources are sequentially activated to excite different fluorescent, phosphorescent, chemiluminescent, or electrochemiluminescent labels in the reaction mixture. The light sources and the first set of filters are rigidly fixed in the first housing.

The second optics assembly includes a second housing having a second optical window for receiving light emitted from the vessel. The second optics assembly also includes at least two detectors, preferably photodiodes, for detecting the emitted light and a second set of filters for separating the emitted light into at least two emission wavelength ranges and for directing the emitted light in each of the emission wavelength ranges to a respective one of the detectors. The detectors and the second set of filters are rigidly fixed in the second housing.

In the preferred embodiment, the first optics assembly of each module includes at least four light sources arranged with the first set of filters for transmitting the excitation beams in at least four excitation wavelength ranges, and the second optics assembly of each module includes at least four detectors arranged with the second set of filters for detecting emitted light in at least four emission wavelength ranges. The system thus includes at least four separate optical channels for detecting up to four different analytes in each reaction mixture. Also in the preferred embodiment, the system includes a base instrument for receiving the heat-exchanging modules. The base instrument includes processing electronics for independently controlling the operation of each module. The system also preferably includes a computer programmed to control the processing electronics in the base instrument.

Although it is presently preferred to position all of the light sources. in the first optics assembly and all of the detectors in the second optics assembly, it is also possible to include both one or more light sources and one or more detectors in each of the optics assemblies. According to a second embodiment of the invention, the first optics assembly comprises a first housing having a first optical window. The first optics assembly also includes a first light source for transmitting a first excitation beam to the reaction mixture through the first window and a first detector for receiving light emitted from the chamber through the first window. The first optics assembly further includes a first set of filters arranged in the first housing for filtering portions of the first excitation beam outside of a first excitation wavelength range, for filtering portions of the emitted light outside of a first emission wavelength range, and for directing the emitted light in the first emission wavelength range to the first detector. The first light source, the first set of filters, and the first detector are rigidly fixed in the first housing.

Also according to the second embodiment, the second optics assembly comprises a second housing having a second optical window. The second optics assembly also includes a second light source for transmitting a second excitation beam to the reaction mixture through the second window and a second detector for receiving light emitted from the chamber through the second window. The second optics assembly further includes a second set of filters arranged in the second housing for filtering portions of the second excitation beam outside of a second excitation wavelength range different than the first excitation wavelength range, for filtering portions of the emitted light outside of a second emission wavelength range different than the first emission wavelength range, and for directing the emitted light in the second emission wavelength range to the second detector. The second light source, the second set of filters, and the second detector are rigidly fixed in the second housing, so that the optical system has no moving parts. In the second embodiment, each optics assembly may optionally include an additional detector and filter to provide four optical detection channels for detecting up to four different analytes in each reaction mixture.

A more complete understanding of the system of the present invention may be gained upon consideration of the following description and accompanying drawings.

BRIEF DESCRIPTION OF THE DRAWINGS

FIGS. 5A–D are a series of intensity vs. wavelength graphs in which:

FIGS. 5A and 5B show the excitation and emission spectra, respectively, of four dyes typically used in thermal reactions.

FIG. 5C shows the effects of filtering the outputs of green and blue LEDs to provide distinct excitation wavelength ranges; and FIG. 5D shows the effects of filtering light emitted from each of the four dyes to form distinct emission wavelength ranges.

FIGS. 16–18 are a series of sample graphic displays viewable on the user's computer monitor according to the present invention.

FIG. 16 illustrates a Program Menu Screen through which site profiles are created and executed.

FIG. 17 illustrates an Instrument Menu Screen that displays current thermal cycling status.

FIG. 18 illustrates a Library Menu Screen through which desired temperature profiles may be retrieved from memory and executed and through which results may be displayed, transmitted to another computer, and/or printed.

DETAILED DESCRIPTION

The present invention provides a system for thermally controlling and optically interrogating a reaction mixture, e.g., a fluid sample mixed with chemicals or reagents. As used herein, the term "fluid sample" includes both gases and liquids, preferably the latter. The sample may be an aqueous solution containing particles, cells, microorganisms, ions, or small and large molecules, such as proteins and nucleic acids, etc. In a particular use, the sample may be a bodily fluid, e.g., blood or urine, or a suspension, such as pulverized food.

In a preferred embodiment, the system includes reaction vessels for holding the mixtures and heat-exchanging modules for receiving the vessels. Each heat-exchanging module includes a pair of opposing thermal plates between which one of the vessels is inserted for thermal processing, a fan positioned adjacent the plates for cooling the mixture, one or more temperature sensors for measuring the temperature of the plates, and a pair of optics assemblies for optically interrogating the mixture. The system also includes a base unit with processing electronics for receiving the heat-exchanging modules and for independently controlling each module. The system further includes a controller, such as a personal computer or network computer, that provides a user interface and controls the operation of the processing electronics.

Figure 1:
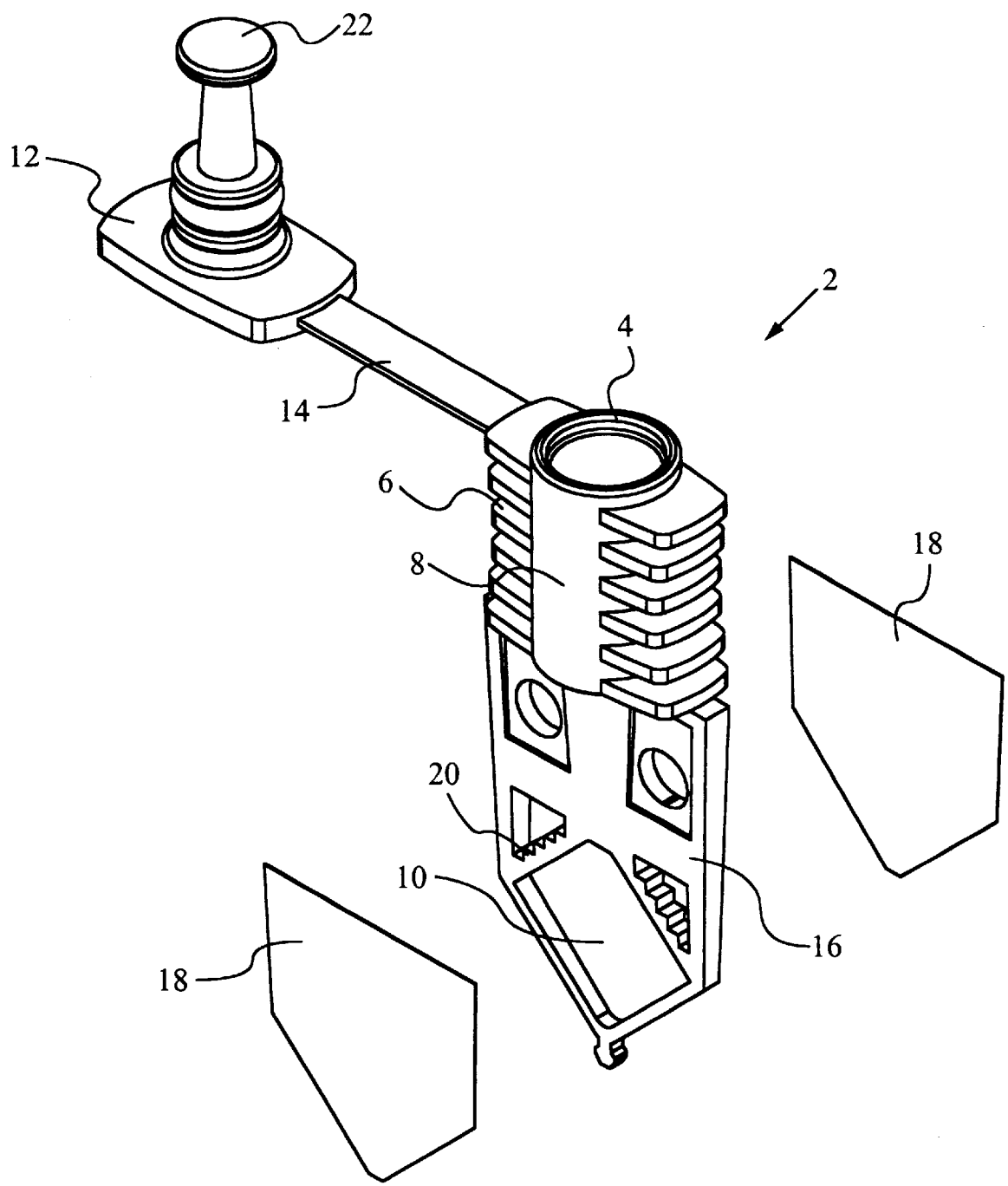
FIG. 1 shows a partially exploded, perspective view of a reaction vessel according to the present invention in which the reaction chamber sidewalls are removed to show the interior of the chamber.
Figure 2:
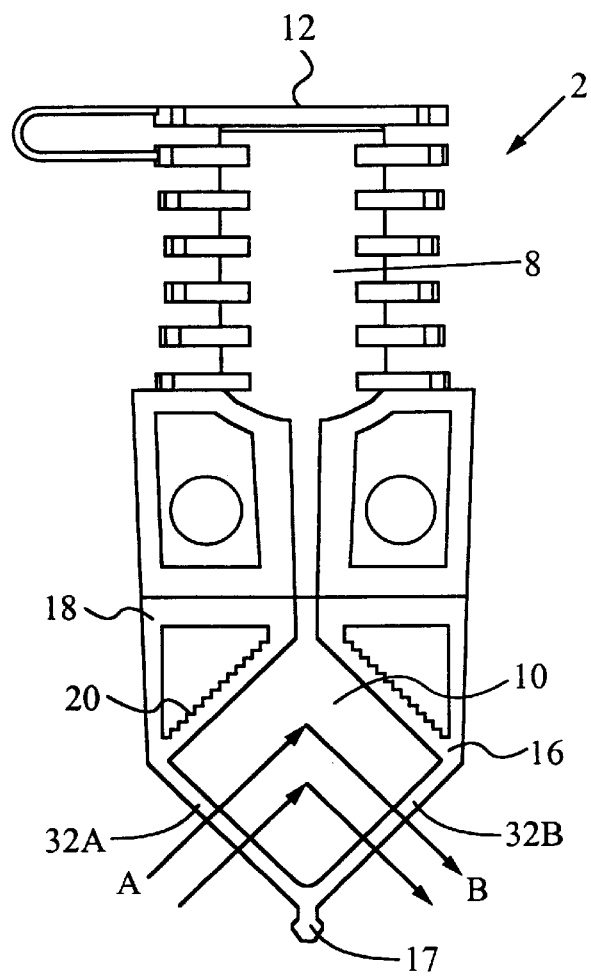
FIG. 2 is a front view of the vessel of FIG. 1.

FIGS. 1–22 illustrate a preferred embodiment of the invention. FIG. 1 shows a partially exploded view of a reaction vessel 2, and FIG. 2 shows a front view of the vessel 2. The vessel 2 includes a reaction chamber 10 for holding a reaction mixture. The vessel 2 is designed for optimal heat transfer to and from the reaction mixture and for efficient optical viewing of the mixture. The thin shape of the vessel contributes to optimal thermal kinetics by providing large surfaces for thermal conduction and for contacting thermal plates. In addition, the walls of the vessel 2 provide optical windows into the chamber 10 so that the entire reaction mixture can be optically interrogated.

In more detail to FIGS. 1–2, the reaction vessel 2 includes a rigid frame 16 that defines the perimeter of the reaction chamber 10. The frame 16 also includes a port 4 and a channel 8 that connects the port 4 to the reaction chamber 10. Thin, flexible walls 18 (shown in FIG. 1 exploded from the frame 16) are coupled to opposite sides of the frame 16 to form the sidewalls of the chamber 10.

The walls 18 facilitate optimal thermal conductance to the reaction mixture contained in the chamber 10. The flexible nature of the walls 18 allows for maximum contact with thermal plates. The walls are conformable to the surface of the plates to prevent or minimize gaps between surfaces. Furthermore, the flexible walls continue to conform to the thermal surface if the surface shape changes during the course of the heat-exchanging operation.

Figure 3:
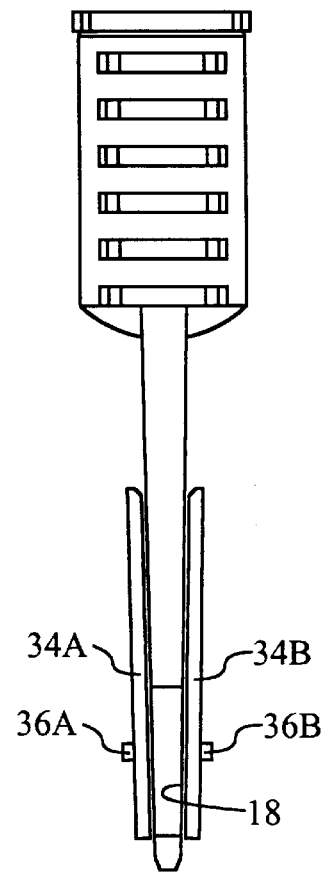
FIG. 3 is a side view of the vessel of FIG. 1 inserted in a thermal sleeve formed by opposing thermal plates.

FIG. 3 shows contact between the reaction vessel and a pair of opposing thermal plates 34A, 34B. At least one of the plates, and preferably both of the plates, includes a heating element, such as a resistor, for heating the reaction mixture in the vessel. The plates 34A, 34B also preferably include temperature sensors, such as thermistors 36A, 36B. When the vessel 2 is inserted between the plates, the inner surfaces of the plates contact walls 18. In this position, minimal or no gaps are found between the plate surfaces and the walls 18 of the reaction chamber. For good thermal conductance, the thickness of each wall 18 is preferably between about 0.003 to 0.5 mm, more preferably 0.01 to 0.15 mm, and most preferably 0.025 to 0.08 mm. Each wall 18 may be a film, sheet, or a molded, machined extruded or cast piece, or other convenient thin and flexible structure.

The material composing the walls 18 may be a polyalcohol including polypropylene, polyethylene, polyester, and other polymers, laminates or homogenous polymers, metals or metal laminates, or other materials which may be thin, flexible, conformable and permit high heat transfer and is preferably in the form of a film or sheet. Where the frame 16 of the vessel is a particular material, such as polypropylene, the sidewalls are preferably the same material, such as polypropylene, so that the heat expansion and cooling rates of the walls are substantially the same as the frame.

The thermal plates 34A, 34B may be made of various materials including ceramics or metals such as aluminum nitride, aluminum oxide, beryllium oxide, and silicon nitride. Other materials which may be utilized include, e.g., gallium arsenide, silicon, silicon nitride, silicon dioxide, quartz, glass, diamond, polyacrylics, polyamides, polycarbonates, polyesters, polyimides, vinyl polymers, and halogenated vinyl polymers, such as polytetrafluoroethylenes. Other possible materials include thermocouple materials such as chrome/aluminum, superalloys, zircaloy, aluminum, steel, gold, silver, copper, tungsten, molybdenum, tantalum, brass, sapphire, or any of the numerous ceramics, metals, and synthetic polymeric materials available in the art.

Ceramic plates are presently preferred because their inside surfaces may be conveniently machined to very high smoothness for high wear resistance, high chemical resistance, and good thermal contact to reaction vessels. Ceramic plates can also be made very thin, e.g., between 0.635 and 1.25 mm, for low thermal mass to provide for extremely rapid temperature changes. A heat exchanging plate made from aluminum or copper also has high thermal conduction, but a larger thermal mass.

The heating elements (preferably resistors) coupled to the plates 34A, 34B may be directly screen printed onto the plates, particularly plates comprising ceramic materials, such as aluminum nitride and aluminum oxide. Screen-printing provides high reliability and low cross-section for efficient transfer of heat into the reaction chamber. The heating element may also be baked inside of the ceramic plate. Also, thick or thin film resistors of varying geometric patterns may be disposed on the plate walls to provide more uniform heating, for example by having denser resistors at the extremities and thinner resistors in the middle. Heating elements may comprise metals, tungsten, polysilicon, or other materials that heat when a voltage is applied to the material. The thermal plates may also be heated using a laminated heater source such as an etched-foil heating element (Minco Products, located in Minneapolis, Minn.) attached to the surface of the plates.

Referring again to FIGS. 1–2, the reaction vessel 2 also preferably includes a seal cap 12. The cap 12 may be conveniently attached to the frame 16 by a flexible arm 14. The cap 12 includes a piston or plug 22 that is inserted into the channel 8 when the cap 12 is placed on the vessel 2. When inserted into the channel 8, the piston 22 pressurizes the chamber 10, thereby expanding the flexible walls 18. The expansion of the walls 18 provides for increased conformity between the walls 18 and the surfaces of the thermal plates.

In using the reaction vessel 2, a sample is added to the reaction chamber 10 through the port 4. This may be accomplished by inserting a pipette tip through the channel 8 into the interior of the chamber 10 and filling the chamber 10 from the bottom up. Alternatively, the sample may be added through automated fluid injection, or through a fluidic manifold which optionally is an integral part of the reaction vessel. For manual addition of the sample, the vessel 2 preferably includes finger grips 6.

The sample may be mixed with reagents and fluorescent dyes prior to being added to the chamber 10. Alternatively, the sample may be introduced to reagents and dyes in the chamber 10. As shown in FIG. 3, the vessel 2 is placed between the thermal plates 34A, 34B so that the walls 18 of the vessel press against and conform to the inner surfaces of the plates. The reaction mixture is exposed to variations in temperature by activating the heating elements on the plates 34A, 34B. The reaction mixture is then optically interrogated, preferably through the optically transmissive bottom walls 32A, 32B of the frame 16, as shown in FIG. 2. Arrows A in FIG. 2 represent illumination beams entering the chamber 10 through wall 32A and arrows B represent emitted light exiting the chamber 10 through wall 32B.

The walls 32A, 32B are angularly offset from each other to allow optical excitation of labeled analytes in the reaction mixture through the first wall 32A and optical detection of the labeled analytes through the second wall 32B. It is usually preferred that the walls 32A, 32B are offset at an angle of about 90°. A 90° angle between excitation and detection paths assures that a minimum amount of excitation radiation entering through wall 32A will exit through wall 32B. Also the 90° angle permits a maximum amount of emitted radiation, e.g. fluorescence, to be collected through wall 32B. In alternative embodiments, the angle between the optical walls may be larger or smaller than 90°, depending upon the efficiency and sensitivity of the excitation and detection optics. For example, where a detection system effectively discriminates between excitation and emitted light, an angle of less than 90° between walls may be desired. Conversely, where a detection system fails to efficiently discriminate between excitation and emitted light, an angle greater than 90° may be of interest.

The walls 32A, 32B may be joined to form a "V" shaped point at the bottom of the chamber 10. Alternatively, the interface of the angled walls need not connect to form a point, but may be separated by an intermediary portion, such as another wall or various mechanical or fluidic features which do not interfere with the thermal and optical performance of the vessel. For example, the angled walls may meet at a port which leads to another processing area in communication with the chamber 10, such as an integrated capillary electrophoresis area. In the presently preferred embodiment, a locating tab 17 extends below the intersection of walls 32A, 32B. The locating tab 17 is used to properly position the vessel 2 in a heat-exchanging module described below with reference to FIG. 4.

Optimum optical sensitivity may be attained by maximizing the optical sampling path length of both the light beams exciting the labeled analytes in the reaction mixture and the emitted light that is detected, as represented by the equation:

$$I_o/I_i = C \cdot L \cdot A,$$

where $I_o$ is the illumination output of the emitted light in volts, photons or the like, C is the concentration of analyte to be detected, $I_i$ is the input illumination, L is the path length, and A is the intrinsic absorptivity of the dye used to label the analyte.

The thin, flat reaction vessel 2 of the present invention optimizes detection sensitivity by providing maximum optical path length per unit analyte volume. In particular, the vessel 2 is preferably constructed such that each of the sides of the chamber 10 has a length in the range of 1 to 15 mm, the chamber has a thickness in the range of 0.5 to 5 mm, and the ratio of the length of each side of the chamber to the thickness of the chamber is at least 2:1. These parameters are presently preferred to provide a vessel having a relatively large optical path length through the chamber, i.e. 1 to 15 mm on average, while still keeping the chamber sufficiently thin to allow for extremely rapid heating and cooling of the reaction mixture contained in the chamber.

More preferably, the vessel 2 is constructed such that each of the sides of the chamber 10 has a length in the range of 5 to 12 mm, the chamber has a thickness in the range of 0.5 to 2 mm, and the ratio of the length of each side of the chamber to the thickness of the chamber is at least 5:1. These ranges are more preferable because they provide a vessel having both a large optical path length (i.e., 5 to 12 mm on average) and a large volume capacity (in the range of 12 to 100 microliters) while still maintaining a chamber sufficiently thin to permit extremely rapid heating and cooling of a reaction mixture. The large volume capacity provides for increased sensitivity in the detection of low concentration analytes, such as nucleic acids.

In the presently preferred embodiment, the reaction vessel 2 has a diamond-shaped chamber having sides of length 10 mm, a thickness of 1 mm, and a volume capacity of 100 microliters. This reaction vessel provides a relatively large optical path length of 10 mm through the chamber 10. Additionally, the thin chamber allows for extremely rapid heating and/or cooling of the reaction mixture contained therein.

The frame 16 is made of an optically transmissive material, e.g., a polycarbonate or polypropylene. As shown in FIG. 2, the portion of the frame forming the top of the chamber 10 also preferably includes reflective faces 20 which bounce back light trying to exit through the top of the chamber 10, allowing for increased detection of signal. In addition, one or more optical elements may be present on the optically transmissive walls 32A, 32B. The optical elements may be designed, for example, to maximize the total volume of solution which is illuminated by a light source, to focus excitation light on a specific region of the chamber 10, or to collect as much fluorescence signal from as large a fraction of the chamber volume as possible. The optical elements may comprise gratings for selecting specific wavelengths, filters for allowing only certain wavelengths to pass, or colored lenses to provide filtering functions. The wall surfaces may be coated or comprise materials such as liquid crystal for augmenting the absorption of certain wavelengths. In the presently preferred embodiment, the optically transmissive walls 32A, 32B are simply clear, flat windows.

The reaction vessel 2 may be fabricated by first molding the rigid frame 16 to form a chamber having open sides. The frame 16 is preferably made by standard injection molding processes. After the frame is made, the sidewalls 18 are produced by placing and preferably stretching material, e.g., thin films or sheets of polypropylene, over the chamber area. The walls 18 are then attached to opposite sides of the frame 16. Where the walls are a film or sheet, the walls may be attached to the frame by heat-sealing, adhesive bonding, ultrasonic bonding, etc.

Figure 4:
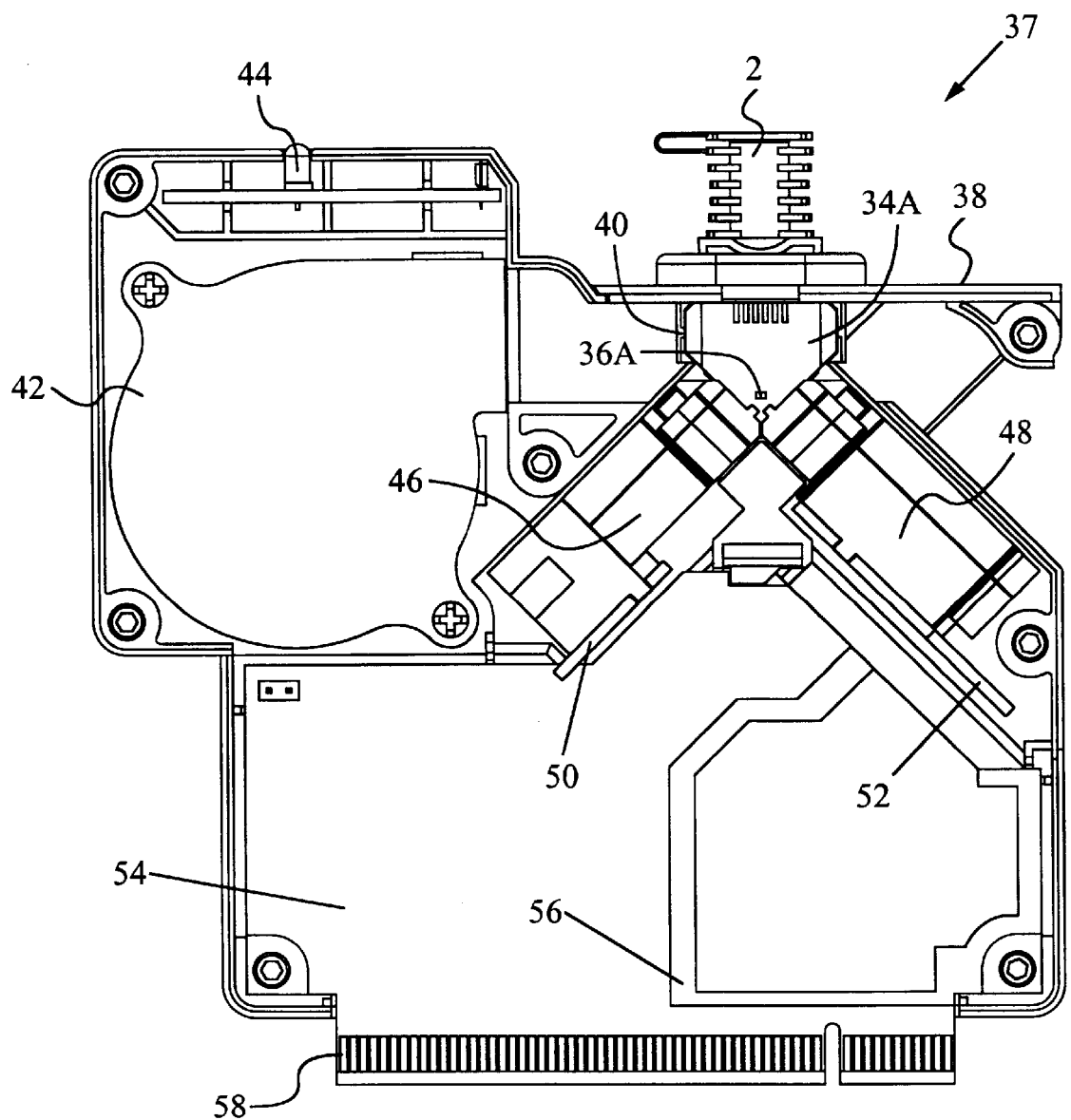
FIG. 4 is a side view of a heat-exchanging module according to the present invention having a thermal sleeve, a pair of optics assemblies, and a cooling system. The reaction vessel of FIG. 1 is inserted into the thermal sleeve.

FIG. 4 shows a heat-exchanging module 37 for receiving the reaction vessel 2. The heat-exchanging module 37 preferably includes a housing 38 for holding the various components of the module. The module 37 also includes the thermal plates 34A, 34B described above (only plate 34A visible in the view of FIG. 4). The plates may be held in an opposing relationship to each other by brackets, supports, or retainers 40. Additionally, the plates may be spring-biased towards each other as described in U.S. application Ser. No. 09/194,374 filed Nov. 24, 1998, the disclosure of which is incorporated by reference herein. The housing 38 includes a slot above the plates 34A, 34B so that the vessel 2 may be inserted through the slot and between the plates.

The heat-exchanging module 37 also preferably includes a cooling system, such as a fan 42, for cooling the reaction mixture in the vessel 2. When the vessel 2 is positioned between the plates 34A, 34B, the chamber of the vessel is cooled by the air circulating from the fan 42. Alternatively, the cooling system may comprise a Peltier device or other refrigeration system for carrying a refrigerant or compressed fluid past the reaction vessel. These and other cooling systems are well known in the art.

The heat-exchanging module 37 further includes an optical excitation assembly 46 and an optical detection assembly 48 for optically interrogating the reaction mixture contained in the vessel 2. The excitation assembly 46 includes a first circuit board 50 for holding its electronic components, and the detection assembly 46 includes a second circuit board 52 for holding its electronic components. The excitation assembly 46 includes multiple light sources, such as LEDs, for exciting fluorescently-labeled analytes in the vessel 2. The excitation assembly 46 also includes one or more lenses for collimating the light from the light sources, as well as filters for selecting the excitation wavelength ranges of interest. The detection assembly 48 includes multiple detectors, such as photodiodes, for monitoring the light emitted from the vessel 2. The detection assembly 48 also includes one or more lenses for focusing and collimating the emitted light, as well as filters for selecting the emission wavelength ranges of interest. The specific components of the optics assemblies 46, 48.are described in greater detail below with reference to FIGS. 6–9.

The optics assemblies 46, 48 are positioned in the housing 38 such that when the vessel 2 is placed between the plates 34A, 34B, the first optics assembly 46 is in optical communication with the first optically transmissive bottom wall 32A of the vessel and the second optics assembly 48 is in optical communication with the second optically transmissive bottom wall 32B of the vessel (see FIG. 2). In the preferred embodiment, the optics assemblies 46, 48 are placed in optical communication with the bottom walls of the vessel 2 by simply locating the optics assemblies next to the thermal plates 34A, 34B so that when the vessel is placed between the plates, the optics assemblies 46, 48 are physically adjacent the first and second bottom walls of the vessel, respectively.

Additionally, the longitudinal axes of the optics assemblies 46, 48 are preferably angularly offset from each other by an angle of about 90°, and the assemblies 46, 48 are preferably positioned such that when the vessel 2 is placed between the plates, the longitudinal axis of the optics assembly 46 is orthogonal to the first bottom wall and the longitudinal axis of the optics assembly 48 is orthogonal to the second bottom wall. A 90° angle between excitation and detection paths assures that a minimum amount of excitation radiation entering through the first bottom wall of the vessel exits through the second bottom wall. Also the 90° angle permits a maximum amount of emitted radiation to be collected through the second wall.

Optionally, a gel or fluid may be used to establish or improve optical communication between each optics assembly and the vessel 2. The gel or fluid should have a refractive index close to the refractive indexes of the elements that it is coupling. In alternative embodiments, optical communication may be established between the optics assemblies and the walls of the vessel via optical fibers; light pipes, wave guides, or similar devices. One advantage of these devices is that they eliminate the need to locate the optics assemblies 46, 48 physically adjacent to the thermal plates 34A, 34B. This leaves more room around the plates in which to circulate cooling air or refrigerant, so that cooling may be improved.

In the preferred embodiment, the vessel 2 includes a locating tab 17 (see FIG. 2) that fits into a slot formed between the optics assemblies 46,48 to ensure proper positioning of the vessel 2 for optical detection. For improved detection, the module 37 also preferably includes a light-tight lid (not shown) that is placed over the top of the vessel 2 and sealed to the housing 38 after the vessel is inserted between the plates 34A, 34B.

The housing 38 may be molded from a rigid, high-performance plastic, or other conventional material. The primary functions of the housing 38 are to provide a frame for holding the plates 34A, 34B and optics assemblies 46, 48 and to provide flow channels and ports for directing cooling fluid, e.g. air or freon, and efficiently guiding the fluid flow across the surface of the plates 34A, 34B and reaction vessel 2.

The heat-exchanging module 37 also includes a PC board 54 for holding the electronic components of the module and an edge connector 58 for connecting the module 37 to a base instrument, as will be described below with reference to FIG. 10. The heating elements and thermistors 36A, 36B on the plates 34A, 34B, as well as the optical boards 50 and 52, are connected to the PC board 54 by flex cables (not shown in FIG. 4 for clarity of illustration). The module 37 may also include a grounding trace 56 for shielding the optical detection circuit. The module 37 also preferably includes an indicator, such as an LED 44, for indicating to a user the current status of the module such as "ready to load sample", "ready to load reagent," "heating," "cooling," "finished," or "fault".

Figure 5A:
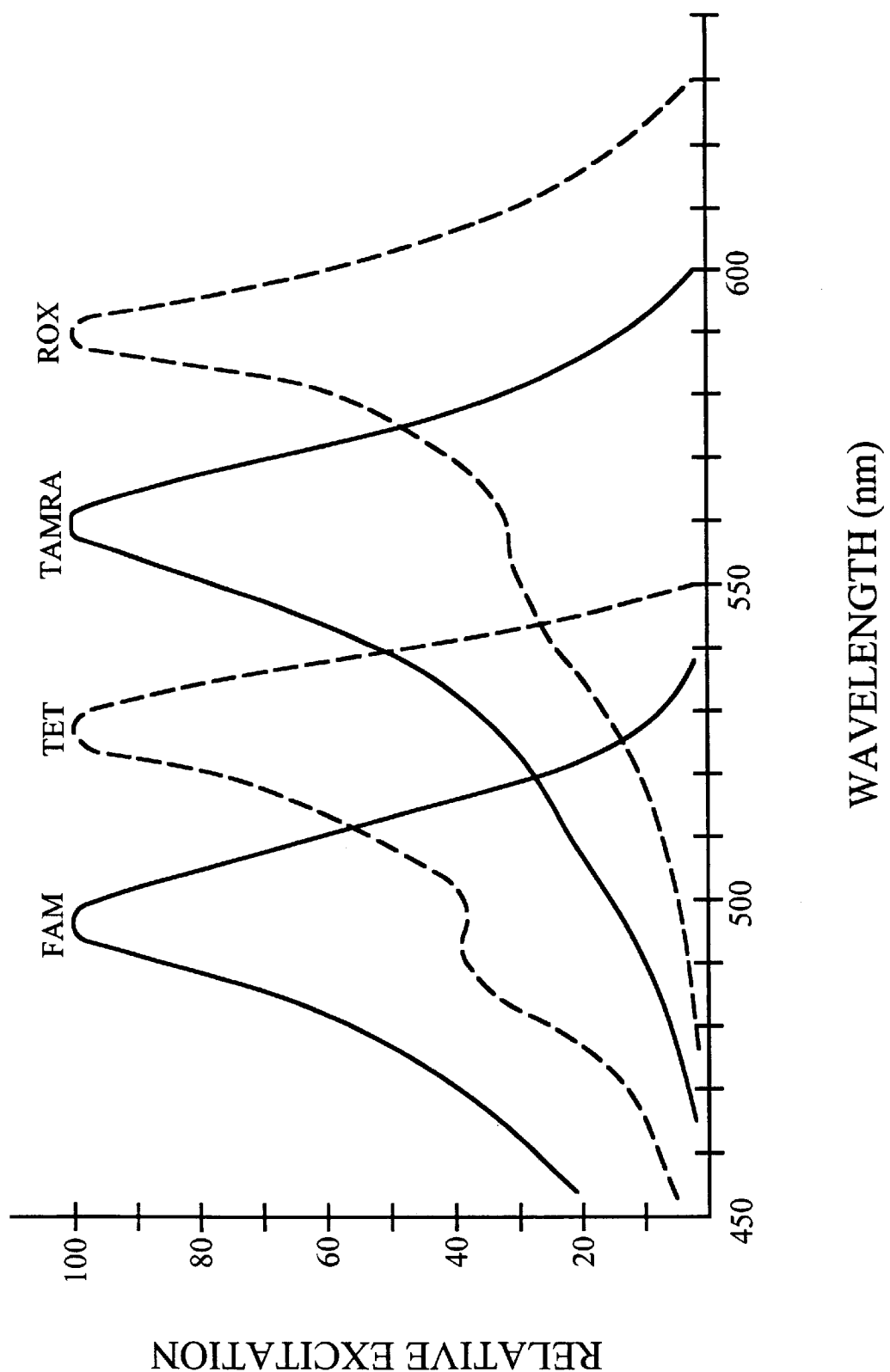
Figure 5B:
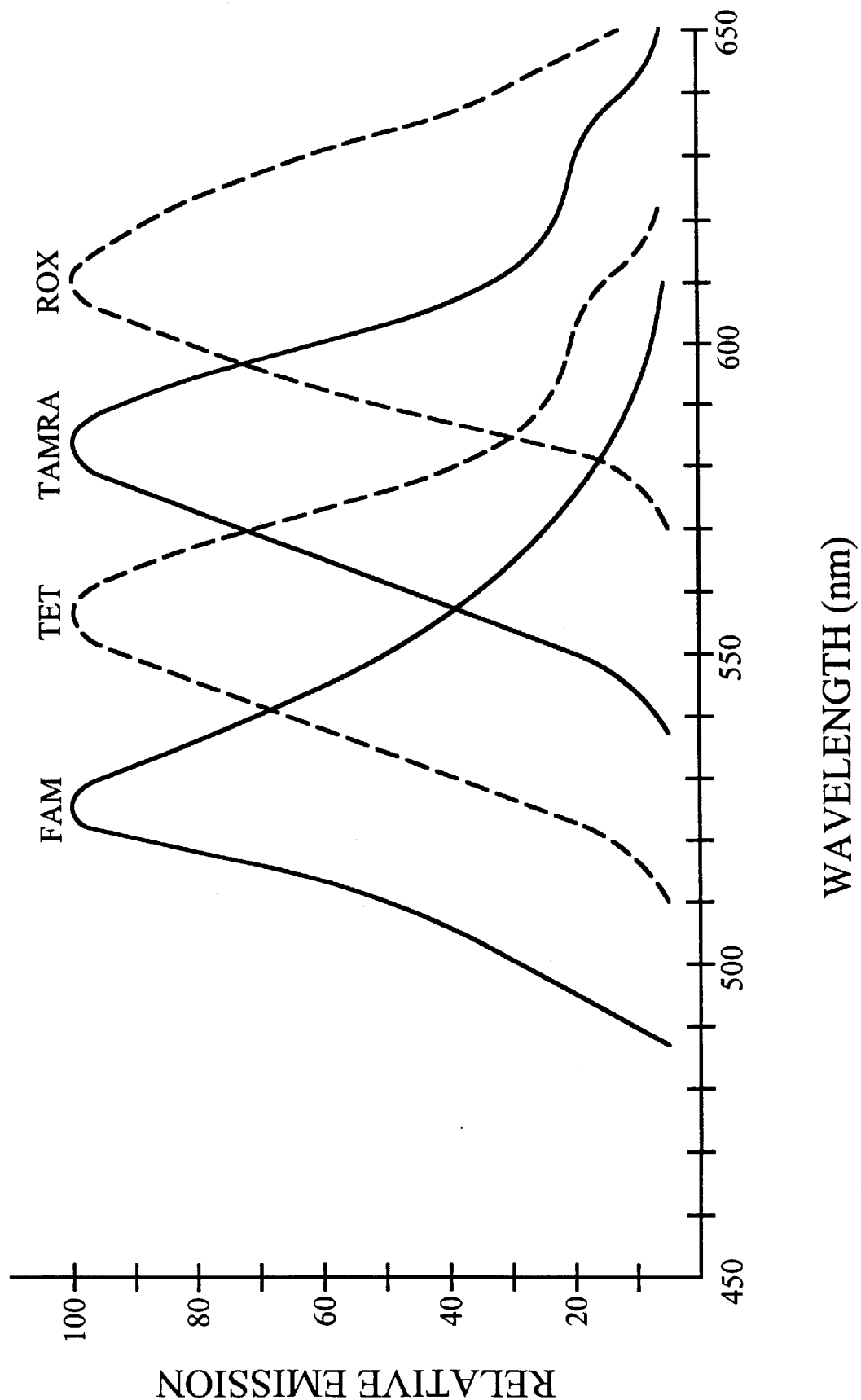

FIGS. 5A and 5B show the fluorescent excitation and emission spectra, respectively, of four fluorescent dyes of interest. These dyes are standard fluorescent dyes used with the TaqMan® chemistry (available from the Perkin-Elmer Corporation, Foster City, Calif.) and are well known by their acronyms FAM, TET, TAMRA, and ROX. Although the preferred embodiment is described with reference to these four dyes, it is to be understood that the system of the present invention are not limited to these particular dyes or to the TaqMan® chemistry. The system may be used with any fluorophores including, but not limited to, fluorescent dyes used with the Beacons chemistry, dyes used with the Sunrise® chemistry, and interculating dyes such as ethidium bromide. Fluorescent dyes and labeling chemistries for labeling analytes in a reaction mixture are well known in the art and need not be discussed further herein. Further, although fluorescence detection is presently preferred, the detection system of the present invention is not limited to detection based upon fluorescent labels. The system may be applicable to detection based upon phosphorescent labels, chemiluminescent labels, or electrochemiluminescent labels.

As shown in FIG. 5A, the excitation spectra curves for FAM, TET, TAMRA, and ROX are typically very broad at the base, but sharper at the peaks. As shown in FIG. 5B, the relative emission spectra curves for the same dyes are also very broad at the base and sharper at the peaks. One serious problem is that these dyes have strongly overlapping characteristics in both their excitation and emission spectra. The overlapping characteristics have traditionally made it difficult to distinguish the fluorescent signal of one dye from another when multiple dyes are used to label different analytes in a reaction mixture.

Figure 5C:
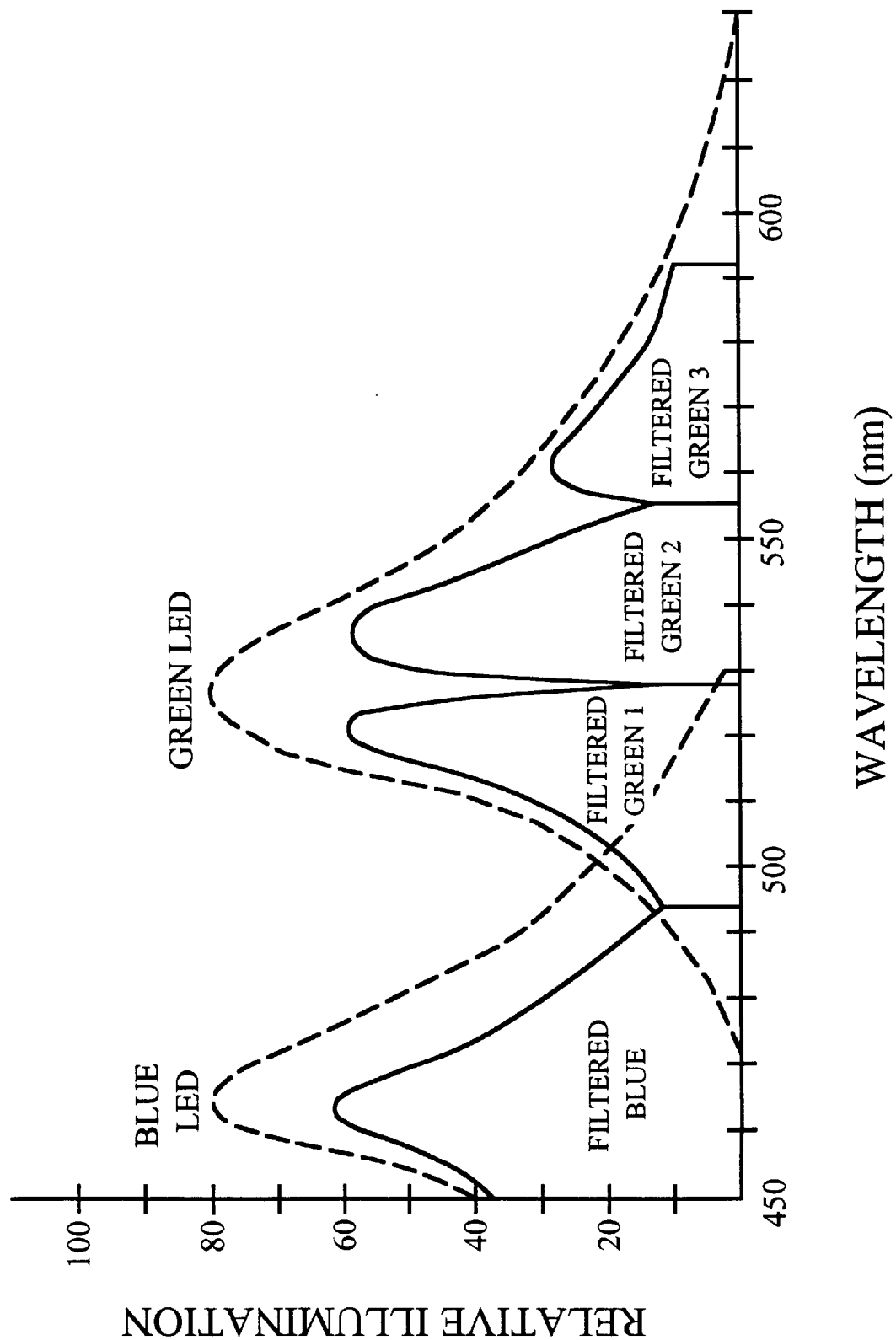

According to the present invention, multiple light sources are used to provide excitation beams to the dyes in multiple excitation wavelength ranges. Each light source provides excitation light in a wavelength range matched to the peak excitation range of a respective one of the dyes. In the preferred embodiment, the light sources are blue and green LEDs. FIG. 5C shows the effects of filtering the outputs of blue and green LEDs to provide substantially distinct excitation wavelength ranges. Typical blue and green LEDs have substantial overlap in the range of around 480 nm through 530 nm. By the filtering regime of the present invention, the blue LED light is filtered to a range of about 450 to 495 nm to match the relative excitation peak for FAM. The green LED light is filtered to a first range of 495 to 527 nm corresponding to the excitation peak for TET, a second range of 527 to 555 nm, corresponding to the excitation peak for TAMRA, and a third range of 555 to 593 nm corresponding to the excitation peak for ROX.

Figure 5D:
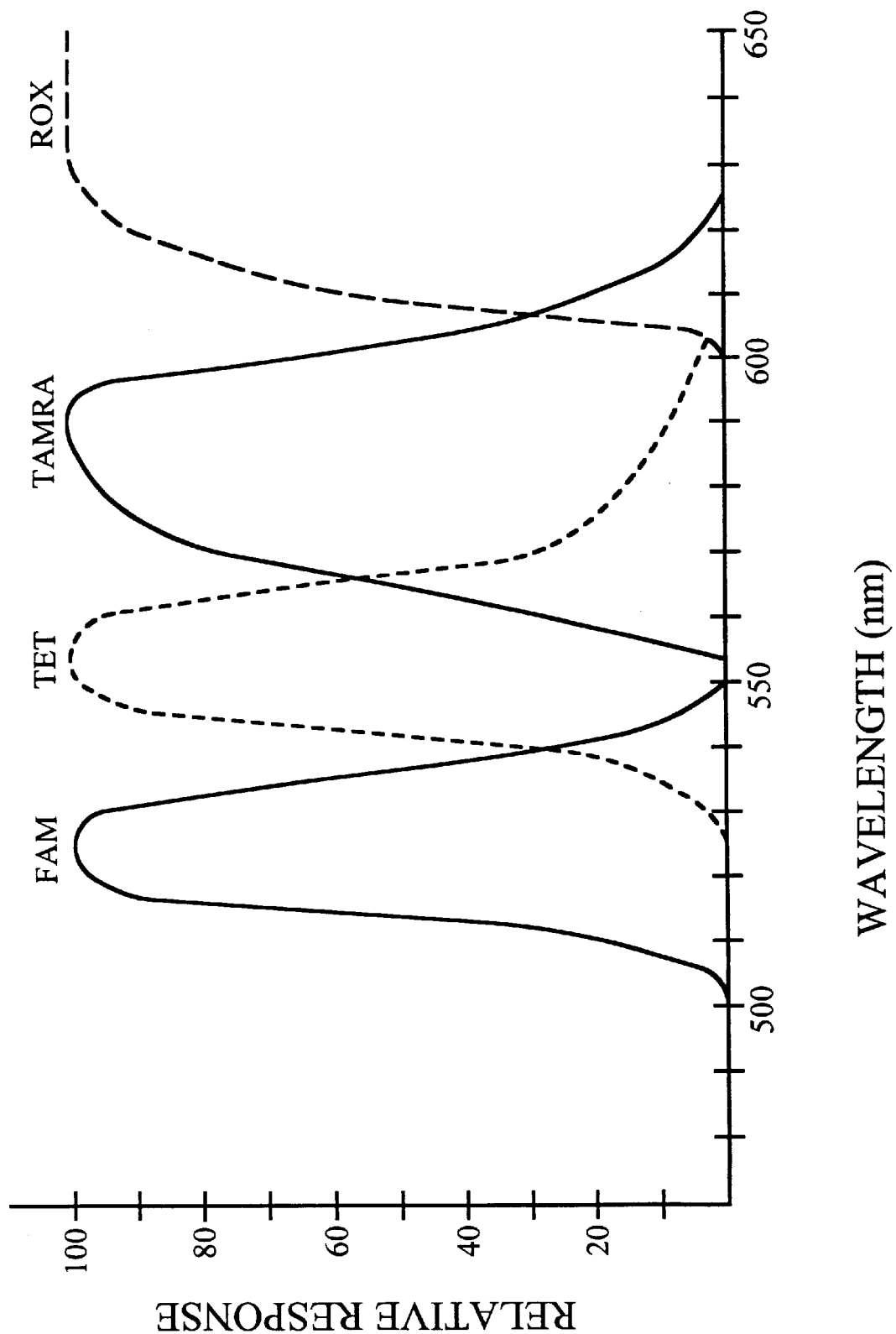

FIG. 5D shows the effects of filtering light emitted (fluorescent output) from each of the four dyes to form distinct emission wavelength ranges. As shown previously in FIG. 5B, the fluorescent emissions of the dyes before filtering are spherically diffuse with overlapping spectral bandwidths, making it extremely difficult to distinguish the fluorescent output of one dye from another. As shown in FIG. 5D, by filtering the fluorescent outputs of the dyes into substantially distinct wavelength ranges, a series of relatively narrow peaks (detection windows) are obtained, making it possible to distinguish the fluorescent outputs of different dyes, thus enabling the detection of a number of different fluorescently-labeled analytes in a reaction mixture.

Figure 6:
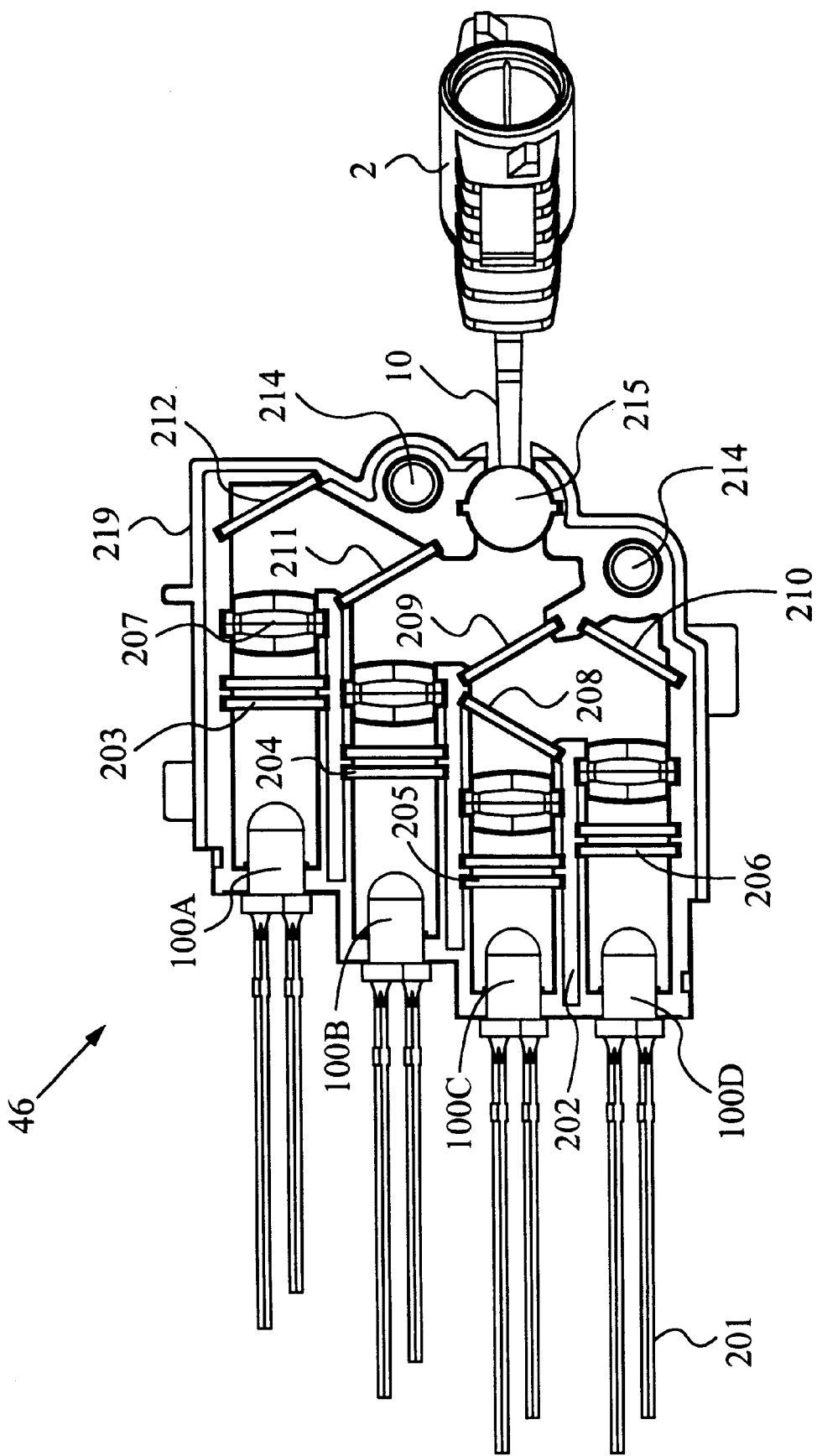
FIG. 6 is a schematic, plan view of an optical excitation assembly of the module of FIG. 4.
Figure 7:
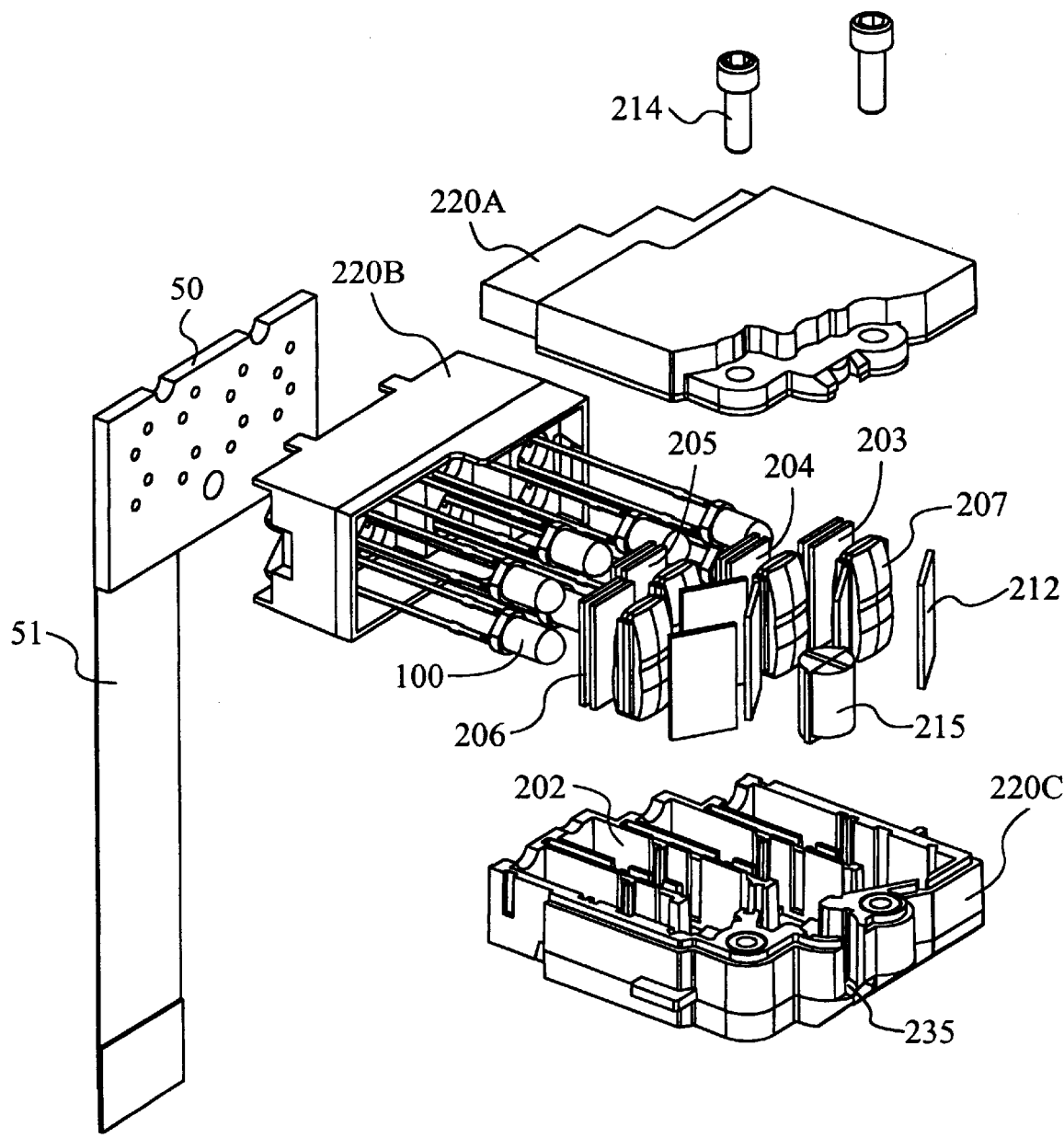
FIG. 7 is an exploded view of the excitation assembly of FIG. 6.

FIG. 6 is a schematic, plan view of the optical excitation assembly 46 of the heat-exchanging module. The assembly 46 is positioned adjacent the reaction vessel 2 to transmit excitation beams to the reaction mixture contained in the chamber 10. FIG. 7 is an exploded view of the excitation assembly 46. As shown in FIGS. 6–7, the assembly 46 includes a housing 219 for holding various components of the assembly. Housing 219 preferably comprises one or more molded pieces of plastic. In the preferred embodiment, the housing 219 is a multi-part housing comprised of three housing elements 220A, 220B, and 220C. The upper and lower housing elements 220A and 220C are preferably complementary pieces that couple together and snap-fit into housing element 220B. In this embodiment, the housing elements 220A and 220C are held together by screws 214. In alternative embodiments, the entire housing 219 may be a one-piece housing that holds a slide-in optics package.

The lower housing element 220C includes an optical window 235 into which is placed a cylindrical rod lens 215 for focusing excitation beams into the chamber 10. In general, the optical window 235 may simply comprise an opening in the housing through which excitation beams may be transmitted to the chamber 10. The optical window may optionally include an optically transmissive or transparent piece of glass or plastic serving as a window pane, or as in the preferred embodiment, a lens for focusing excitation beams.

The optics assembly 46 also includes four light sources, preferably LEDs 100A, 100B, 100C, and 100D, for transmitting excitation beams through the window 235 to the reaction mixture contained in the chamber 10. In general, each light source may comprise a laser, a light bulb, or an LED. In the preferred embodiment, each light source comprises a pair of directional LEDs. In particular, the four light sources shown in FIGS. 6–7 are preferably a first pair of green LEDs 100A, a second pair of green LEDs 100B, a pair of blue LEDs 100C, and a third pair of green LEDs 100D. The LEDs receive power through leads 201 which are connected to a power source (not shown in FIGS. 6–7). The LEDs are mounted to the optical circuit board 50 which is attached to the back of the housing element 220B so that the LEDs are rigidly fixed in the housing. The optical circuit board 50 is connected to the main PC board of the heat-exchanging module (shown in FIG. 4) via the flex cable 51.

The optics assembly 46 further includes a set of filters and lenses arranged in the housing 219 for filtering the excitation beams generated by the LEDs so that each of the beams transmitted to the chamber 10 has a distinct excitation wavelength range. As shown in FIG. 7, the lower housing element 220C preferably includes walls 202 that create separate excitation channels in the housing to reduce potential cross-talk between the different pairs of LEDs. The walls 202 preferably include slots for receiving and rigidly holding the filters and lenses. The filters and lenses may also be rigidly fixed in the housing by means of an adhesive used alone, or more preferably, with an adhesive used in combination with slots in the housing.

In general, the filters in the optics assembly 46 may be selected to provide excitation beams to the reaction mixture in the chamber 10 in any desired excitation wavelength ranges. The optics assembly 46 may therefore be used with any fluorescent, phosphorescent, chemiluminescent, or electrochemiluminescent labels of interest. For purposes of illustration, one specific embodiment of the assembly 46 will now be described in which the assembly is designed to provide excitation beams corresponding to the peak excitation wavelength ranges FAM, TAMRA, TET, and ROX.

In this embodiment, a pair of 593 nm low pass filters 203 are positioned in front of green LEDs 100A, a pair of 555 nm, low pass filters 204 are positioned in front of green LEDs 100B, a pair of 495 nm low pass filters 205 are positioned in front of blue LEDs 100C, and a pair of 527 nm low pass filters 206 are positioned in front of green LEDs 100D. Although it is presently preferred to position a pair of low pass filters in front of each pair of LEDs for double filtering of excitation beams, a single filter may be used in alternative embodiments. In addition, a lens 207 is preferably positioned in front of each pair of filters for collimating the filtered excitation beams. The optics assembly 46 also includes a 495 nm high pass reflector 208, a 527 nm high pass reflector 209, a mirror 210, a 555 nm, low pass reflector 211, and a 593 nm low pass reflector 212. The reflecting filters and mirrors 208–212 are angularly offset by 30° from the low pass filters 203–206.

The excitation assembly 46 transmits excitation beams to the chamber 10 in four distinct excitation wavelength ranges as follows. When the green LEDs 100A are activated, they generate an excitation beam that passes through the pair of 593 nm low pass filters 203 and through the lens 207. The excitation beam then reflects off of the 593 nm low pass reflector 212, passes through the 555 nm, low pass reflector 211, reflects off of the 527 nm high pass reflector 209, and passes through the lens 215 into the reaction chamber 10. The excitation beam from the LEDs 100A is thus filtered to a wavelength range of 555 to 593 nm corresponding to the peak excitation range for ROX.

When the green LEDs 100B are activated, they generate an excitation beam that passes through the pair of 555 nm, low pass filters 204, reflects off of the 555 nm, low pass reflector 211, reflects off of the 527 nm high pass reflector 209, and passes through the lens 215 into the reaction chamber 10. The excitation beam from LEDs 100B is thus filtered to a wavelength range of 527 to 555 nm, corresponding to the peak excitation range for TAMRA.

When the blue LEDs 100C are activated, they generate an excitation beam that passes through the pair of 495 nm low pass filters 205, through the 495 nm high pass reflector 208, through the 527 nm high pass reflector 209, and through the lens 215 into the reaction chamber 10. The excitation beam from LEDs 100C is thus filtered to a wavelength below 495 nm corresponding to the peak excitation range for FAM.

When the green LEDs 100D are activated, they generate an excitation beam that passes through the pair of 527 nm low pass filters 206, reflects off of the mirror 210, reflects off of the 495 nm high pass reflector 208, passes through the 527 nm high pass reflector 209, and passes through the lens 215 into the reaction chamber 10. The excitation beam from LEDs 100D is thus filtered to a wavelength range of 495 to 527 nm corresponding to the peak excitation range for TET. In operation, the LEDs 100A, 100B, 100C, 100D are sequentially activated to excite the different fluorescent dyes contained in the chamber 10 with excitation beams in substantially distinct wavelength ranges, as will be described in greater detail below.

Figure 8:
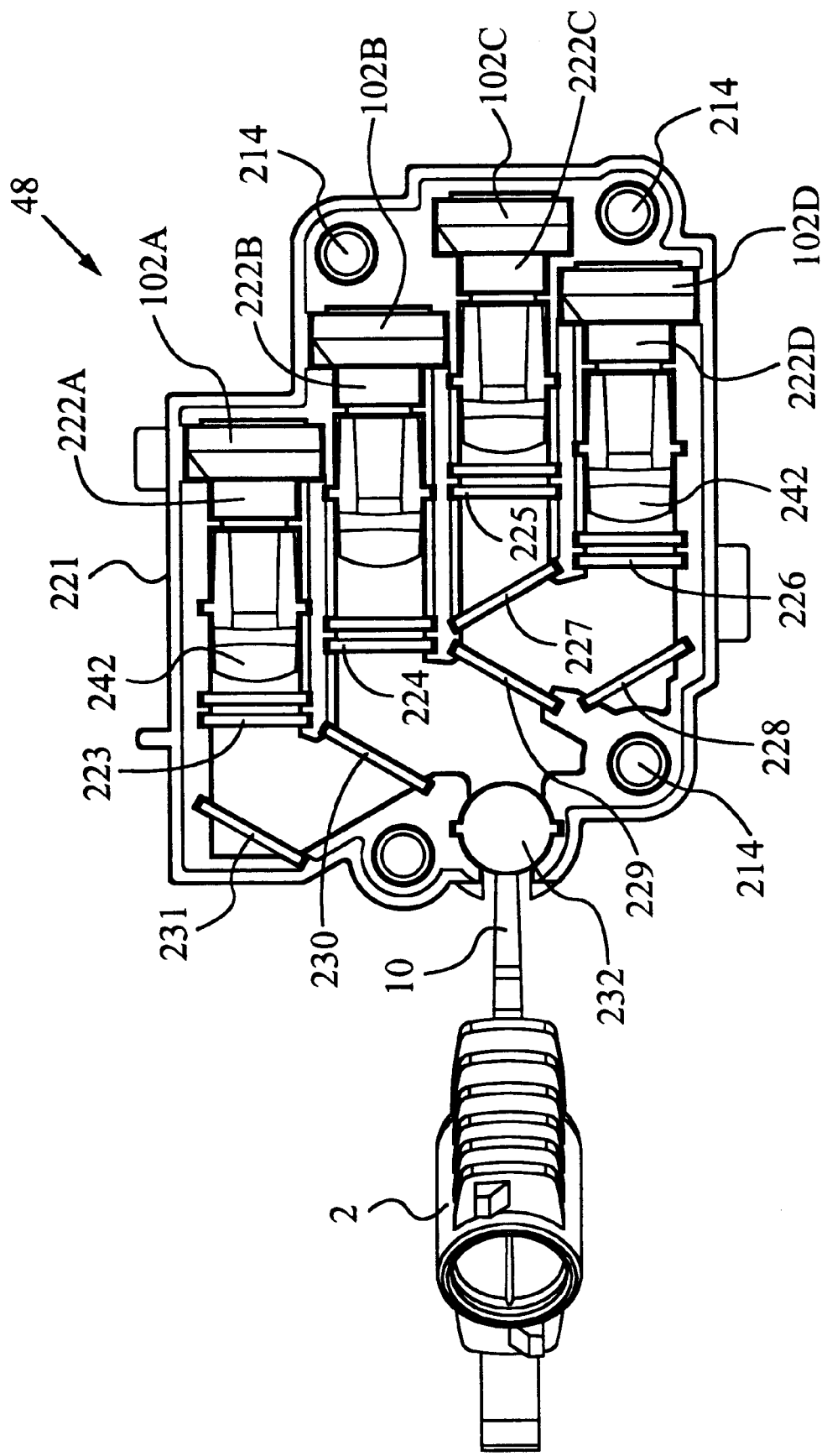
FIG. 8 is a schematic, plan view of an optical detection assembly of the module of FIG. 4.
Figure 9:
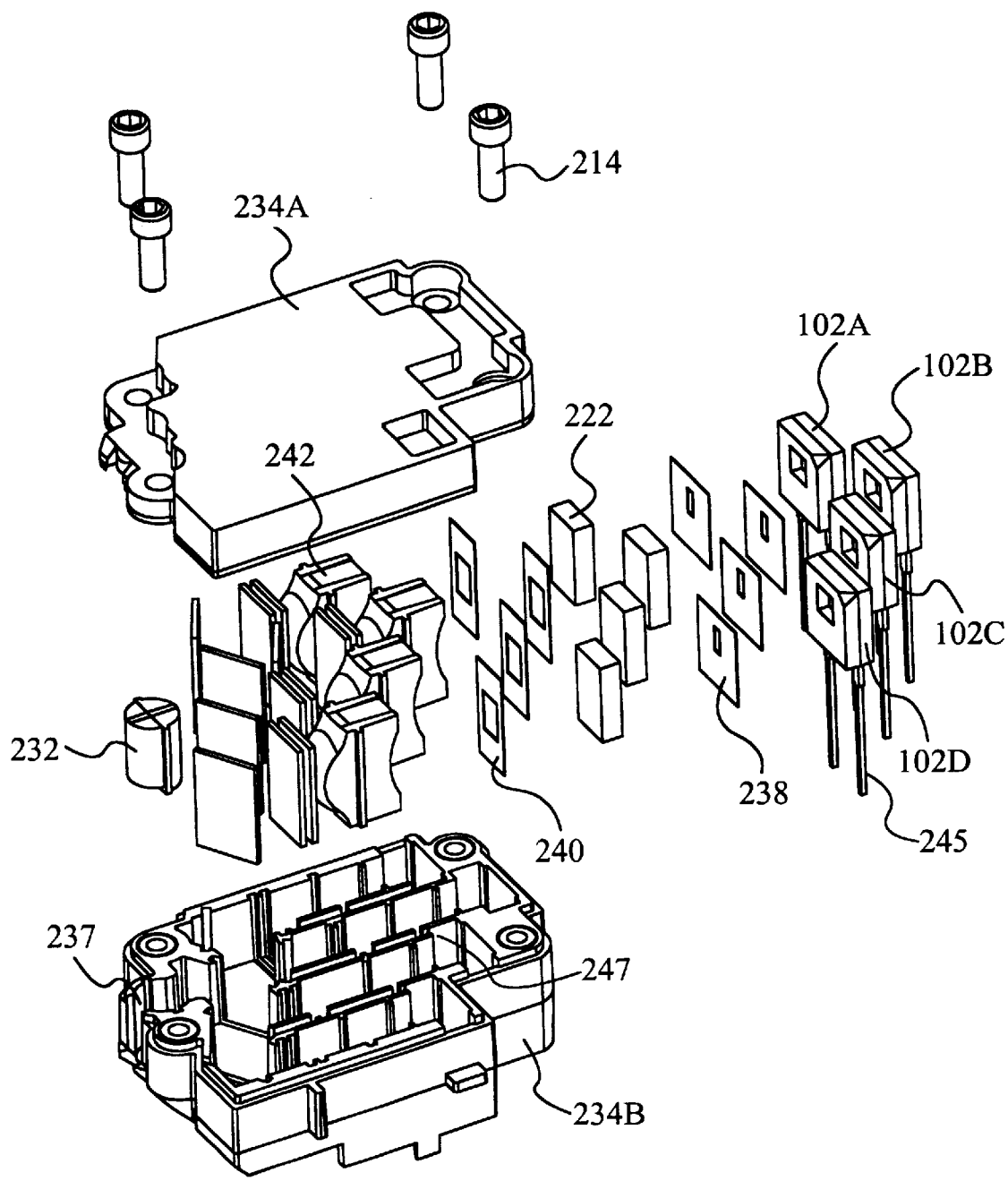
FIG. 9 is an exploded view of the detection assembly of FIG. 8.

FIG. 8 is a schematic, plan view of the optical detection assembly 48 of the heat-exchanging module. The assembly 48 is positioned adjacent the reaction vessel 2 to receive light emitted from the chamber 10. FIG. 9 is an exploded view of the detection assembly 48. As shown in FIGS. 8–9, the assembly 48 includes a housing 221 for holding various components of the assembly. The housing 221 preferably comprises one or more molded plastic pieces. In the preferred embodiment, the housing 221 is a multi-part housing comprised of upper and lower housing elements 234A and 234B. The housing elements 234A, 234B are complementary, mating pieces that are held together by screws 214. In alternative embodiments, the entire housing 221 may be a one-piece housing that holds a slide-in optics package.

The lower housing element 234B includes an optical window 237 into which is placed a cylindrical rod lens 232 for collimating light emitted from the chamber 10. In general, the optical window may simply comprise an opening in the housing through which the emitted light may be received. The optical window may optionally include an optically transmissive or transparent piece of glass or plastic serving as a window pane, or as in the preferred embodiment, the lens 232 for collimating light emitted from the chamber 10.

The optics assembly 48 also includes four detectors 102A, 102B, 102C, and 102D for detecting light emitted from the chamber 10 and received through the window 237. In general, each detector may be a photomultiplier tube, CCD, SMOS detector, photodiode, or other solid-state detector. In the preferred embodiment, each detector is a PIN photodiode. The detectors 102A, 102B, 102C, and 102D are preferably rigidly fixed in recesses formed in the lower housing element 234B. The detectors are electrically connected by leads 245 to the optical circuit board 52 (see FIG. 4) which is preferably mounted to the underside of the lower housing element 234B.

The optics assembly 48 further includes a set of filters and lenses arranged in the housing 221 for separating light emitted from the chamber 10 into different emission wavelength ranges and for directing the light in each of the emission wavelength ranges to a respective one of the detectors. As shown in FIG. 9, the lower housing element 234B preferably includes walls 247 that create separate detection channels in the housing, with one of the detectors positioned at the end of each channel. The walls 247 preferably include slots for receiving and rigidly holding the filters and lenses. The filters and lenses may also be rigidly fixed in the housing 221 by an adhesive used alone, or more preferably, with an adhesive used in combination with slots in the housing.

In general, the filters in the optics assembly 48 may be selected to block light emitted from the chamber 10 outside of any desired emission wavelength ranges. The optics assembly 48 may therefore be used with any fluorescent, phosphorescent, chemiluminescent, or electrochemiluminescent labels of interest. For purposes of illustration, one specific embodiment of the assembly 48 will now be described in which the assembly is designed to detect light emitted from the chamber 10 in the peak emission wavelength ranges of FAM, TAMRA, TET, and ROX.

In this embodiment, the set of filters preferably includes a 515 nm Schott Glass® filter 222A positioned in front of the first detector 102A, a 550 nm Schott Glass® filter 222B positioned in front of the second detector 102B, a 570 nm Schott Glass® filter 222C positioned in front of the third detector 102C, and a 620 nm Schott Glass® filter 222D positioned in front of the fourth detector 102D. These Schott Glass® filters are commercially available from Schott Glass Technologies, Inc. of Duryea, Pa. The optics assembly 48 also includes a pair of 505 nm high pass filters 223 positioned in front of the first detector 102A, a pair of 537 nm high pass filters 224 positioned in front of the second detector 102B, a pair of 565 nm high pass filters 225 positioned in front of the third detector 102C, and a pair of 605 nm high pass filters 226 positioned in front of the fourth detector 102D.

Although it is presently preferred to position a pair of high pass filters in front of each detector for double filtering of light, a single filter may be used in alternative embodiments. In addition, a lens 242 is preferably positioned in each detection channel between the pair of high pass filters and the Schott Glass® filter for collimating the filtered light. The optics assembly 48 further includes a 605 nm high pass reflector 227, a mirror 228, a 565 nm low pass reflector 229, a 537 nm high pass reflector 230, and a 505 nm high pass reflector 231. The reflecting filters and mirrors 227–231 are preferably angularly offset by 30° from the high pass filters 223–226. As shown in FIG. 9, the detection assembly 48 also preferably includes a first aperture 238 positioned between each detector and Schott Glass® filter 222 and an aperture 240 positioned between each lens 242 and Schott Glass® filter 222. The apertures 238, 240 reduce the amount of stray or off-axis light that reaches the detectors 102A, 102B, 102C, and 102D.

The detection assembly 48 detects light emitted from the chamber 10 in four emission wavelength ranges as follows. As shown in FIG. 8, the emitted light passes through the lens 232 and strikes the 565 nm low pass reflector 229. The portion of the light having a wavelength in the range of about 505 to 537 nm (corresponding to the peak emission wavelength range of FAM) reflects from the 565 nm low pass reflector 229, passes through the 537 nm high pass reflector 230, reflects from the 505 nm high pass reflector 231, passes through the pair of 505 nm high pass filters 223, through the lens 242, through the 515 nm Schott Glass® filter 222A, and is detected by the first detector 102A.

Meanwhile, the portion of the light having a wavelength in the range of about 537 to 565 nm (corresponding to the peak emission wavelength range of TET) reflects from the 565 nm low pass reflector 229, reflects from the 537 nm high pass reflector 230, passes through the pair of 537 nm high pass filters 224, through the lens 242, through the 550 nm Schott Glass® filter 222B, and is detected by the second detector 102B.

Similarly, the portion of the light having a wavelength in the range of about 565 to 605 nm (corresponding to the peak emission wavelength range of TAMRA) passes through the 565 nm low pass reflector 229, through the 605 nm high pass reflector 227, through the pair of 565 nm high pass filters 225, through the lens 242, through the 570 nm Schott Glass® filter 222C, and is detected by the third detector 102C. The portion of the light having a wavelength over 605 nm (corresponding to the peak emission wavelength range of ROX) passes through the 565 nm low pass reflector 229, reflects from the 605 nm high pass reflector 227, reflects from the mirror 228, passes through the pair of 605 nm high pass filters 226, through the lens 242, through the 620 nm Schott Glass® filter 222D, and is detected by the fourth detector 102D. In operation, the outputs of detectors 102A, 102B, 102C, and 102D are analyzed to determine the concentrations of each of the different dyes contained in the chamber 10, as will be described in greater detail below.

Figure 10:
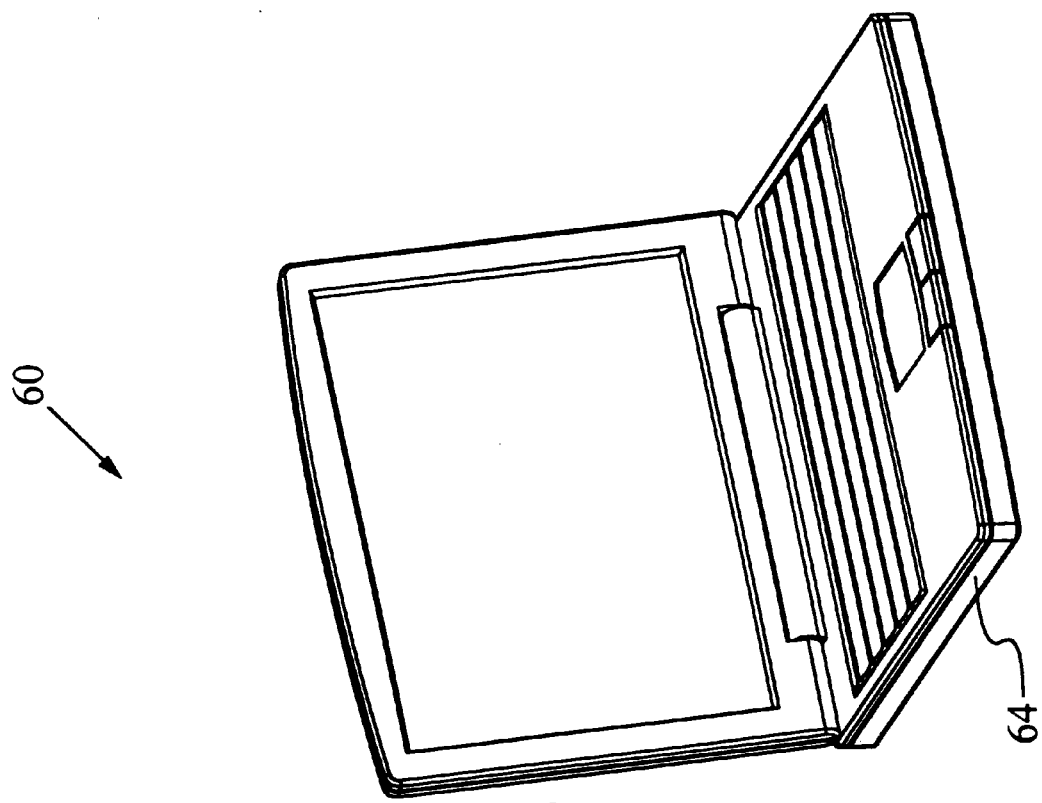
FIG. 10 is a perspective view of a multi-site reactor system having dynamic, independent, computer-implemented control of each reaction site.
Figure 10:
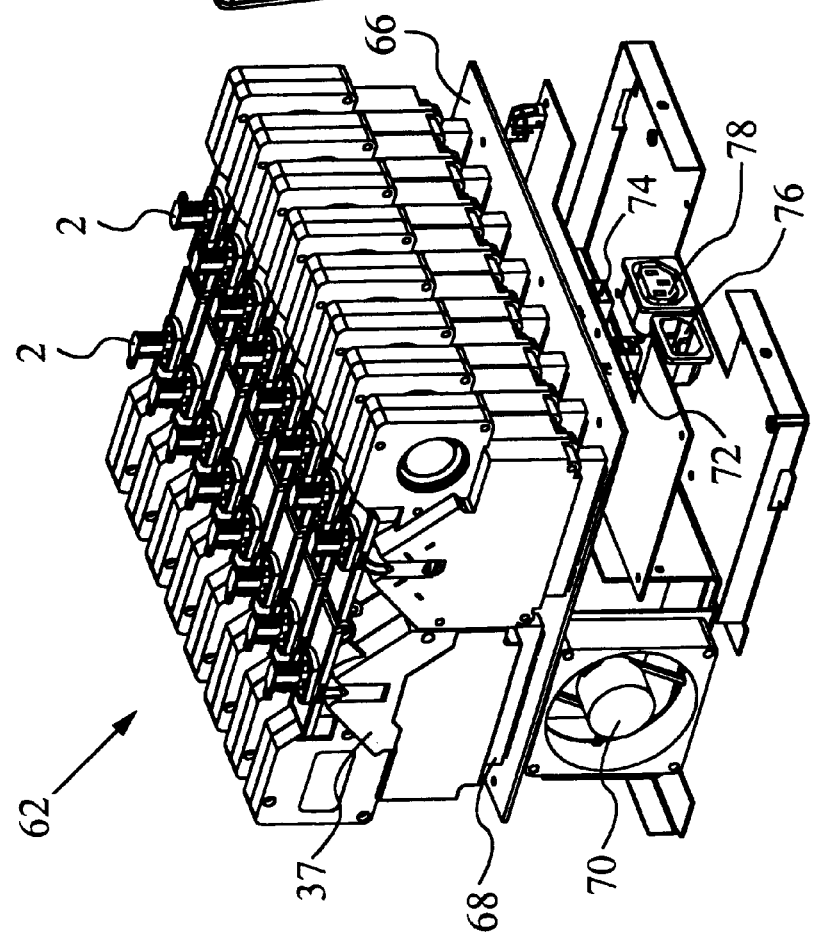

FIG. 10 is a perspective view of a multi-site reactor system 60 according to the present invention. The reactor system 60 comprises a thermal cycler 62 and a controller, such as a personal computer 64. The thermal cycler 62 comprises a base instrument 66 and multiple heat-exchanging modules 37 (described with reference to FIG. 4). The base instrument 66 has a main logic board with edge connectors 68 for receiving the modules 37. The base instrument 66 also preferably includes a fan 70 for cooling its electronic components. The base instrument 66 may be connected to the controller 64 using any suitable data connection, such as a universal serial bus (USB), ethernet connection, or serial line. It is presently preferred to use a USB that connects to the serial port of computer 64. Although a laptop computer is shown in FIG. 10, the controller may comprise any type of device having a processor. Further, the thermal cycler may be linked to a computer network rather than to a single computer.

The term "thermal cycling" is herein intended to mean at least one change of temperature, i.e. increase or decrease of temperature, in a reaction mixture. Therefore, chemicals undergoing thermal cycling may shift from one temperature to another and then stabilize at that temperature, transition to a second temperature or return to the starting temperature. The temperature cycle may be performed only once or may be repeated as many times as required to study or complete the particular chemical reaction of interest.

In the specific embodiment of FIG. 10, the thermal cycler 62 includes sixteen independently-controllable heat-exchanging modules 37 arranged in two rows of eight modules each. It is to be understood, however, that the thermal cycler can range from a one to four-site hand-held instrument to a multi-hundred site clinical and research instrument. Common to all these embodiments are one or more independently-controllable modules 37, and a controller for operating individually programmed independent temperature/time profiles for each module. The thermal time-courses for nucleic acid amplifications or other reactions can be fine tuned to a particular target, and independent control of individual modules 37 permits simultaneous reactions to be run at different thermal profiles.

The thermal cycler 62 also provides for independent loading, cycling, and unloading of individual sites at different times allowing for optimal use and throughput. The thermal cycler 62 is also modular, in that each heat-exchanging module 37 can be individually removed from the base instrument 66 for servicing, repair, or replacement. This modularity reduces downtime since all the modules 37 are not off line to repair one, and the instrument 66 can be upgraded and enlarged to add more sites as needed. The modularity of the thermal cycler 62 also means that individual modules 37 can be precisely calibrated, and module-specific schedules or corrections can be included in the control programs, e.g., as a series of module-specific calibration or adjustment charts.

The thermal cycling system 60 of the invention also has significant advantages in terms of power management. The controller 64 can interleave the thermal profiles of each independent module 37 to save power as compared to a single block heater. For example, current can be reduced by half by control of one module to heat (high power) while a second module is cooling (low power). Thus, by interleaving of pulse power to only so many modules 37 as have reactants in them, the instantaneous current requirements for the base instrument 66 can be minimized, permitting more modules 37 per instrument that can still be powered from a standard 110V, 15 ampere circuit. Because of this sophisticated power management system, which is made possible by the independent control of the modules 37, the instrument 66 may also be configured into a hand-held, battery operated device.

In embodiments in which the base instrument 66 operates on external power, e.g. 110 V AC, the instrument preferably includes two power connections 76, 78. Power is received though the first connection 76 and output through the second connection 78. Similarly, the instrument 66 preferably includes network interface inlet and outlet ports 72, 74 for receiving a data connection through inlet port 72 and outputting data to another base instrument through outlet port 74. As shown schematically in FIG. 11, this arrangement permits multiple thermal cyclers 62A, 62B, 62C, 62D to be daisy-chained from one controller 64 and one external power source 80. Using a USB, it is theoretically possible to daisy-chain 127 thermal cycler instruments to a single controller, although due to limits of computing power, one should use several computers for controlling 127 instruments.

Figure 12:
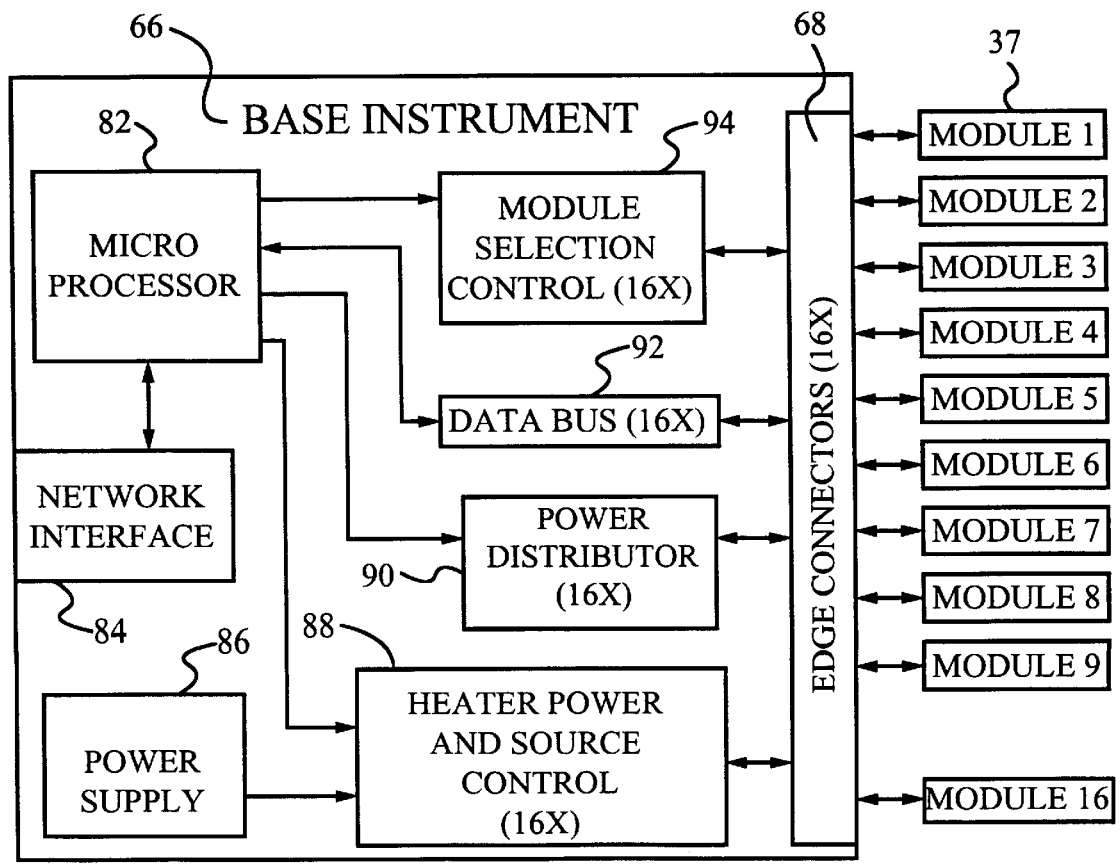
FIG. 12 is a schematic, block diagram of a base instrument of the system of FIG. 10.

FIG. 12 is a schematic, block diagram of the base instrument 66. The base instrument includes a power supply 86 for supplying power to the instrument and to each module 37. The power supply 86 may comprise an AC/DC converter for receiving power from an external source and converting it to direct current, e.g., receiving 110V AC and converting it to 12V DC. Alternatively, the power supply 86 may comprise a battery, e.g., a 12V battery.

The base instrument 66 also includes a microprocessor or microcontroller 82 containing firmware for controlling the operation of the base instrument 66 and modules 37. The microcontroller 82 communicates through a network interface 84 to a user interface computer via a USB. Due to current limitations of processing power, it is currently preferred to include at least one microcontroller in the base instrument per sixteen modules 37. Thus if the base instrument has a thirty-two module capacity, at least two microcontrollers should be installed in the instrument 66 to control the modules.

The base instrument 66 further includes a heater power source and control circuit 88, a power distributor 90, a data bus 92, and a module selection control circuit 94. Due to space limitations in patent drawings, control circuit 88, power distributor 90, data bus 92, and control circuit 94 are shown only once in the schematic diagram of FIG. 12. However, the base instrument 66 actually contains one set of these four functional components 88, 90, 92, 94 for each heat-exchanging module 37. Thus, in the embodiment of FIG. 12, the base instrument 66 includes sixteen control circuits 88, power distributors 90, data buses 92, and control circuits 94.

Similarly, the base instrument 66 also includes one edge connector 68 for each module 37 so that the instrument includes sixteen edge connectors for the embodiment shown in FIG. 12. The edge connectors are preferably 120 pin card edge connectors that provide cableless connection from the base instrument 66 to each of the modules 37. Each control circuit 88, power distributor 90, data bus 92, and control circuit 94 is connected to a respective one of the edge connectors and to the microcontroller 82.

Each heater power and source control circuit 88 is a power regulator for regulating the amount of power supplied to the heating element(s) of a respective one of the modules 37. The source control circuit 88 is preferably a DC/DC converter that receives a +12V input from the power supply 86 and outputs a variable voltage between 0 and −24V. The voltage is varied in accordance with signals received from the microcontroller 82.

Each power distributor 90 provides −5v, +5V, +12V, and GND to a respective module 37. The power distributor thus supplies power for the electronic components of the module. Each data bus 92 provides parallel and serial connections between the microcontroller 82 and the digital devices of a respective one of the modules 37. Each module selection controller 94 allows the microcontroller 82 to address an individual module 37 in order to read or write control or status information.

Figure 13:
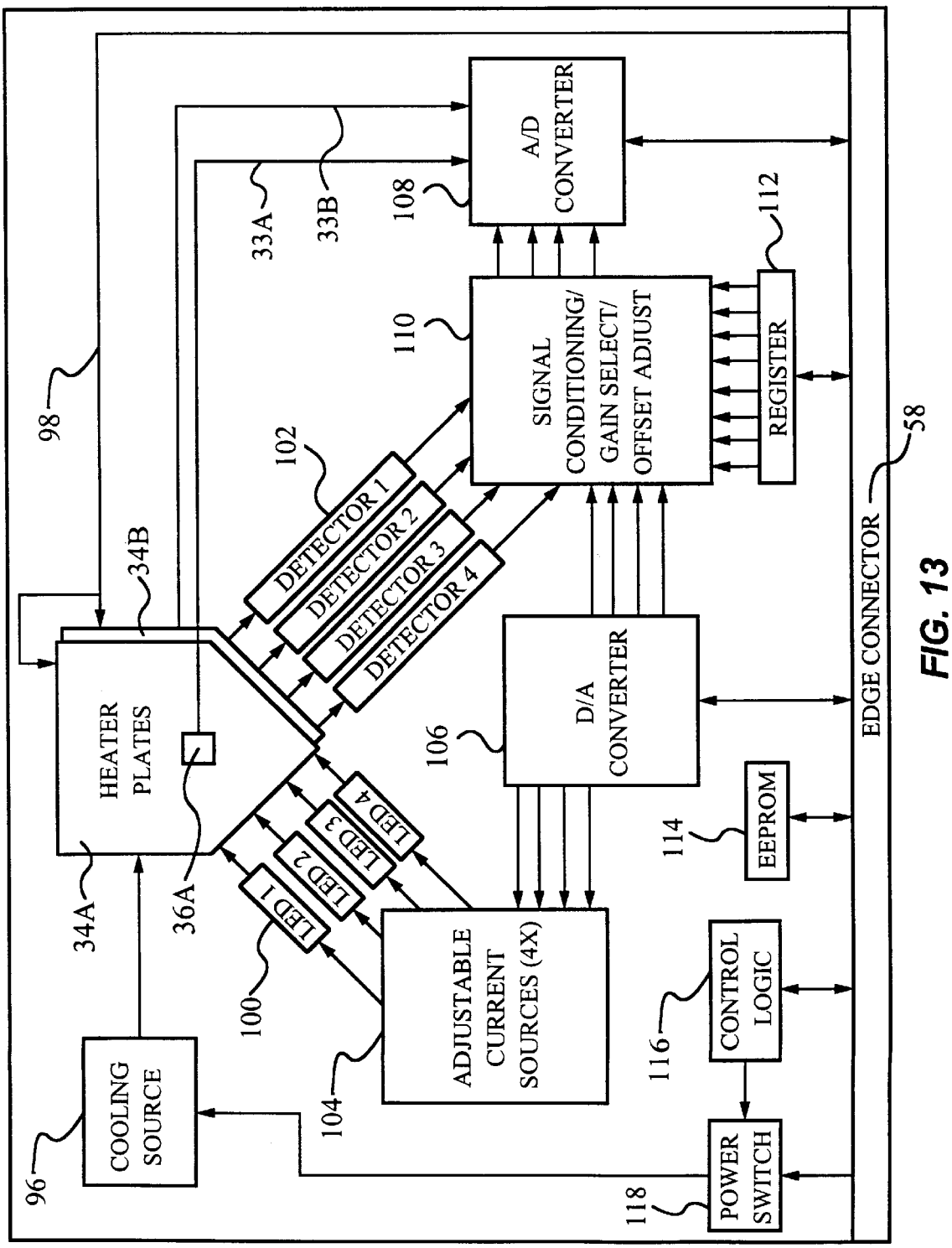
FIG. 13 is a schematic, block diagram of the electronic components of the heat-exchanging module of FIG. 4.

FIG. 13 is a schematic, block diagram of the electronic components of a heat-exchanging module 37. Each module includes an edge connector 58 for cableless connection to a corresponding edge connector of the base instrument. The module also includes heater plates 34A, 34B each having a resistive heating element as described above. The plates 34A, 34B are wired in parallel to receive power input 98 from the base instrument. The plates 34A, 34B also include thermistors 36A, 36B that output analog temperature signals to an analog-to-digital converter 108. The converter 108 converts the analog signals to digital signals and routes them to the microcontroller in the base instrument through the edge connector 58.

The heat-exchanging module also includes a cooling system, such as a fan 96, for cooling the plates 34A, 34B and the reaction mixture contained in a vessel inserted between the plates. The fan 96 receives power from the base instrument and is activated by switching a power switch 118. The power switch 118 is in turn controlled by a control logic block 116 that receives control signals from the microcontroller in the base instrument.

The module further includes four light sources, such as LEDs 100, for excitation of labeled analytes in the reaction mixture and four detectors 102, preferably photodiodes, for detecting fluorescent emissions from the reaction mixture. The module also includes an adjustable current source 104 for supplying a variable amount of current (e.g., in the range of 0 to 30 mA) to each LED to vary the brightness of the LED. A digital-to-analog converter 106 is connected between the adjustable current source 104 and the microcontroller of the base instrument to permit the microcontroller to adjust the current source digitally.

The adjustable current source 104 is preferably used to ensure that each LED has about the same brightness when activated. Due to manufacturing variances, many LEDs have different brightnesses when provided with the same amount of current. Therefore, it is presently preferred to test the brightness of each LED during manufacture of the heat-exchanging module and to store calibration data in a memory 114 of the module. The calibration data indicates the correct amount of current to provide to each LED. The microcontroller reads the calibration data from the memory 114 and controls the current source 104 accordingly. The microcontroller may also control the current source to adjust the brightness of the LEDs 100 in response to optical feedback received from the detectors 102, as is described in greater detail below.

The module additionally includes a signal conditioning/gain select/offset adjust block 110 comprised of amplifiers, switches, electronic filters, and a digital-to-analog converter. The block 110 adjusts the signals from the detectors 102 to increase gain, offset, and reduce noise. The microcontroller in the base instrument controls block 110 through a digital output register 112. The output register 112 receives data from the microcontroller and outputs control voltages to the block 110. The block 110 outputs the adjusted detector signals to the microcontroller through the analog-to-digital converter 108 and the edge connector 58. The module also includes the memory 114, preferably a serial EEPROM, for storing data specific to the module, such as calibration data for the LEDs 100, thermal plates 34A, 34D, and thermistors 36A, 36B, as well as calibration data for a deconvolution algorithm described in detail below.

Figure 14:
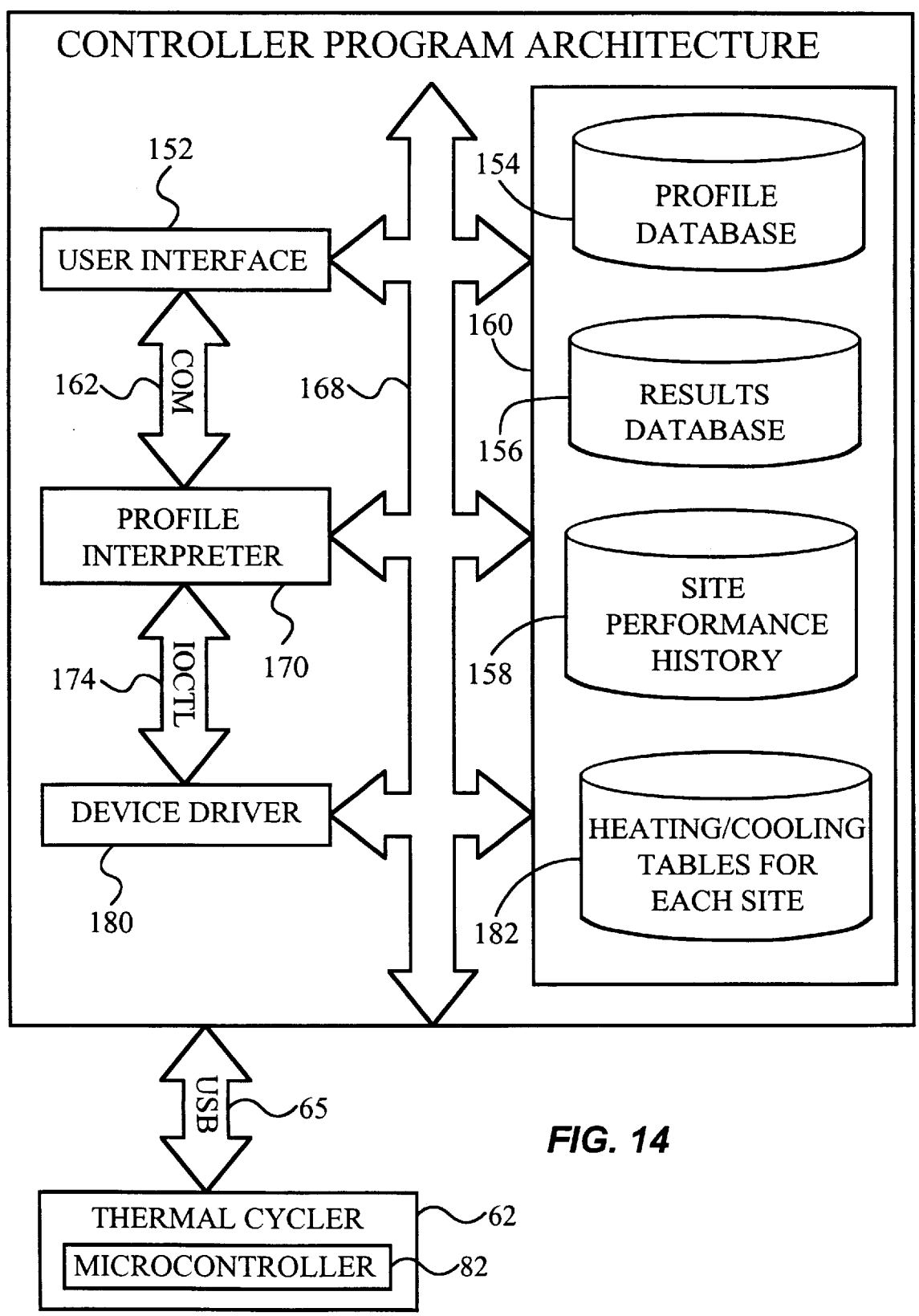
FIG. 14 is a schematic, block diagram illustrating the computer controller architecture for the control, diagnostics, programming, and operational functions of the system of FIG. 10.
Figure 15:
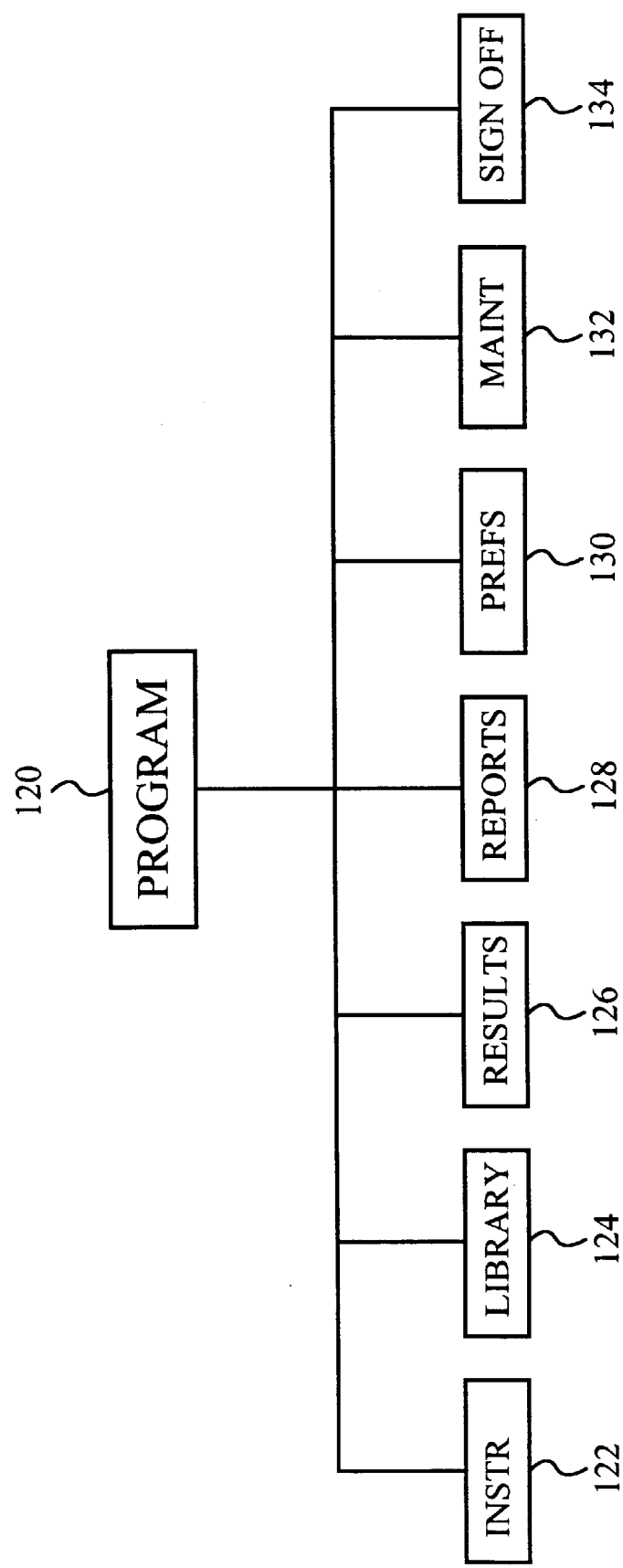
FIG. 15 is a block diagram showing the architecture of FIG. 14 that is preferably reproduced on a graphical user interface for selection of a function by a user.

FIG. 14 shows the controller architecture, typically resident as software, firmware, or a combination thereof, in a user interface computer and/or the microcontroller 82 of the thermal cycler 62. It should be understood that selected ones of these functions can be located, as needed, in the microcontroller 82, for example in the case of a hand-held field unit, or in a separate computer that communicates with the microcontroller. The distribution of the control functions can be selected by one skilled in the art to be resident in various hardware or software elements to suit the intended use most efficiently. Thus, the control function distribution in a large laboratory or clinical configuration may be quite different than in the hand-held field unit, or intermediate sized mobile unit. In addition, the functions can be selected for the particular purpose, ranging for example from qualitative identification, to single or limited number of site programs, to full quantitative evaluation of a wide range of reactions via an extended library of programs.

Continuing with FIG. 14, the controller program architecture is software that includes user interface functionality 152 including graphic displays on a monitor (sample displays are shown in FIGS. 15–18), an input keyboard, mouse, and the like. Temperature profiles are stored in a profile database 154 in a memory 160. The results of individual runs for individual reaction sites are also stored in a results database 156.

The user input device (such as a mouse or keyboard) permits user communication with a profile interpreter 170 via a comport 162. Upon user selection, a thermal cycle profile to be run on a selected one of the heat-exchanging modules is selected from the user interface 152, retrieved from the profile database 154, and input to the profile interpreter 170. Additionally, temperature signals obtained from the thermal cycler 62 via a device driver 180 are output from the profile interpreter 170 and input to the user interface 152.

The profile interpreter 170 converts selected thermal profiles into signals representing a set of heater power levels and fan on/off times in order to accomplish the thermal profile selected for each particular heat-exchanging module. An input/output control port 174 outputs a target temperature that becomes an input for the device driver 180. Likewise, the device driver 180 outputs the current temperature sensed by the temperature sensor of each heat-exchanging module as data that becomes the input to the profile interpreter 170. The device driver 180 also provides appropriate digital signals to the microcontroller 82 in the thermal cycler 62 through the serial bus 65. The microcontroller 82 then runs the temperature profile cycle.

FIGS. 15–18 illustrate a series of sample graphical displays that are displayed to the user on the user interface. As one skilled in the art will appreciate, the conventional sign-on screen appears when the system initializes, allowing for user identification and any password protection authorization inputs. This is followed by the Program Menu screen 120 of FIG. 15. By selecting the Instructions menu button 122 on the left, additional screens are accessed at any time. As each screen is displayed, it presents options for system operation in text boxes and buttons, along with the text or icon information directing the user how to select each of the options. The creation of these types of screens, including select buttons, check boxes text and graph displays, can be performed by a computer programmer having ordinary skill in the art.

The Library button 124 accesses thermal profile programs and stored results of past thermal cycle runs that are stored in memory. The result button 126 accesses a menu for viewing past results. The reports button 128 permits printing records of actual time course temperature traces from past thermal cycle runs. The preferences button 130 allows the user to set frequently used inputs runs, while the maintenance button 132 allow the user to adjust data structures. The Sign-Off button 134 closes the program.

Figure 16:
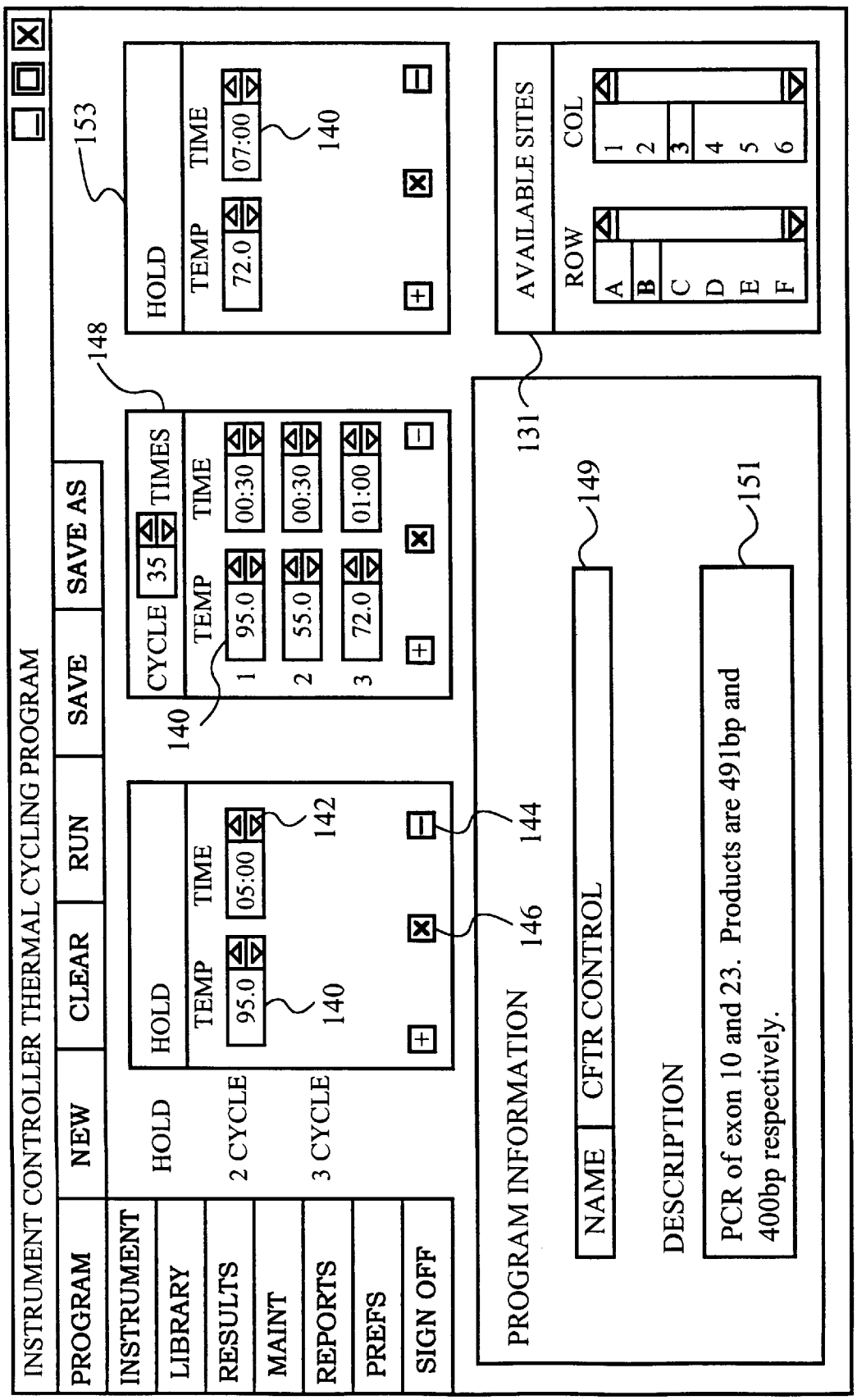

FIG. 16 illustrates a sample Program Menu screen through which site programs or thermal profiles (a series of one or more heating and cooling steps) are created. New profiles are created by selecting the NEW button. The template shown permits the user to create a specific user-defined program that is stored in memory. All of the data shown on the screen can be removed by selecting the CLEAR button to start from scratch. The numbers appearing in the small windows 140 disappear, and the user can then enter appropriate values by toggling the up or down arrows 142 under the columns "Temp" and "Time". The plus and minus keys 144 are used to add or delete steps. Selecting the lower case "x" key 146 deletes the entire field. The program interprets a single step as a "hold". Multiple steps are interpreted as a cycle, and as noted in the center column 148, the number of cycles may be entered by the user. The program name 149 is in the center left window and a brief description 151 of the program to be run is in the lower left window. The program then can be saved under either "Save" with a previously known name or under "Save As" to save the program under the name entered in the window 149. This new program is then automatically stored in the thermal profile library, e.g., the profile database 154 of FIG. 14. By pressing the "Run" button, the available reaction sites (heat-exchanging modules) are displayed in column 131 by specific address. One or more sites can be selected and the program run by again hitting the "Run" button.

Figure 17:
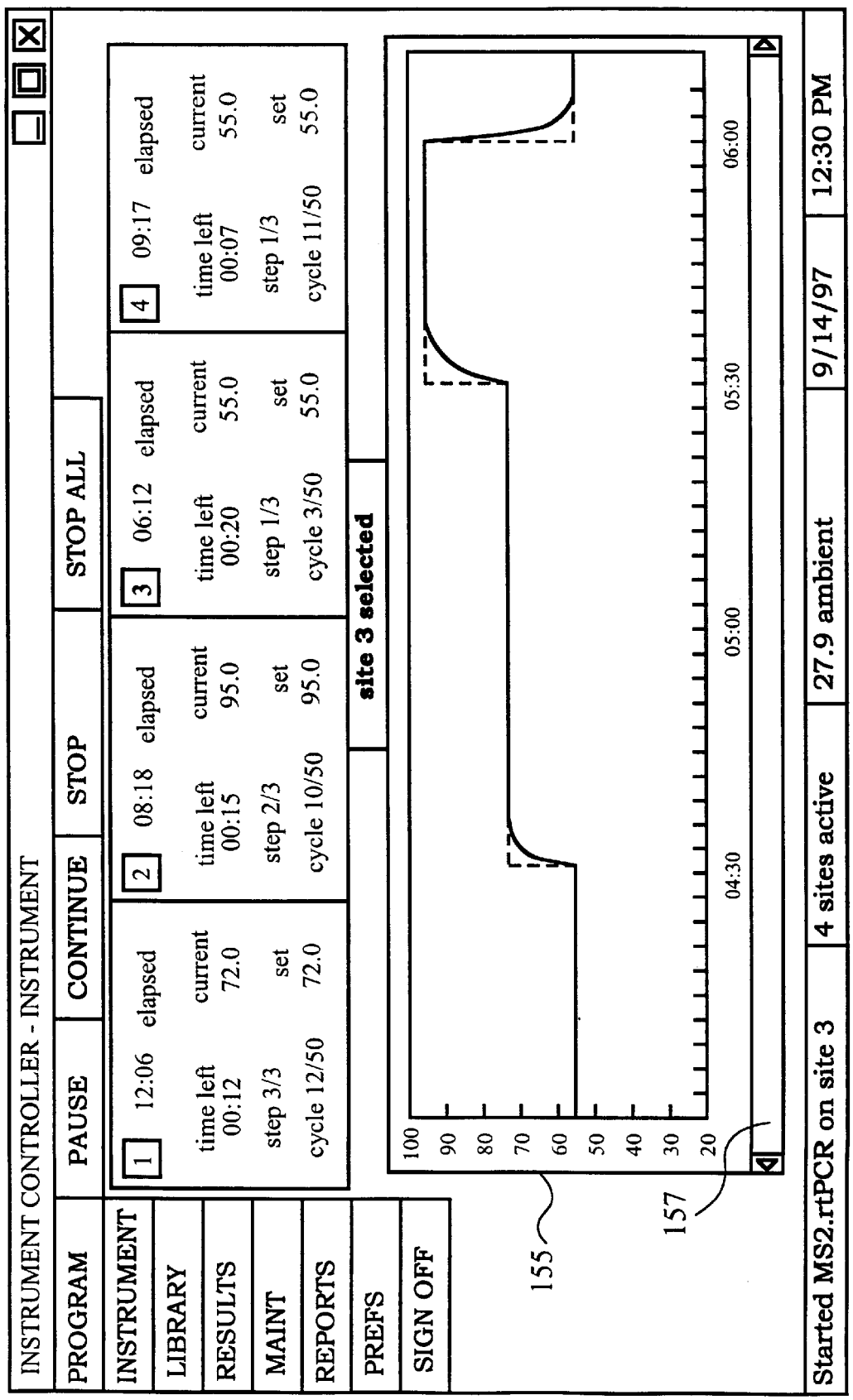

FIG. 17 illustrates a sample Instrument Menu Screen that displays current thermal cycling status. Each of the four windows labeled 1, 2, 3, 4 identifies one of the four reaction sites (modules) in a four-module instrument. Note that site number 3 has been selected, and it shows the total time to run at the setpoint temperature of 55° C. It also shows both the profile setting and the current temperature, as well as the time left in that particular step. The screen also shows that it is in step one of three steps and cycle 3 of 50 cycles, with 20 seconds left in that cycle. The screen also displays a real-time trace, the curved line in the display 155 across the bottom half of the screen, of the progress of the reaction. The individual sites can be polled by simply selecting the specific sites 1, 2, 3, 4 . . . N by number.

Additional commands include "Pause", "Continue" and "Stop" to effect the particular reaction site selected. The "Stop All" command stops all heat-exchanging modules currently in operation. A warning prompt appears when "Stop" or "Stop All" is selected to ensure that it was not selected inadvertently. Once the reaction is completed, the real-time display 155 of any particular cycle can be selected in this particular site by moving the scroll bar button 157 along the bottom of the graph.

Figure 18:
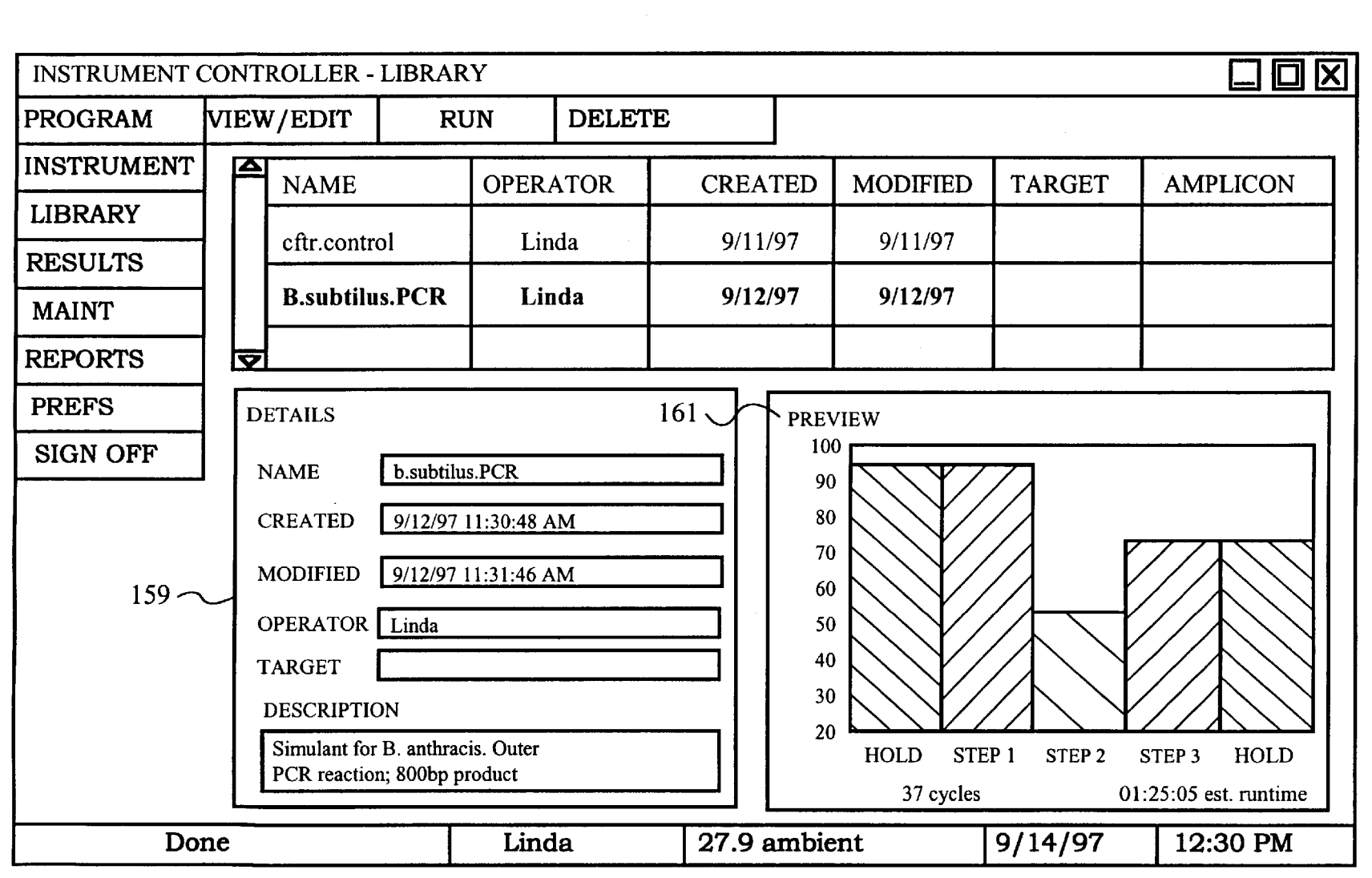

FIG. 18 illustrates a sample Library Menu Screen. As described above with reference to FIG. 14, previously saved programs are stored in the profile database 154. Results from previous runs are stored in the results database 156. Turning to FIG. 18, programs may be selected by scrolling down the program "Name" list in the upper half of the screen, and then assigned a specific reaction site (one of the heat-exchanging modules) by pressing "Run". Detailed information regarding individual programs is displayed on the lower left quarter 159 of the screen, and previously run programs can be recalled and viewed by selecting the "View/Edit" button. The "Delete" button is used to remove programs from the library after a warning pop-up notice. The Preview display 161 in the lower right of the screen shows a bar graph of the thermal profile selected.

The user interface program also preferably includes a Results Menu Screen in which the results of a particular run are displayed by program name, date, operator, and site. The results can be either real-time results from the operations of the program, or the results can be called up from memory (results database 156 in FIG. 14). The information displayed preferably includes a temperature trace of the entire run of cycles for a selected thermal program and the optical data collected. The information displayed also preferably includes the time the program started and finished, the particular heat-exchanging module (reaction site) used, and the final program status (e.g., completed, failed, or stopped by user).

Figure 19:
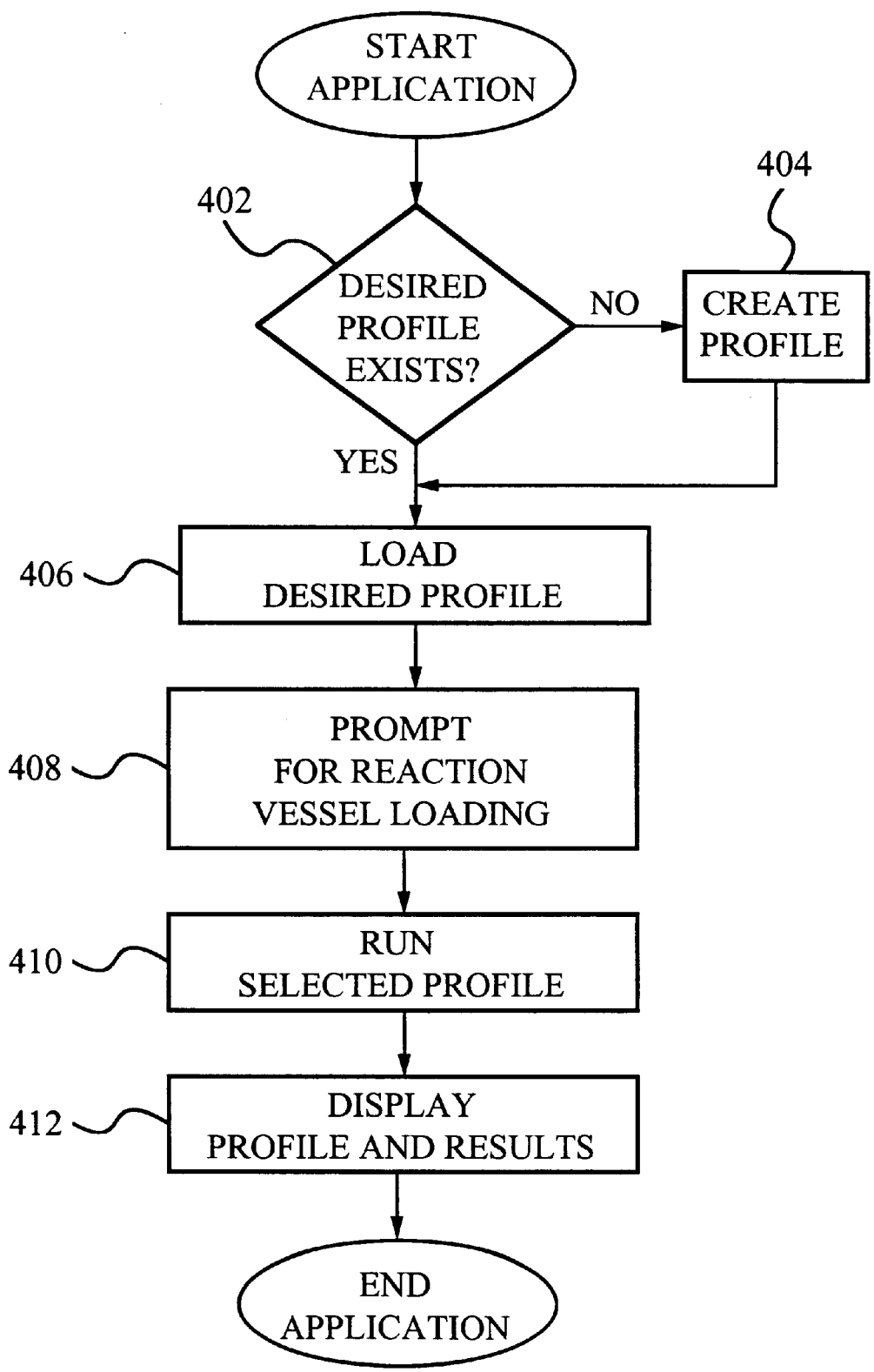
FIG. 19 is a flow diagram showing the overall control and operation of the system of FIG. 10.

FIG. 19 is a flow-diagram schematically illustrating the steps in the overall software control application executed by the controller of the multi-site reactor system. The application is loaded and executed beginning at step 402 where it is determined whether a temperature profile desired by the user exists. If the profile exists, the controller proceeds to step 306. If the desired profile does not exist, it is created by the user in step 404.

Figure 11:
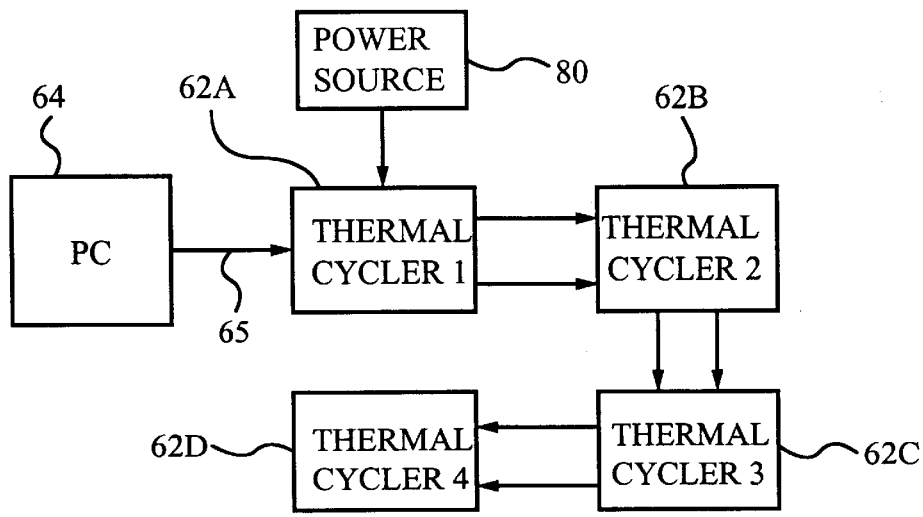
FIG. 11 is a schematic, block diagram of another multisite reaction system having multiple thermal cycling instruments daisy-chained to a computer and a power source.

The profile is preferably created through the instrument controller screen shown in FIG. 11. The user/operator initializes the profile variables, e.g., entering the number of the cycles and the setpoint temperatures for each of the temperature steps of a given profile via keyboard and/or selection from the buttons and check boxes on the program graphics display. For example, as shown in FIG. 11, the user may select for the particular application to begin with a 5 minute induction hold at 95° C., then run 35 cycles (repeats) at 95° C. for 30 seconds, cool to 55° C. for 30 seconds, then raise the temperature to 72° C. for 60 seconds. A final hold at 72° C. for 7 minutes may be selected before signaling the run is complete. This temperature profile is then saved in the profile database.

In step 406, the desired temperature profile is loaded from the profile database in response to the user requesting that the profile be run at a selected one of the heat-exchanging modules. In step 408, the controller prompts the user through the user interface to load a reaction vessel containing a reaction mixture into the selected module. Referring to FIG. 4, the user then places the reaction vessel 2 containing the reaction mixture between the thermal plates 34A, 34B of the selected module 37. Those skilled in the art will appreciate that this step may also be automated using, e.g., robotics. In step 410, the controller runs the selected temperature profile on the reaction mixture in the selected module. Step 410 is described in detail below with reference to FIG. 20. Briefly, the selected temperature profile is compiled by the profile interpreter 170 into an intermediate form that is used by the device driver 180 to provide signals to the microcontroller 82 of the thermal cycler instrument 62 (see FIG. 14).

The running of the selected temperature profile generally includes iterative loops of polling, pinging, or sampling temperature sensor data and associating the data with the predetermined setpoint temperatures as clock time progresses. At the same time, the controller displays both the selected profile and the current temperature of the thermal plates in the selected heat-exchanging module in real-time on screen as the thermal cycles are run. A cycle counter j is originally initialized to $j_o=o$, and it iterates in each cycle to the number of cycles chosen. After the chosen number of cycles are completed, the program signals that the particular run is "Done", the timer counter having reached the total time for cycles. In step 412, the controller displays the results of the run, e.g., the optical data indicating detection of target analytes in the reaction mixture, and saves the results in the results database.

Figure 20:
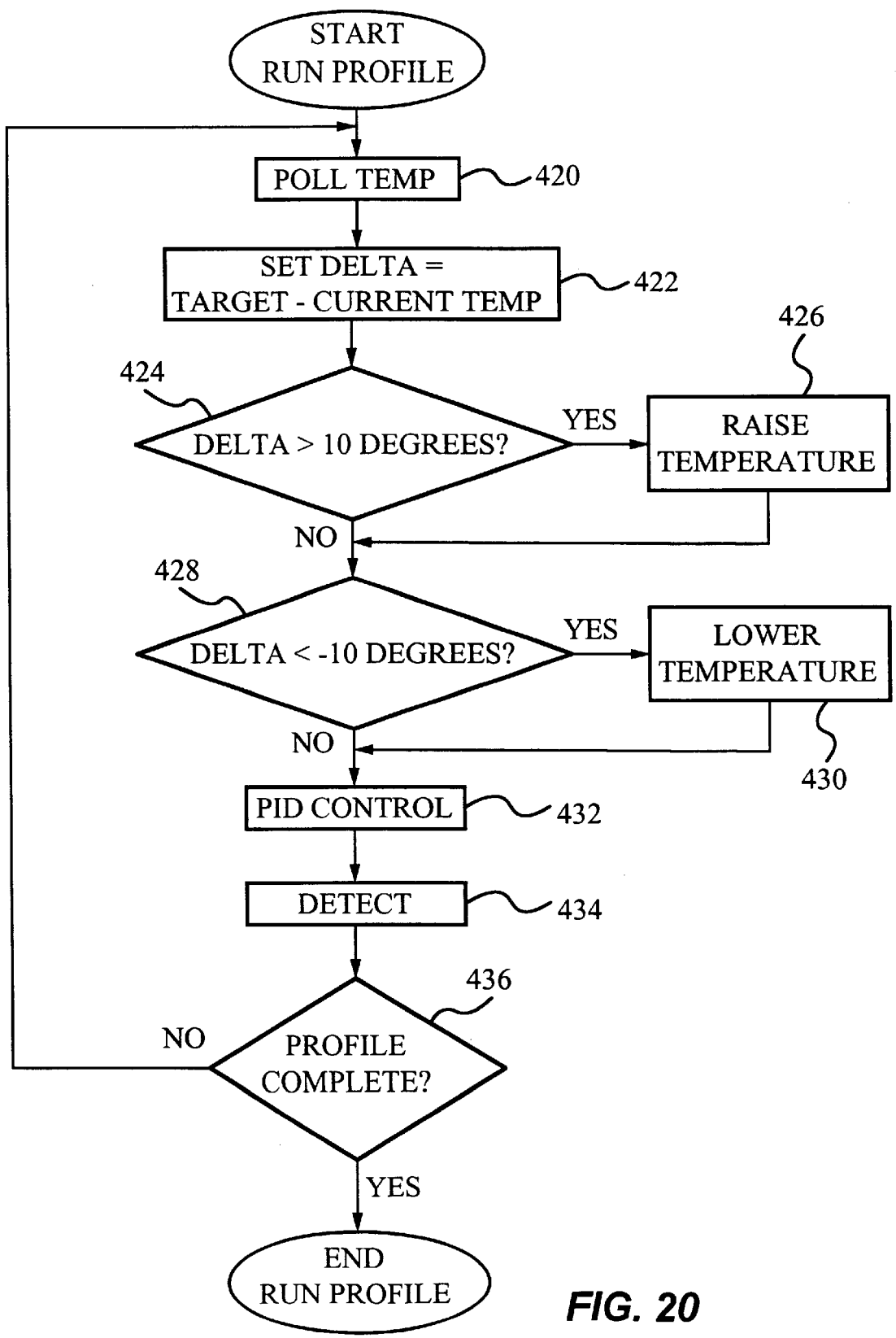
FIG. 20 is a flow diagram showing the steps for running a selected temperature profile on the system of FIG. 10.

FIG. 20 illustrates the steps executed in the running of the selected temperature profile (step 410 in FIG. 19) for a reaction mixture in a selected heat-exchanging module. In step 420, the temperature of the thermal plates in the module is polled. Polling of the plate temperature preferably occurs every 100 milliseconds throughout the running of the temperature profile. As shown in FIG. 3, the temperature sensors, such as thermistors 36A, 36B output analog signals indicating the temperature of the plates. The analog signals are converted to digital signals and received by the controller. The controller averages the temperatures of the two plates to determine a plate temperature.

In step 422, the controller determines the difference (delta) between the profile target temperature, i.e. the setpoint temperature defined by the user for the particular time in the profile, and the plate temperature. In decision step 424, it is determined if the difference is greater than a threshold value, e.g., 10° C. If the difference is greater than the threshold value, the controller proceeds to step 426, raising the temperature of the plates. The steps included in raising the plate temperature are described in detail below with reference to FIG. 21.

If the difference is not greater than the threshold value, the controller determines in step 428 if the plate temperature is more than a predetermined amount, e.g., 10° C., higher than the current setpoint temperature. If it is, the controller proceeds to step 430, lowering the temperature of the plates. The steps included in lowering the temperature of the plates are described in detail below with reference to FIG. 22. Following step 430, the controller proceeds to step 432.

In step 432, the controller implements standard proportional-integral-derivative (PID) control for maintaining the thermal plates at the current setpoint temperature. Proportioning may be accomplished either by varying the ratio of "on" time to "off" time, or, preferably with proportional analog outputs as known in the art which decrease the average power being supplied either to the heater or the fan as the actual temperature of the plates approaches the setpoint temperature. PID control combines the proportional mode with an automatic reset function (integrating the deviation signal with respect to time) and rate action (summing the integral and deviation signal to shift the proportional band). Standard PID control is well known in the art and need not be described further herein.

In step 434, the reaction mixture contained in the reaction vessel is optically interrogated to determine if the mixture contains target analytes. Referring again to FIGS. 6 and 8, this is accomplished by sequentially activating LEDs 100A, 100B, 100C, and 100D to excite different fluorescently-labeled analytes in the mixture and by detecting light emitted (fluorescent output) from the chamber 10 using detectors 102A, 102B, 102C, and 102D. In the presently preferred embodiment, the fluorescent dyes FAM, TAMRA, TET, and ROX are used to label the target analytes, e.g., target nucleotide sequences, nucleic acids, proteins, pathogens, or organisms in the reaction mixture.

In the preferred embodiment, there are four pairs of LEDs and four detectors for a total of sixteen combinations of LED/detector pairs. It is theoretically possible to collect output signals from the detectors for all sixteen combinations. Of these sixteen combinations, however, there are only four primary detection channels. Each primary detection channel is formed by a pair of LEDs in the optics assembly 46 whose excitation beams lie in the peak excitation wavelength range of a particular dye and by one corresponding detection channel in the optics assembly 48 designed to detect light emitted in the peak emission wavelength range of the same dye.

In the preferred embodiment, the first primary detection channel is formed by the first pair of LEDs 100A and the fourth detector 102D (the ROX channel). The second primary detection channel is formed by the second pair of LEDs 100B and the third detector 102C (the TAMRA channel). The third primary detection channel is formed by the third pair of LEDs 100C and the first detector 102A (the FAM channel). The fourth primary detection channel is formed by the fourth pair of LEDs 100D and the second detector 102B (the TET channel). In the preferred embodiment, the reaction mixture is optically interrogated using only these four primary detection channels. In an alternative embodiment, however, one or more alternate detection channels is used to provide data for correcting potential variances in the output signals of the detectors caused by, e.g., air bubbles in the reaction vessel, variances in the shape of the vessel, or slight variances in the position of the vessel between the thermal plates. This alternative embodiment is discussed in greater detail below.

A preferred method for optically interrogating the reaction mixture and for deconvolving the optical data obtained will now be described with reference to FIGS. 6 and 8. First, prior to activating any of the LEDs, a "dark reading" is taken to determine the output signal of each of the four detectors when none of the LEDs are lit. The "dark reading" signal output by each detector is subsequently subtracted from the corresponding "light reading" signal output by the detector to correct for any electronic offset in the optical detection circuit. This procedure of obtaining "dark reading" signals and subtracting the dark signals from the corresponding "light reading" signals is preferably performed every time that a reaction vessel is optically interrogated, including those times the vessel is interrogated during the development of calibration data (described in detail below). For clarity and brevity of explanation, however, the steps of obtaining "dark reading" signals and subtracting the dark signals from the corresponding "light reading" signals will not be further repeated in this description.

Following the dark reading, a "light reading" is taken in each of the four primary optical detection channels as follows. The first pair of LEDs 100A is activated and the LEDs generate an excitation beam that passes through the pair of 593 nm low pass filters 203, reflects off of the 593 nm low pass reflector 212, passes through the 555 nm, low pass reflector 211, reflects off of the 527 nm high pass reflector 209, and passes through the lens 215 into the reaction chamber 10. The excitation beam from the LEDs 100A is thus filtered to a wavelength range of 555 to 593 nm corresponding to the peak excitation range for ROX. As shown in FIG. 8, emitted light (fluorescence emission radiation) from the chamber 10 passes through the lens 232 of the detection assembly 48 and strikes the 565 nm low pass reflector 229. The portion of the light having a wavelength over 605 nm (corresponding to the peak emission wavelength range of ROX) passes through the 565 nm low pass reflector 229, reflects from the 605 nm high pass reflector 227, reflects from the mirror 228, passes through the pair of 605 nm high pass filters 226, through the lens 242, through the 620 nm Schott Glass® filter 222D, and is detected by the fourth detector 102D. The fourth detector 102D outputs a corresponding signal that is converted to a digital value and recorded.

Next, as shown in FIG. 6, the second pair of LEDs 100B is activated and the LEDs generate an excitation beam that passes through the pair of 555 nm, low pass filters 204, reflects off of the 555 nm, low pass reflector 211, reflects off of the 527 nm high pass reflector 209, and passes through the lens 215 into the reaction chamber 10. The excitation beam from LEDs 100B is thus filtered to a wavelength range of 527 to 555 nm, corresponding to the peak excitation range for TAMRA. As shown in FIG. 8, emitted light from the chamber 10 then passes through the lens 232 of the detection assembly 48 and strikes the 565 nm low pass reflector 229. The portion of the light having a wavelength in the range of about 565 to 605 nm (corresponding to the peak emission wavelength range of TAMRA) passes through the 565 nm low pass reflector 229, through the 605 nm high pass reflector 227, through the pair of 565 nm high pass filters 225, through the lens 242, through the 570 nm Schott Glass® filter 222C, and is detected by the third detector 102C. The third detector 102C outputs a corresponding signal that is converted to a digital value and recorded.

Next, as shown in FIG. 6, the pair of blue LEDs 100C is activated and the LEDs generate an excitation beam that passes through the pair of 495 nm low pass filters 205, through the 495 nm high pass reflector 208, through the 527 nm high pass reflector 209, and through the lens 215 into the reaction chamber 10. The excitation beam from LEDs 100C is thus filtered to a wavelength range of about 450 to 495 nm corresponding to the peak excitation range for FAM. As shown in FIG. 8, emitted light from the chamber 10 then passes through the lens 232 of the detection assembly 48 and strikes the 565 nm low pass reflector 229. The portion of the light having a wavelength in the range of about 505 to 537 nm (corresponding to the peak emission wavelength range of FAM) reflects from the 565 nm low pass reflector 229, passes through the 537 nm high pass reflector 230, reflects from the 505 nm high pass reflector 231, passes through the pair of 505 nm high pass filters 223, through the lens 242, through the 515 nm Schott Glass® filter 222A, and is detected by the first detector 102A. The first detector 102A outputs a corresponding signal that is converted to a digital value and recorded.

Next, as shown in FIG. 6, the fourth pair of LEDs 100D is activated and the LEDs generate an excitation beam that passes through the pair of 527 nm low pass filters 206, reflects off of the mirror 210, reflects off of the 495 nm high pass reflector 208, passes through the 527 nm high pass reflector 209, and passes through the lens 215 into the reaction chamber 10. The excitation beam from LEDs 100D is thus filtered to a wavelength range of 495 to 527 nm corresponding to the peak excitation range for TET. As shown in FIG. 8, emitted light from the chamber 10 then passes through the lens 232 of the detection assembly 48 and strikes the 565 nm low pass reflector 229. The portion of the light having a wavelength in the range of about 537 to 565 nm (corresponding to the peak emission wavelength range of TET) reflects from the 565 nm low pass reflector 229, reflects from the 537 nm high pass reflector 230, passes through the pair of 537 nm high pass filters 224, through the lens 242, through the 550 nm Schott Glass® filter 222B, and is detected by the second detector 102B. The second detector 102D outputs a corresponding signal that is converted to a digital value and recorded. The total time required to activate each of the four LEDs in sequence and to collect four corresponding detector measurements is typically five seconds or less.

The spectrum of the fluorescence that is emitted by the dyes used for detection is quite broad. As a result, when an individual dye (e.g., FAM, TAMRA, TET, or ROX) emits fluorescence from the reaction vessel, the fluorescence can be detected in several of the primary detection channels, i.e. several of the detectors 102A, 102B, 102C, and 102D detect the fluorescence and generate an output signal. However, each dye has its own 'signature', i.e. the ratios of the optical signals in each detection channel are unique to each dye. It is also a reasonable assumption that the fluorescent emission from a mixture of dyes are simply additive in each of the detection channels, so that the individual dye concentrations of a dye mixture can be extracted from the mixed signals using linear algebra.

In the preferred embodiment, the controller is programmed to convert the output signals of the detectors to values indicating the true concentration of each dye in the reaction mixture using linear algebra and a calibration matrix. A preferred method for developing the calibration matrix will now be described using the four-channel system of the preferred embodiment as an example.

First, a reaction vessel containing only reaction buffer is optically read using optics assemblies 46, 48. The reaction buffer should be a fluid similar or nearly identical to the reaction mixtures that will be optically read by the optics assemblies during actual production use of the system to test samples. The reaction buffer should contain no dyes, so that the concentrations of all dyes are zero. The optical reading of the reaction buffer in the four primary detection channels produces four output signals that are converted to corresponding digital values. These four numbers are called Buffer(I), where 'I' is 1, 2, 3 or 4 depending upon which detection channel is read. The buffer values are a measure of the background signal or scattered light detected in each primary detection channel without any added fluorescent signal from dyes.

Next, a reaction mixture containing a known concentration, e.g. 100 nM, of dye #1 is placed into the vessel and again the four channels are read. The four numbers produced are called Rawdye(I, 1). Similar sets of four numbers are obtained for the other three dyes to obtain Rawdye(I, 2), Rawdye(I, 3), and Rawdye(I, 4). The buffer values are then subtracted from the raw dye values to obtain net dye values as follows:

Netdye($I$, $J$)=Rawdye($I$, $J$)−Buffer ($I$); ($I$=1 to 4)

where I indicates the detection channel, and J indicates the dye number.

The matrix Netdye(I, J) is then inverted using standard numerical methods (such as Gaussian elimination) to obtain a new matrix called the calibration matrix, Cal (I,J). Note that the matrix product of Netdye(I, J) * Cal (I,J) is the unity matrix. Now, any reaction mixture can be read and the output signals of the detectors in the four detection channels converted to values representative of the true concentrations of the dyes in the mixture. The optical reading of the mixture produces four numbers called RawMix(I). The reaction buffer values are then subtracted from the raw mix values to obtain four numbers called Mix(I) as follows:

$$\text{Mix}(I) = \text{RawMix}(I) - \text{Buffer}(I)$$

Next, the true concentrations of the dyes are obtained by matrix multiplication as follows:

$$\text{Truedye}(I) = 100 \text{ nM} * \text{Cal}(I, J) * \text{Mix}(I)$$

In the above equation, the factor of 100 comes from the fact that a concentration of 100 nM was used for the initial calibration measurements. The concentration of 100 nM is used for purposes of example only and is not intended to limit the scope of the invention. In general, the dye concentrations for calibration measurements should be somewhere in the range of 25 to 1,000 nM depending upon the fluorescent efficiency (strength) of the dyes.

Referring again to FIGS. 12–13, the matrices Cal(I, J) and Buffer(I) are preferably produced during the manufacture of each heat-exchanging module 37 and stored in the memory 114. When the module 37 is plugged into the base instrument 66, the control software application in the base instrument or external computer reads the matrices into memory and uses the matrices to convert the output signals of the detectors 102 to values indicating the concentration of each dye in the reaction mixture. Because the calibration matrices Cal(I, J) and Buffer(I) are dependent upon the particular set of dyes calibrated and the volume of the reaction vessel, it is also preferred to produce and store multiple sets of the matrices for various combinations of dye sets and reaction vessel volumes. This gives the end user greater flexibility in using the system.

As one example, calibration matrices could be stored for three different dye sets to be used with three different sizes of reaction vessels (e.g., 25 μl, 50 μl, 100 μl) for a total of nine different sets of calibration matrices. Of course, this is just one example, and many other combinations will be apparent to one skilled in the art. Further, in alternative embodiments, the control software may include functionality to guide the end user through the calibration procedure to enable the user to store and use calibration data for his or her own desired combination of dyes and reaction vessel size.

In the operation of the preferred embodiment described above, only the four primary detection channels are read to produce four output signals that are deconvolved or converted to dye concentration values representative of the concentrations of individual dyes in the reaction mixture. In another embodiment, however, one or more alternate detection channels is used to provide data for correcting potential variances in the output signals of the detectors caused by, e.g., air bubbles in the reaction vessel, variances in the shape of the vessel, or slight variances in the position of the vessel between the thermal plates. Any of these variances could potentially cause the background signal or scattered light that is detected by each detector to be different than the background or scattered light detected when generating the buffer values in the matrix Buffer(I). To correct for these variances, the controller is programmed to receive calibration signal(s) from one or more detectors using alternate (non-primary) detection channel(s) and to adjust subsequent output signals received from the primary detection channels in dependence upon the calibration signals received. The controller may be programmed to adjust the output signals received from the primary detection channels in this manner as follows.

Referring again to FIGS. 6 and 8, calibration data is generated using a LED/detector pair in which the LED generates excitation beams in an excitation wavelength range that overlaps the emission wavelength range detected by the detector. For example, the pair of green LEDs 100D and the first detector 102A are suitable for this purpose since the excitation beams from the green LEDs 100D are filtered to a wavelength range of 495 to 527 nm and the detector 102A detects emitted light in the overlapping wavelength range of 505 to 537 nm. To generate calibration data, a reaction vessel containing reaction buffer is optically interrogated using the LEDs 100D and the detector 102A. The LEDs 100D are activated and the detector 102A generates a corresponding output signal that is converted to a digital value and recorded.

To avoid overloading the detector 102A, the brightness of the LEDs 100D should be significantly reduced from their normal operating brightness during this calibration. This may be accomplished by reducing the amount of current supplied to the LEDs by the variable current source (previously described with reference to FIG. 13). The LEDs are typically supplied with 1 to 5 mA of current during this calibration procedure to avoid overloading the detector. This calibration procedure is preferably repeated a number of times with the selected LED/detector pair and may optionally be repeated with other LED/detector pairs in which the LED generates excitation beams in an excitation wavelength range that overlaps the emission wavelength range detected by the detector. A nominal scatter value $S_N$ is then calculated as the average value of the output signals of the detector (s).

Referring again to FIGS. 12–13, the nominal scatter value $S_N$ is preferably produced during the manufacture of each heat-exchanging module 37 and stored in the memory 114. When the module 37 is plugged into the base instrument 66, the control software application in the base instrument or external computer reads the scatter value $S_N$ into memory and uses the value to correct the output signals of the primary detection channels as follows. Referring again to FIGS. 6 and 8, prior to reading the primary detection channels as described in the preferred embodiment, the controller optically interrogates the reaction mixture using the same alternate channel LED/detector pair(s) used to develop the nominal scatter value $S_N$. As described above, the LEDs should be activated with a significantly reduced amount of current (e.g., 1 to 5 mA) to avoid detector overload. Reducing the current provided to the detector(s) also effectively prevents the emission of any fluorescent signal from the reaction vessel so that the output signals from the detector(s) are an accurate indicator of background or scattered light from the vessel. These calibration signal(s) from the one or more detectors are then averaged to obtain an actual scatter value $S_A$.

Following the generation of the actual scatter value $S_A$, the four primary detection channels are read as described in the preferred embodiment above to obtain the four raw mix values RawMix(I). These raw mix values are then adjusted by the ratio of the actual scatter value $S_A$ to the nominal scatter value $S_N$ ($S_A/S_N$) to correct for variances in background or scatter light due to, e.g., variances in the shape or position of the reaction vessel or air bubbles in the reaction mixture. This is preferably accomplished by multiplying the buffer values Buffer(I) by the ratio of the actual scatter value $S_A$ to the nominal scatter value $S_N$ to produce adjusted buffer values AdjBuffer(I) as follows:

$$\text{AdjBuffer}(I) = (S_A/S_N) * \text{Buffer}(I)$$

The adjusted buffer values are then subtracted from the raw mix values to obtain four numbers called Mix(I) as follows:

$$\text{Mix}(I) = \text{RawMix}(I) - \text{AdjBuffer}(I)$$

Next, as previously described in the preferred embodiment, the true concentrations of the dyes are obtained by matrix multiplication as follows:

$$\text{Truedye}(I) = 100 \text{ nM} * \text{Cal}(I, J) * \text{Mix}(I)$$

Alternatively, the scatter values $S_A$ and $S_N$ may be used to adjust the output signals of the primary detection channels in other ways, e.g., by multiplying the output values by the ratio of the actual scatter value $S_A$ to the nominal scatter value $S_N$.

Referring again to FIG. 20, following optical detection, the controller proceeds to step 436. In step 436, the controller determines if the profile is complete, e.g., if all of the thermal cycles have been completed. The controller may also be programmed to determine that the profile is complete if suitable dye concentration(s) are optically detected, indicating the presence of the target analyte(s) in the reaction mixture. If the profile is determined to be complete, the profile run ends. If not, then the controller returns to step 420, polling the actual temperature of the thermal plates, and the loop re-executes until the profile is complete.

It is presently preferred to perform an optical reading of the reaction mixture once per thermal cycle at the lowest temperature in the cycle. Alternatively, the reaction mixture could be optically monitored more frequently or less frequently as desired by the user. One advantage to frequent optical monitoring is that real-time optical data may be used to indicate the progress of the reaction. For example, when a particular predetermined fluorescent threshold is detected in a reaction mixture in a heat-exchanging module, then the temperature cycling for that module may be stopped. Furthermore, optical detection of dye activation, e.g., color change, is useful to control the cycle parameters, not only thermal schedules, but also the state or condition of reactants and products, and quantitative production. Multiple emission wavelengths can be sampled to determine, for example, progression of the reaction, end points, triggers for reagent addition, denaturation (melting), annealing and the like. The data obtained in the real-time monitoring method may be fed back to the controller to alter or adjust the optical "read" parameters. Examples of the optical read parameters include: length of read; power input or frequency to the LEDs; which wavelength should be monitored and when; and the like.

One advantage of the optical system of the preferred embodiment is that it provides excitation light to each reaction mixture in multiple, distinct excitation wavelength ranges. This ensures that the optimal excitation wavelength range is provided for each of a plurality of different fluorescently-labeled analytes in the mixture. In a typical implementation of the four-channel system, three of the optical channels are used to detect target analytes (e.g., amplified nucleic acid sequences) while the fourth channel is used to monitor an internal control to check the performance of the system. For example, beta actin is often used as an internal control in nucleic acid amplification reactions because it has a predictable amplification response and can be easily labeled and monitored to verify that the amplification is occurring properly.

In another possible implementation of the four-channel system, two of the optical channels are utilized to detect target analytes, one of the channels is used to monitor an internal control as described above, and the fourth channel is used to monitor a passive normalizer. The passive normalizer is simply a dye that is placed in a reaction mixture in a known concentration and in a free form so that it will not label any analyte. For example, ROX in a concentration of 100 to 500 nM makes a suitable normalizer. The concentration of the normalizer is monitored throughout the reaction and used to normalize the optical data collected from the other three optical channels. If the calculated concentration of the passive normalizer changes due to evaporation, variances in reaction vessel shapes, or air bubbles in the vessel, the data generated in the other three optical channels is normalized for these variances.

Another advantage of placing a passive dye in the reaction mixture is that the fluorescent signal from the dye may be used to monitor a number of different reaction parameters. Examples of these parameters include the pH, ionic strength, and temperature of the reaction mixture. The optical signal, such as absorption or fluorescence, received from the dye varies with these parameters so that the passive dye may be used to provide real-time data about these reaction parameters.

Although it is presently preferred to use the optical excitation and detection assemblies 46, 48 in conjunction with the heat-exchanging module 37 (shown in FIG. 4), it is to be understood that the optics assemblies may also be used alone to optically interrogate a reaction mixture. For example, in one alternative embodiment, the optics assemblies are incorporated in a hand-held apparatus having a slot for receiving a reaction vessel. As in the heat-exchanging module 37 of the preferred embodiment, the optics assemblies are positioned next to the slot so that when the vessel is placed in the slot, the optical excitation and detection assemblies are placed in optical communication with first and second optically transmissive walls of the vessel, respectively. Such an apparatus may resemble the heat-exchanging module 37 without the heating and cooling elements.

Figure 21:
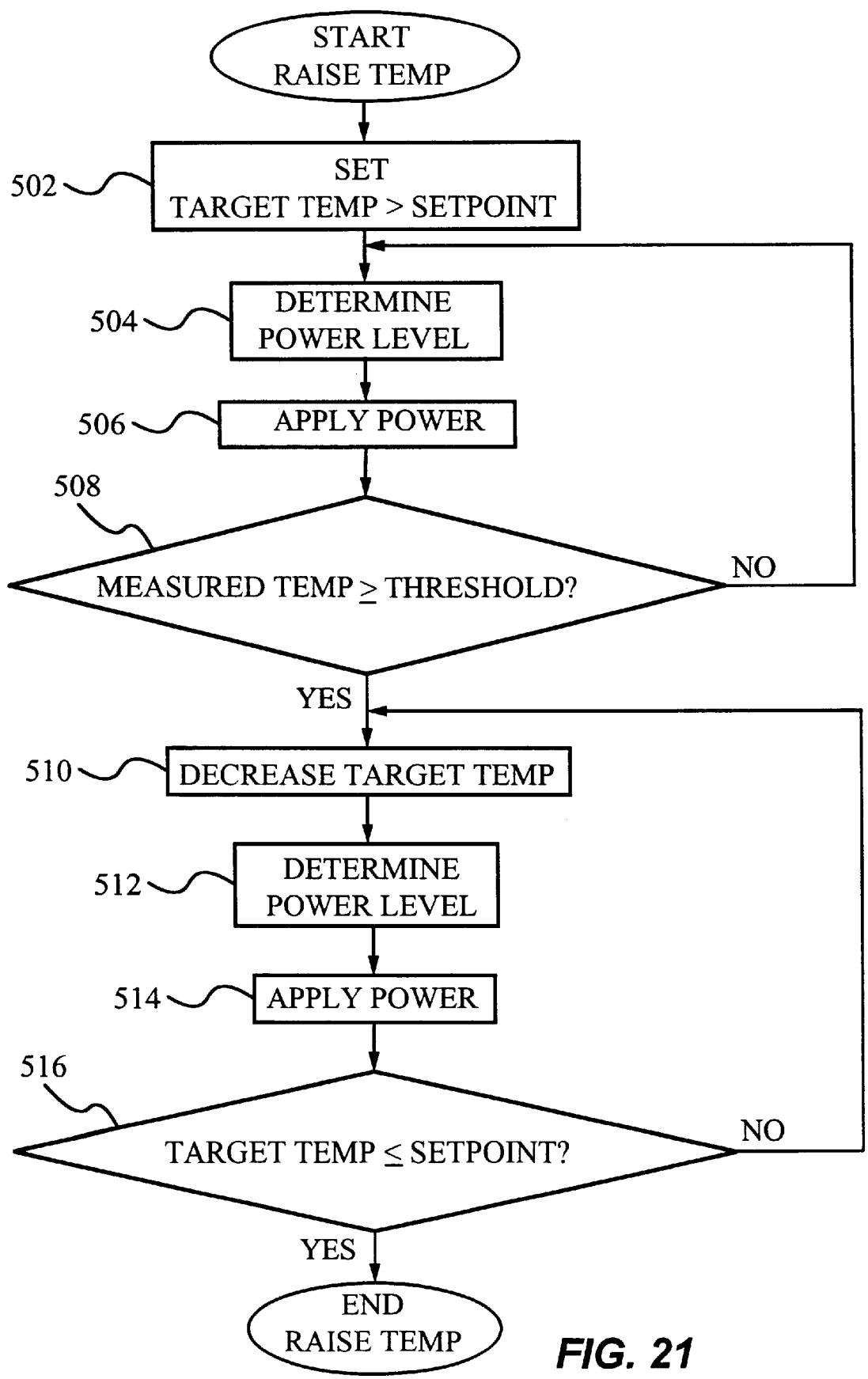
FIG. 21 is a flow diagram showing the steps for raising the temperature of a reaction mixture according to a preferred embodiment of the invention.
Figure 22:
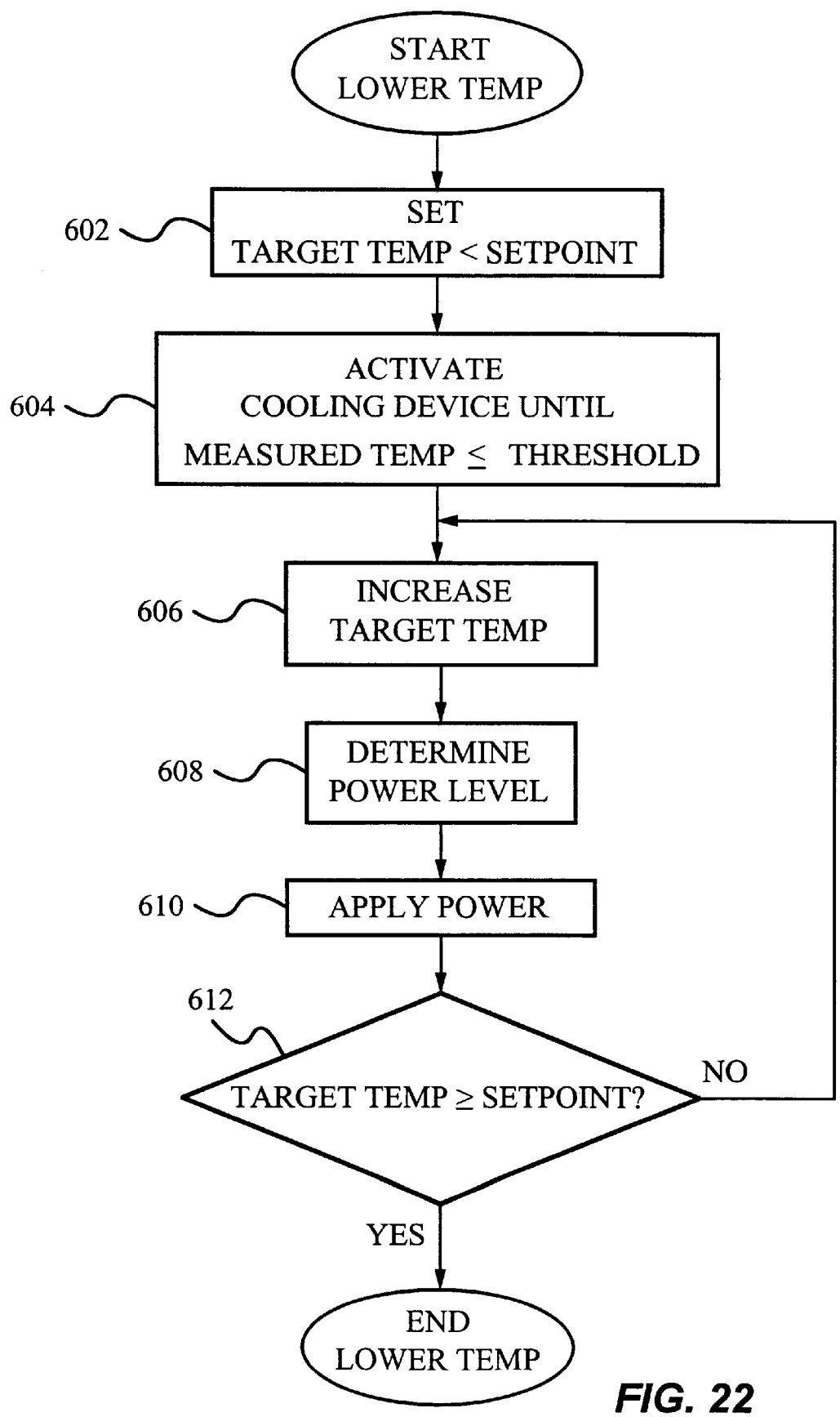
FIG. 22 is a flow diagram showing the steps for lowering the temperature of a reaction mixture according to the preferred embodiment of the invention.

FIGS. 21–22 illustrate an important improvement to computer-implemented PID control for thermally controlling the reaction mixtures in the reactor system of the present invention. In the preferred embodiment, the controller is programmed to compensate for thermal lag between a thermal plate and a reaction mixture contained in a reaction vessel. The thermal lag is caused by the need for heat to transfer from the plate through a wall of the vessel and into the reaction mixture during heating, or by the need for heat to transfer from the reaction mixture through the wall of the vessel to the plate and/or ambient atmosphere during cooling.

In standard PID control, the power supplied to a heater is dependent upon the difference (error) between the actual measured temperature of a device and the desired setpoint temperature. The average power being supplied either to the heater or the fan therefore decreases as the actual temperature of the plates approaches the setpoint temperature. Because the power being supplied to the heater or fan decreases prior to reaching the setpoint temperature, the reaction mixture does not reach the setpoint temperature as rapidly as possible. This temperature lag may cause unwanted side reactions, the formation of unwanted bubbles, the degradation of reaction components at certain temperatures, etc.

FIGS. 21–22 show the steps in an improved PID control program used in the preferred embodiment. FIG. 21 illustrates the steps performed to raise the temperature of a reaction mixture. In step 502, the controller sets a variable target temperature that initially exceeds the desired setpoint temperature. For example, if the setpoint temperature is 95° C., the initial value of the variable target temperature may be set 2 to 10° C. higher.

In step 504, the controller determines a level of power to be supplied to the heating elements to raise the temperature of the plates to the variable target temperature. The controller determines the level of power by inputting the variable target temperature to a standard PID control algorithm. The level of power to be supplied to the heaters is therefore determined in dependence upon the difference (error) between the actual plate temperature and a target temperature that is higher than the desired setpoint temperature. The higher target temperature ensures that a higher level of power is supplied to the heaters to heat the plates, and therefore the reaction mixture, to the setpoint temperature more rapidly. In step 506, the controller sends a control signal to the power and source control circuit in the base instrument to provide power to the heaters at the level determined.

In decision step 508, the controller determines if the actual measured temperature of the plates is greater than or equal to a predetermined threshold value. Suitable threshold values are: the desired setpoint temperature itself; or 1 to 2° C. below the setpoint temperature, e.g., 93 to 94° C. for a setpoint temperature of 95° C. If the actual plate temperature does not exceed the predetermined threshold value, then the controller returns to step 504 and repeats the loop until the plate temperature equals or exceeds the threshold value.

When the actual measured temperature of the plates is greater than or equal to the threshold value, the controller decreases the variable target temperature in step 510. The controller preferably decreases the variable target temperature by exponentially decaying the amount by which the variable target temperature exceeds the setpoint temperature. For example, the amount by which the variable target temperature exceeds the desired setpoint temperature may be exponentially decayed as a function of time according to the equation:

$$\Delta = (\Delta_{max}) * e(-t/\text{tau})$$

where $\Delta$ is equal to the amount by which the variable target temperature exceeds the desired setpoint temperature, $\Delta$max is equal to the difference between the initial value of the variable target temperature and the desired setpoint temperature, t is equal to the elapsed time in tenths of seconds from the start of decay, and tau is equal to a decay time constant. In the system of the present invention, tau preferably has a value in the range of 1 to 4 seconds. It is presently preferred to determine tau empirically for each heat-exchanging module during testing and calibration and to store the value of tau in the module's memory 114 (FIG. 13).

Although the exponential equation given above is presently preferred, it is to be understood that many other exponential decay formulas may be employed and fall within the scope of the invention. Moreover, the variable target temperature may be decreased by other techniques, e.g., it may be decreased linearly.

In step 512, the controller determines a new level of power to be supplied to the heating elements to raise the temperature of the plates to the decreased target temperature. The controller determines the level of power by inputting the decreased target temperature to the PID control algorithm. In step 514, the controller sends a control signal to the power and source control circuit in the base instrument to provide power to the heaters at the new level determined.

In decision step 516, the controller determines if the variable target temperature is less than or equal to the setpoint temperature. If it is not, the controller returns to step 510, decreasing the target temperature, and the loop continues until the variable target temperature is less than or equal to the setpoint temperature. When the variable target temperature is less than or equal to the setpoint temperature, the raise-temperature routine ends and standard PID control is resumed.

FIG. 22 is a flow diagram illustrating the steps performed by the controller to lower the temperature of a reaction mixture to a desired setpoint temperature. In step 602, the controller sets a variable target temperature that is initially lower than the desired setpoint temperature. For example, if the setpoint temperature is 60° C., the initial value of the variable target temperature may be set 2 to 10° C. lower, i.e., 50 to 58° C.

In step 604, the controller activates the fan until the actual measured temperature of the plates is less than or equal to a threshold value, preferably the variable target temperature. In step 606, the controller deactivates the fan and increases the target temperature, preferably by exponentially decaying the amount by which the variable target temperature differs from the setpoint temperature using the exponential decay equation given above. For cooling, tau is preferably in the range of 1 to 5 seconds with a preferred value of about 3 seconds. As in the heating example given above, tau may be determined empirically for each heat-exchanging module during testing or calibration and stored in the module's memory. Alternatively, the variable target temperature may be linearly increased.

In step 608, the controller determines a level of power to be supplied to the heating elements to raise the temperature of the plates to the increased target temperature. The controller determines the level of power by inputting the increased target temperature to the PID control algorithm. In step 610, the controller sends a control signal to the power and source control circuit in the base instrument to provide power to the heaters at the level determined.

In decision step 612, the controller determines if the variable target temperature is greater than or equal to the setpoint temperature. If it is not, the controller returns to step 606, increasing the target temperature, and the loop continues until the variable target temperature is greater than or equal to the setpoint temperature. When the variable target temperature is greater than or equal to the setpoint temperature, the lower-temperature routine ends and steady-state PID control begins.

Figure 23A:
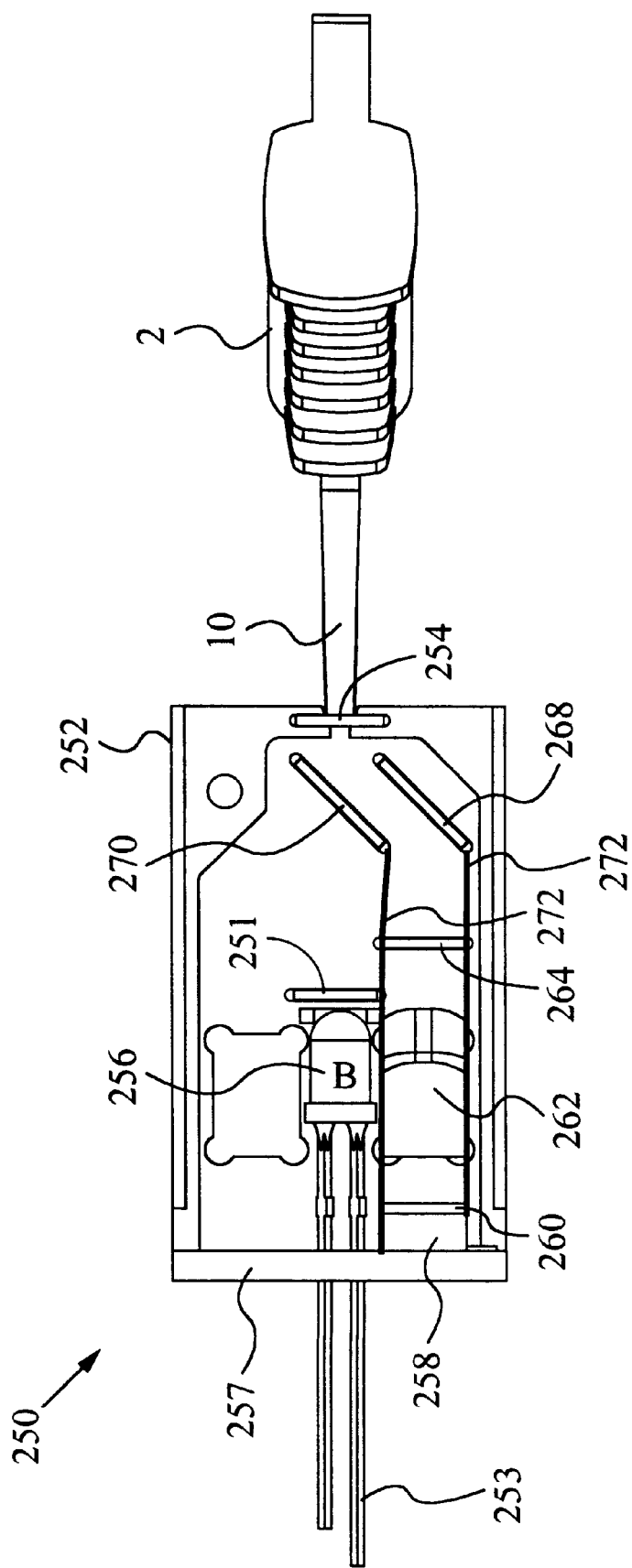
FIGS. 23A–23B are schematic, plan views of a pair of optics assemblies for use in the module of FIG. 4 according to a second embodiment of the invention.
Figure 23B:
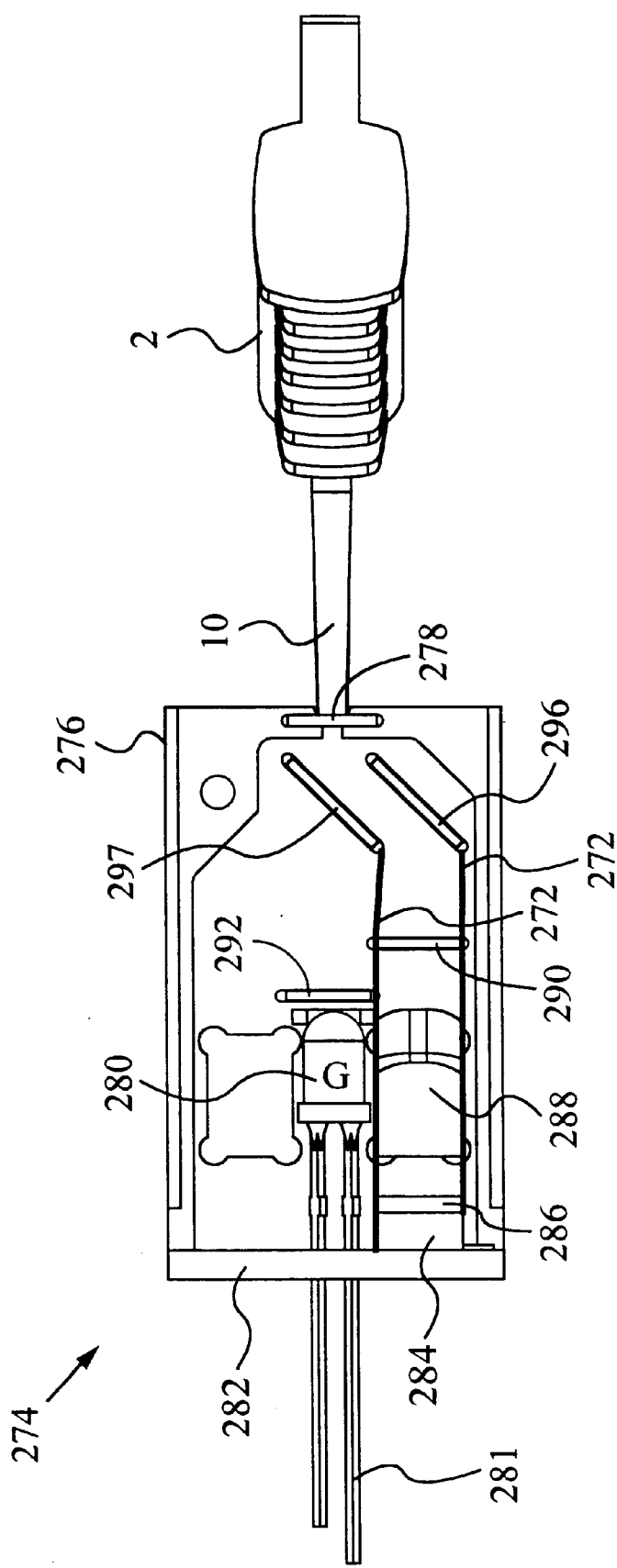

Referring again to FIG. 4, in the preferred embodiment, each heat-exchanging module 37 includes a pair of optics assemblies 46, 48 in which all of the light sources are positioned in the first optics assembly 46 and all of the detectors are positioned in the second optics assembly 48. It is also possible, however, to include both one or more light sources and one or more detectors in each of the optics assemblies. FIGS. 23A–23B illustrate a pair of optics assemblies according to a second embodiment of the invention in which each optics assembly includes a light source for exciting a labeled analyte in a reaction mixture and a detector for detecting light emitted from the mixture.

FIG. 23A shows a schematic plan view of a first optics assembly 250 according to the second embodiment. The assembly 250 is positioned adjacent the reaction vessel 2 to transmit excitation beams to the reaction mixture contained in the chamber 10. The assembly 250 includes a housing 252 for holding various components of the assembly. The housing 252 preferably comprises one or more molded pieces of plastic. The housing 252 is preferably a two-piece housing comprised of complementary bottom and top pieces that are coupled together using, e.g., fasteners such as screws or bolts. In the view of FIG. 23A the top piece of the housing is removed to show the internal components of the optics assembly 250. In alternative embodiments, the housing 252 may be a one-piece housing that holds a slide-in optics package.

The housing 252 includes an optical window 254. In general, the optical window 254 may simply comprise an opening in the housing through which light may be transmitted. The optical window 254 may optionally include an optically transmissive or transparent piece of glass or plastic serving as a window pane, or a lens as in the preferred embodiment.

The optics assembly 250 also includes a light source, preferably a blue LED 256, for transmitting excitation beams to the chamber 10 through the window 254. The LED 256 receives power through leads 253 which are connected to an adjustable current source (not shown in FIG. 23A). The LED 256 is mounted to an optical circuit board 257 which is secured to the back of the housing 252 so that the LED 256 is rigidly fixed in the housing 252. The optical circuit board 257 may be secured to the housing 252 using fasteners such as screws, bolts, glued-in plugs, or the like. A detector 258, preferably a PIN photodiode, is also mounted to the optical circuit board 257 and rigidly fixed in the housing 252. As in the preferred embodiment, the optical circuit board is preferably connected to the main PC board 54 of the heat-exchanging module 37 (shown in FIG. 4) via a flex cable.

The optics assembly 250 further includes filters and lenses arranged in the housing 252 for filtering excitation beams generated by the LED 256, for filtering light emitted from the chamber 10, and for directing the emitted light to the detector 258. The housing 252 preferably includes recesses or slots for receiving and rigidly holding the filters and lenses. The filters and lenses may also be rigidly fixed in the housing 252 by means of an adhesive used alone, or more preferably, with an adhesive used in combination with slots in the housing.

In general, the filters in the optics assembly 250 may be selected to provide excitation beams to the reaction mixture in the chamber 10 in any desired excitation wavelength range and to block light emitted from the chamber 10 outside of any desired emission wavelength range. The optics assembly 250 may therefore be used with any fluorescent, phosphorescent, chemiluminescent, or electrochemiluminescent labels of interest. For purposes of illustration, one specific embodiment of the assembly 250 will now be described in which the assembly 250 is designed to provide excitation beams in the peak excitation wavelength range of FAM and to detect light emitted from the chamber 10 in the peak emission wavelength range of TAMRA.

In this embodiment, two 590 nm bandpass filters 260 and 264 are positioned between the detector 258 and the window 254 for blocking light emitted from the chamber 10 outside of an emission wavelength range of about 575 to 605 nm. A lens 262 is positioned between the filters 260 and 264 for collimating and focusing light to the detector 258. The optics assembly 250 also includes a 570 nm high pass reflector 268 and a 500 nm high pass reflector 270. The reflectors 268, 270 are angularly offset 45° from the bandpass filters 260, 264. A lens 251 may optionally be positioned in front of the LED 256 to focus and collimate excitation beams from the LED. If the LED 256 is a directional LED, as is presently preferred, the lens 251 is not required. The optics assembly 250 also includes dividers 272, preferably black polycarbonate sheets, for keeping excitation beams from the LED 256 away from the detector 258.

FIG. 23B shows a schematic plan view of a second optics assembly 274 complementary to the first optics assembly 250. The assembly 274 includes a housing 276 that preferably comprises one or more molded pieces of plastic. The housing 276 is preferably a two-piece housing comprising complementary bottom and top pieces that are coupled together using, e.g., fasteners such as screws or bolts. In the view of FIG. 23B, the top piece of the housing is removed to show the internal components of the assembly 274. In alternative embodiments, the housing 276 may be a one-piece housing that holds a slide-in optics package.

The housing 276 includes an optical window 278. In general, the optical window 278 may simply comprise an opening in the housing through which light may be transmitted. The optical window 278 may optionally include an optically transmissive or transparent piece of glass or plastic serving as a window pane, or a lens as in the preferred embodiment.

The optics assembly 274 also includes a light source, preferably a green LED 280, for transmitting excitation beams to the chamber 10 through the window 278. The LED 280 receives power through leads 281 which are connected to an adjustable current source (not shown in FIG. 23B). The LED 280 is mounted to an optical circuit board 282 which is secured to the back of the housing 276 so that the LED 280 is rigidly fixed in the housing 276. The optical circuit board 282 may be secured to the housing 276 using fasteners such as screws, glued in plugs, or the like. A detector 284, preferably a PIN photodiode, is also mounted to the optical circuit board 282 and rigidly fixed in the housing 276. As in the preferred embodiment, the optical circuit board is preferably connected to the main PC board 54 of the heat-exchanging module 37 (shown in FIG. 4) via a flex cable.

The optics assembly 274 further includes filters and lenses arranged in the housing 276 for filtering excitation beams generated by the LED 280, for filtering light emitted from the chamber 10, and for directing the emitted light to the detector 284. The housing 276 preferably includes recesses or slots for receiving and rigidly holding the filters and lenses. The filters and lenses may also be rigidly fixed in the housing by means of an adhesive used alone, or more preferably, with an adhesive used in combination with slots in the housing.

In general, the filters in the optics assembly 276 may be selected to provide excitation beams to the reaction mixture in the chamber 10 in any desired excitation wavelength range and to block light emitted from the chamber 10 outside of any desired emission wavelength range. For purposes of illustration, one specific embodiment of the assembly 274 will now be described in which the assembly 274 is designed to provide excitation beams in the peak excitation wavelength range of TAMRA and to detect light emitted from the chamber 10 in the peak emission wavelength range of FAM.

In this embodiment, two 525nm bandpass filters 286 and 290 are positioned between the detector 284 and the window 278 for blocking light emitted from the chamber 10 outside of an emission wavelength range of about 510 to 540 nm. A lens 288 is positioned between the filters 286 and 290 for collimating and focusing light to the detector 284. The optics assembly 274 also includes a 500 nm high pass reflector 296, a 50/50 beamsplitter 297, and a 525 nm bandpass filter 292.

The reflector 296 and beamsplitter 297 are angularly offset 45° from the bandpass filters 286, 290. The optics assembly 274 also includes dividers 272, preferably black polycarbonate sheets, for keeping excitation beams from the LED 280 away from the detector 284.

In operation, the pair of optics assemblies 250, 274 are used to optically interrogate a reaction mixture in the chamber 10 as follows. As shown in FIG. 23A, the blue LED 256 is activated and the LED generates an excitation beam that passes through the 500 nm high pass reflector 270, through the window 254, and into the reaction chamber 10. The excitation beam from the LED 256 is thus filtered to a wavelength range below 500 nm corresponding to the excitation range for FAM.

As shown in FIG. 23B, emitted light (e.g., fluorescence radiation from the FAM dye) is transmitted from the chamber 10 through the window 278 of the optics assembly 274 and strikes the beamsplitter 297. A portion of the emitted light reflects from the beamsplitter 297 to the 500 nm high pass reflector 296. The portion of the emitted light having a wavelength in the range of about 510 to 540 nm (corresponding to the peak emission wavelength range of FAM) reflects from the 500 nm high pass reflector 296, passes through the 525 nm bandpass filter 290, through the lens 288, through the 525 nm bandpass filter 286, and is detected by the detector 284. The detector 284 outputs a corresponding signal that is converted to a digital value and recorded.

Next, the green LED 280 is activated and the LED generates an excitation beam that passes through the 525 nm bandpass filter 292, through the beamsplitter 297, through the window 278, and into the reaction chamber 10. The excitation beam from the LED 280 is thus filtered to a wavelength range of about 510 to 540 nm corresponding to the excitation range for TAMRA.

As shown in FIG. 23A, emitted light (e.g., fluorescence radiation from the TAMRA dye) is transmitted from the chamber 10 through the window 254 of the optics assembly 252 and strikes the 500 nm high pass reflector 270. The portion of the emitted light having a wavelength in the range of 575 to 605 nm (corresponding to the peak emission wavelength range of TAMRA) reflects from the 500 nm high pass reflector 270, reflects from 570 nm high pass reflector 268, passes through the 590 nm bandpass filter 264, through the lens 262, through the 590 nm bandpass filter 260, and is detected by the detector 258. The detector 258 outputs a corresponding signal that is converted to a digital value and recorded.

The remaining operation of the second embodiment is analogous to the operation of the preferred embodiment described above. The output signals of the detectors may be converted to values indicating the true concentration of each dye in the reaction mixture using linear algebra and calibration matrices (in this embodiment two-row calibration matrices rather than the four-row matrices of the preferred embodiment). If the emission spectra of the two dyes used for detection are sufficiently distinct, however, deconvolution of the optical data using linear algebra is not necessary. For example, FAM and TAMRA usually have sufficiently distinct emission spectra. One advantage of the optics assemblies 250, 274 of the second embodiment is that they can be made smaller and more compact than the assemblies of the preferred embodiment.

Figure 24A:
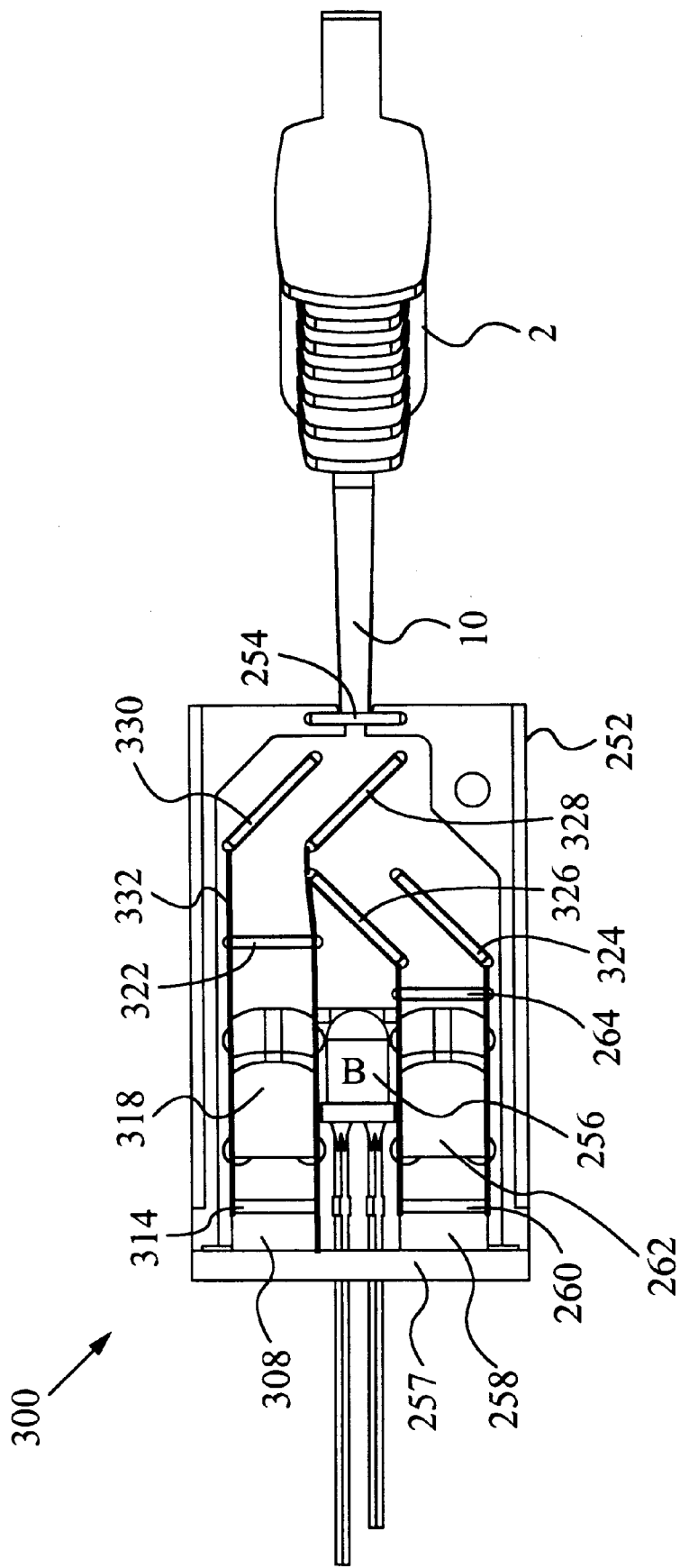
FIGS. 24A–24B are schematic, plan views of another pair of optics assemblies for use in the module of FIG. 4 according to a third embodiment of the invention.
Figure 24B:
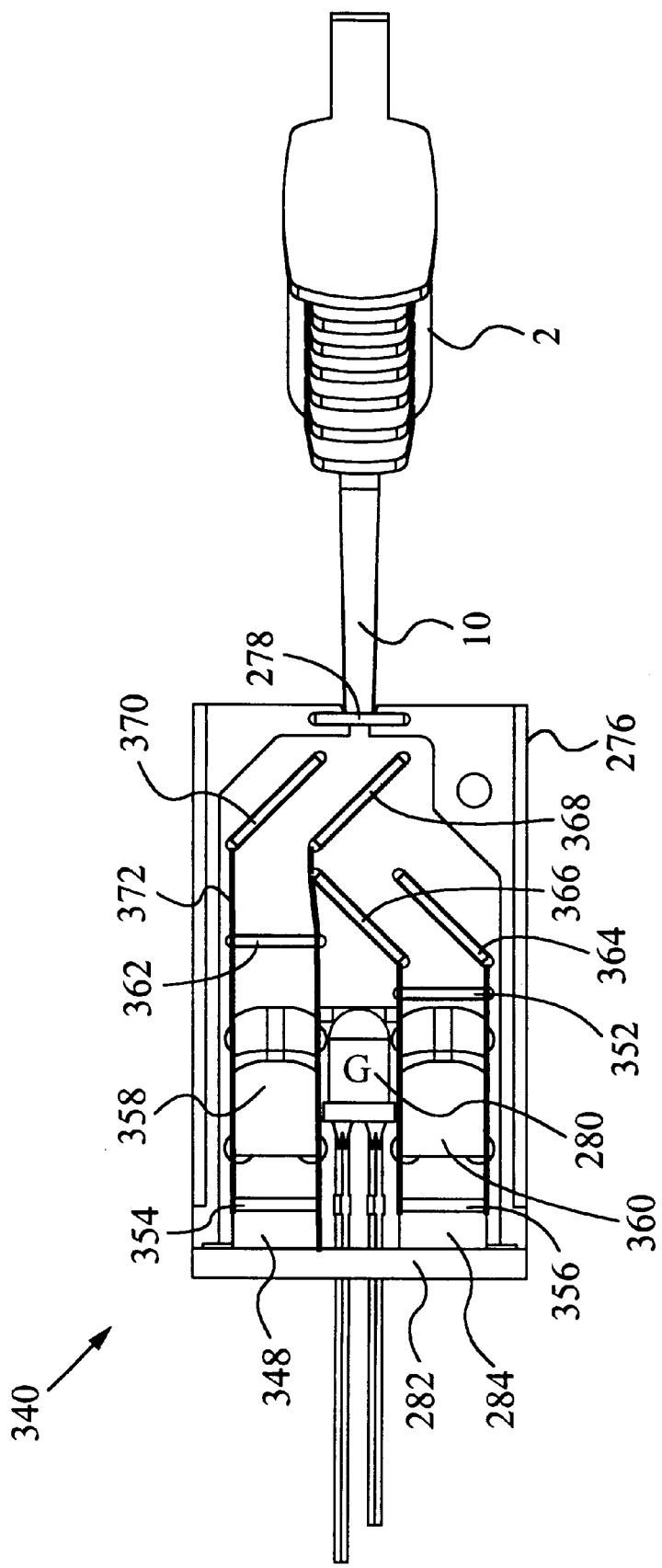

FIGS. 24A–24B illustrate a pair of optics assemblies 300, 340 according to a third embodiment of the invention. The optics assemblies 300, 340 of the third embodiment are similar to the optics assemblies of the second embodiment, except that optics assemblies 300, 340 each include an additional detector and additional filters to enable detection of up to four differently labeled analytes in a reaction mixture.

FIG. 24A shows a schematic plan view of the first optics assembly 300 according to the third embodiment. The optics assembly 300 includes many of the same parts as the first optics assembly 250 (FIG. 23A) of the second embodiment previously described above. These parts are labeled with the same reference numerals in FIG. 24A. In addition to these parts, the assembly 300 includes an additional detector 308, preferably a PIN photodiode, which is mounted to the optical circuit board 257 and rigidly fixed in the housing 252.

The optics assembly 300 further includes filters and lenses arranged in the housing 252 for filtering excitation beams generated by the LED 256, for separating light emitted from the chamber 10 into two different emission wavelength ranges, and for directing the emitted light in each of the emission wavelength ranges to a respective one of the detectors 258, 308. In general, the filters in the optics assembly 300 may be selected to provide excitation beams to the reaction mixture in the chamber 10 in any desired excitation wavelength range and to block light emitted from the chamber 10 outside of any desired emission wavelength ranges. The optics assembly 300 may therefore be used with any fluorescent, phosphorescent, chemiluminescent, or electrochemiluminescent labels of interest. For purposes of illustration, one specific embodiment of the assembly 300 will now be described in which the assembly is designed to provide excitation beams in the excitation wavelength ranges of FAM and HEX and to detect light emitted from the chamber 10 in the peak emission wavelength ranges of TAMRA and ROX.

In this embodiment, two 590 nm bandpass filters 260 and 264 are positioned between the detector 258 and the window 254 for blocking light emitted from the chamber 10 outside of an emission wavelength range of about 575 to 605 nm. A lens 262 is positioned between the filters 260 and 264 for collimating and focusing light to the detector 258. Two 600 nm high pass filters 314 and 322 are positioned between the detector 308 and the window 254. A lens 318 is positioned between the filters 314 and 322 for collimating and focusing light to the detector 308. The optics assembly 300 also includes mirrors 324 and 330, a 500 nm high pass reflector 326, and a 600 nm high pass reflector 328. The mirrors and reflectors 324, 326, 328, 330 are angularly offset 45° from the filters 260, 264, 314, 322. The optics assembly 300 also includes dividers 332, preferably black polycarbonate sheets, for keeping light generated by the LED 256 away from the detectors 258 and 308.

FIG. 24B shows a schematic plan view of the second optics assembly 340 according to the third embodiment. The optics assembly 340 includes many of the same parts as the second optics assembly 274 (FIG. 23B) of the second embodiment previously described above. These parts are labeled with the same reference numerals in FIG. 24B. In addition to these parts, the assembly 340 includes an additional detector 348, preferably a PIN photodiode, which is mounted to the optical circuit board 282 and rigidly fixed in the housing 276.

The optics assembly 340 further includes filters and lenses arranged in the housing 276 for filtering excitation beams generated by the LED 280, for separating light emitted from the chamber 10 into two different emission wavelength ranges, and for directing the emitted light in each of the emission wavelength ranges to a respective one of the detectors 284, 348. In general, the filters in the optics assembly 340 may be selected to provide excitation beams to the reaction mixture in the chamber 10 in any desired excitation wavelength range and to block light emitted from the chamber 10 outside of any desired emission wavelength ranges. The optics assembly 340 may therefore be used with any fluorescent, phosphorescent, chemiluminescent, or electrochemiluminescent labels of interest. For purposes of illustration, one specific embodiment of the assembly 340 will now be described in which the assembly is designed to provide excitation beams in the excitation wavelength ranges of TAMRA and ROX and to detect light emitted from the chamber 10 in the peak emission wavelength ranges of FAM and HEX.

In this embodiment, two 555 nm, bandpass filters 352 and 356 are positioned between the detector 284 and the window 278 for blocking light emitted from the chamber 10 outside of an emission wavelength range of about 540 to 570 nm. A lens 360 is positioned between the filters 352 and 356 for collimating and focusing light to the detector 284. Two 525 nm bandpass filters 354 and 362 are positioned between the detector 348 and the window 278 for blocking light emitted from the chamber 10 outside of an emission wavelength range of about 510 to 540 nm. A lens 358 is positioned between the filters 354 and 362 for collimating and focusing light to the detector 348. The optics assembly 340 also includes mirrors 364 and 370, a 50/50 beamsplitter 366, and a 537 nm low pass reflector 368. The mirrors and reflectors 364, 366, 368, 370 are angularly offset 45° from the filters 352, 354, 356, 362. The optics assembly 340 also includes dividers 372, preferably black polycarbonate sheets, for keeping light generated by the LED 280 away from the detectors 284 and 348.

In operation, the pair of optics assemblies 300, 340 are used to optically interrogate a reaction mixture in the chamber 10 as follows. As shown in FIG. 24A, the blue LED 256 is activated and the LED generates an excitation beam that passes through the 500 nm high pass reflector 326, through the 600 nm high pass reflector 328, through the window 254, and into the chamber 10. The excitation beam from the LED 256 is thus filtered to a wavelength range below 500 nm to excite the FAM and HEX dyes in the reaction mixture.

As shown in FIG. 24B, emitted light (e.g., fluorescence radiation from the FAM and HEX dyes) is transmitted from the chamber 10 through the window 278 of the optics assembly 340 and strikes the 537 nm low pass reflector 368. The portion of the emitted light having a wavelength in the range of 510 to 537 nm (corresponding to the peak emission wavelength range of FAM) reflects from the 537 nm low pass reflector 368, reflects from the mirror 370, passes through the 525 nm bandpass filter 362, through the lens 358, through the 525 nm bandpass filter 354, and is detected by the detector 348. The detector 348 outputs a corresponding signal that is converted to a digital value and recorded.

Meanwhile, the portion of the emitted light having a wavelength in the range of 540 to 570 nm (corresponding to the peak emission wavelength range of HEX) passes through the 537 nm low pass reflector 368, reflects from the beamsplitter 366, reflects from the mirror 364, passes through the 555 nm, bandpass filter 352, through the lens 360, through the 555 nm, bandpass filter 356, and is detected by the detector 284. The detector 284 outputs a corresponding signal that is converted to a digital value and recorded.

Next, the green LED 280 is activated and the LED generates an excitation beam that passes through the beamsplitter 366, through the 537 nm low pass reflector 368, through the window 278, and into the reaction chamber 10. The excitation beam from the LED 280 is thus filtered to a wavelength range above 537 nm to excite the TAMRA and ROX dyes in the reaction mixture.

As shown in FIG. 24A, emitted light (e.g., fluorescence radiation from the TAMRA and ROX dyes) is transmitted from the chamber 10 through the window 254 of the optics assembly 300 and strikes the 600 nm high pass reflector 328. The portion of the emitted light having a wavelength in the range of 575 to 600 nm (corresponding to the peak emission wavelength range of TAMRA) passes through the 600 nm high pass reflector 328, reflects from the 500 nm high pass reflector 326, reflects from the mirror 324, passes through the 590 nm bandpass filter 264, through the lens 262, through the 590 nm bandpass filter 260, and is detected by the detector 258. The detector 258 outputs a corresponding signal that is converted to a digital value and recorded.

Meanwhile, the portion of the emitted light having a wavelength over 600 nm (corresponding to the peak emission wavelength range of ROX) reflects from the 600 nm high pass reflector 328, reflects from the mirror 330, passes through the 600 nm high pass filter 322, through the lens 318, through the 600 nm high pass filter 314, and is detected by the detector 308. The detector 308 outputs a corresponding signal that is converted to a digital value and recorded.

The remaining operation of the third embodiment is analogous to the operation of the preferred embodiment described above. The output signals of the detectors may be converted to values indicating the true concentration of dye labeling each analyte in the reaction mixture using linear algebra and calibration matrices, as previously described. An advantage of the optics assemblies 300, 340 of the third embodiment is that they can be made smaller than the assemblies of the preferred embodiment.

Although it is presently preferred to use the optics assemblies of FIGS. 23A–23B or of FIGS. 24A–24B in conjunction with the heat-exchanging module 37 (shown in FIG. 4), it is to be understood that either pair of the optics assemblies may also be used alone to optically interrogate a reaction mixture. For example, in an alternative embodiment, a pair of the optics assemblies are incorporated in a hand-held apparatus having a slot for receiving a reaction vessel. As in the preferred embodiment, the pair of optics assemblies are positioned next to the slot so that when the vessel is placed in the slot, the optics assemblies are placed in optical communication with first and second optically transmissive walls of the vessel, respectively. Such an apparatus may resemble the heat-exchanging module 37 without the heating and cooling elements.

The various embodiments of the system of the present invention may find use in many applications. The system may be utilized to perform chemical reactions on samples, e.g., nucleic acid amplification, and to optically detect amplified target sequences. For example, samples may be mixed with a polynucleotide, a polymerase such as Taq polymerase, nucleoside triphosphates, a first primer hybridizable with the sample polynucleotide, and a second primer hybridizable with a sequence complementary to the polynucleotide. Some or all of the required reagents and dyes may be present in the reaction vessel as shipped, or they may be added to the sample and the reaction mixture delivered through the inlet port of the vessel. Alternatively, the reagents and dyes may be delivered to the reaction chamber of the vessel independently of the sample. The polymerase chain reaction may be performed according to methods well known in the art.

Although amplification by polymerase chain reaction has been described herein, it will be appreciated by persons skilled in the art that the devices and methods of the present invention may be utilized for a variety of other polynucleotide amplification reactions and ligand-binding assays. Such additional reactions may be thermally cycled or they may be carried out at a single temperature, e.g., nucleic acid sequenced-based amplification (NASBA). Moreover, such reactions may employ a wide variety of amplification reagents and enzymes, including DNA ligase, T7 RNA polymerase and/or reverse transcriptase, among others. Polynucleotide amplification reactions that may be practiced in the system of the invention include, but are not limited to: (1) target polynucleotide amplification methods such as self-sustained sequence replication (3SR) and strand-displacement amplification (SDA): (2) methods based on amplification of a signal attached to the target polynucleotide, such as "branched chain" DNA amplification; (3) methods based on amplification of probe DNA such as ligase chain reaction (LCR) and QB replicase amplification (QBR); (4) transcription-based methods, such as ligation activated transcription (LAT) and nucleic acid sequence-based amplification (NASBA); and (5) various other amplification methods, such as repair chain reaction (RCR) and cycling probe reaction (CPR). Other applications of the system are intended to be within the scope of the invention where those applications require the transfer of thermal energy to a reaction mixture and/or optical interrogation of the reaction mixture or reaction products.

SUMMARY, RAMIFICATIONS, AND SCOPE

Although the above description contains many specificities, it is to be understood that many different modifications or substitutions may be made to the systems and methods described without departing from the broad scope of the invention. For example, each heat-exchanging module or base instrument may include an electronic filter for receiving signals from the optical detectors and for rejecting any signals outside of a predetermined frequency range, e.g., 950 to 1050 Hz. In this embodiment, each light source is activated by pulsing the light source at a frequency in the predetermined range, and only the detector signals in the range are recorded. The advantage of this detection circuit is that it rejects electronic noise and slow optical drift.

The filters used in the optics assemblies may be designed to provide excitation and emission light in any wavelength ranges of interest, not just the specific wavelength ranges described above. The specific filter wavelengths described above are useful for the exemplary dyes of the preferred embodiment and are not intended to limit the scope of the invention. The choice of fluorescent dyes for any given application depends upon the analytes of interest. One skilled in the art will realize that different combinations of light sources, filters, or filter wavelengths may be used to accommodate the different peak excitation and emission spectra of the selected dyes. Moreover, although blue and green light sources are presently preferred, different color light sources, such as blue-green or amber LEDs, may be used in the system.

Further, although fluorescence excitation and emission detection is a preferred embodiment, optical detection methods such as those used in direct absorption and/or transmission with on-axis geometries may also be applied to the multi-channel detection system of the present invention. Alternative geometries, such as on-axis alignments of light sources and detectors, can be used to monitor changes in dye concentrations and physical conditions (temperature, pH, etc.) of a reaction by measuring absorption of the illumination. The system may also be used to measure time decay fluorescence. Additionally, the multi-channel detection system is not limited to detection based upon fluorescent labels. The detection system may be applicable to detection based upon phosphorescent labels, chemiluminescent labels, or electrochemiluminescent labels.

Therefore, the scope of the invention should be determined by the following claims and their legal equivalents.

What is claimed is:

1. An apparatus for optically interrogating a reaction mixture contained in a reaction vessel having a chamber for holding the mixture, the apparatus comprising:
   a) a first optics assembly comprising:
      i) at least two light sources for transmitting excitation beams to the chamber;
      ii) a first set of filters for filtering the excitation beams such that each of the beams transmitted to the chamber has a substantially distinct excitation wavelength range; and
      iii) a first housing for holding the light sources and the first set of filters, wherein the light sources and the first set of filters are rigidly fixed in the first housing; and
   b) a second optics assembly comprising:
      i) at least two detectors for detecting light emitted from the chamber in at least two respective emission wavelength ranges;
      ii) a second set of filters for separating the light emitted from the chamber into the respective emission wavelength ranges; and
      iii) a second housing for holding the detectors and the second set of filters, wherein the detectors and the second set of filters are rigidly fixed in the second housing.

2. The apparatus of claim 1, wherein the first optics assembly includes at least four light sources arranged with the first set of filters for transmitting the excitation beams in at least four excitation wavelength ranges, and wherein the second optics assembly includes at least four detectors arranged with the second set of filters for detecting the emitted light in at least four emission wavelength ranges.

3. The apparatus of claim 1, wherein the vessel includes at least first and second optically transmissive walls defining the chamber, the apparatus includes a slot for receiving the chamber of the vessel, and the first and second optics assemblies are positioned such that when the vessel is placed in the slot, the first and second optics assemblies are in optical communication with the first and second optically transmissive walls, respectively.

4. The apparatus of claim 3, further comprising:
   a) opposing plates defining the slot between them; and
   b) a heating element coupled to at least one of the plates.

5. The apparatus of claim 4, wherein the plates, heating element, and optics assemblies are incorporated into a heat-exchanging module, the apparatus further comprises a base instrument for receiving the heat-exchanging module, and the base instrument includes electronics for controlling the operation of the module.

6. The apparatus of claim 5, wherein the heat-exchanging module further comprises a housing and a cooling device disposed within the housing for cooling the reaction mixture contained in the chamber.

7. The apparatus of claim 5, wherein the base instrument is constructed to receive and control a plurality of such heat-exchanging modules.

8. The apparatus of claim 7, further comprising at least one computer for controlling the base instrument.

9. The apparatus of claim 1, wherein the first housing has at least one optical window through which the excitation beams are transmitted, and wherein the first optics assembly further comprises a lens positioned in the optical window for focusing the excitation beams.

10. The apparatus of claim 1, wherein the second housing has at least one optical window through which the light emitted from the chamber is received, and wherein the second optics assembly further comprises a lens positioned in the optical window for collimating the light emitted from the chamber.

11. The apparatus of claim 1, further comprising an adjustable power source for supplying a variable amount of power to the light sources.

12. The apparatus of claim 1, further comprising electronics for receiving signals from the detectors and for adjusting the gain or offset of the signals.

13. The apparatus of claim 1, further comprising a controller for controlling the operation of the optics assemblies.

14. The apparatus of claim 13, wherein the controller is programmed to use a calibration matrix to convert output signals from the detectors into values representative of the concentrations of dyes labeling analytes in the reaction mixture.

15. The apparatus of claim 13, wherein at least one of the excitation wavelength ranges overlaps one of the emission wavelength ranges, and wherein the controller is programmed to receive a calibration signal from the detector receiving light in the overlapped emission wavelength range and to adjust subsequent output signals received from the detectors in dependence upon the calibration signal.

16. The apparatus of claim 1, wherein the vessel includes at least first and second optically transmissive walls defining the chamber, the first and second optically transmissive walls are angularly offset from each other by about 90°, and the optics assemblies are positioned to provide about a 90° angle between the path of each excitation beam entering the vessel through the first optically transmissive wall and the path of the emitted light detected through the second optically transmissive wall.

17. An apparatus for optically interrogating a reaction mixture, the apparatus comprising:
 a) a reaction vessel having a chamber for holding the mixture, wherein the vessel includes at least first and second optically transmissive walls defining the chamber;
 b) at least two light sources for transmitting excitation beams to the reaction mixture through the first optically transmissive wall;
 c) a first set of filters for filtering the excitation beams such that each of the beams transmitted to the reaction mixture has a substantially distinct excitation wavelength range;
 d) at least two detectors for detecting light emitted from the chamber through the second optically transmissive wall; and
 e) a second set of filters for separating the light emitted from the chamber into at least two emission wavelength ranges and for directing the light in each of the emission wavelength ranges to a respective one of the detectors.

18. The apparatus of claim 17, wherein the apparatus includes:
 a) at least four light sources arranged with the first set of filters for transmitting the excitation beams in at least four excitation wavelength ranges; and
 b) at least four detectors arranged with the second set of filters for detecting the emitted light in at least four emission wavelength ranges.

19. The apparatus of claim 17, further comprising:
 a) opposing plates positioned to receive the chamber of the vessel between them; and
 b) a heating element coupled to at least one of the plates.

20. The apparatus of claim 17, further comprising:
 a) a first housing for holding the light sources and the first set of filters, wherein the light sources and the first set of filters are rigidly fixed in the first housing; and
 b) a second housing for holding the detectors and the second set of filters, wherein the detectors and the second set of filters are rigidly fixed in the second housing.

21. The apparatus of claim 20, wherein the first housing has at least one optical window through which the excitation beams are transmitted, and wherein the apparatus further comprises a lens positioned in the optical window for focusing the excitation beams.

22. The apparatus of claim 20, wherein the second housing has at least one optical window through which the light emitted from the chamber is received, and wherein the apparatus further comprises a lens positioned in the optical window for collimating the light emitted from the chamber.

23. The apparatus of claim 17, further comprising a controller for controlling the operation of the light sources and detectors.

24. The apparatus of claim 23, wherein the controller is programmed to use a calibration matrix to convert output signals from the detectors into values representative of the concentrations of dyes labeling analytes in the reaction mixture.

25. The apparatus of claim 23, wherein at least one of the excitation wavelength ranges overlaps one of the emission wavelength ranges, and wherein the controller is programmed to receive a calibration signal from the detector receiving light in the overlapped emission wavelength range and to adjust subsequent output signals received from the detectors in dependence upon the calibration signal.

26. The apparatus of claim 17, wherein the first and second optically transmissive walls are angularly offset from each other by about 90°, and wherein the light sources, filters, and detectors are positioned to provide about a 90° angle between the path of each excitation beam entering the vessel through the first optically transmissive wall and the path of the emitted light detected through the second optically transmissive wall.

27. The apparatus of claim 17, wherein the thickness of the chamber is less than 5 mm, and wherein the ratio of the width of the chamber to the thickness of the chamber is at least 2:1.

28. An apparatus for optically interrogating a reaction mixture contained in a reaction vessel having a chamber for holding the mixture, the apparatus comprising:
 a) a first optics assembly comprising:
  i) a first housing having at least a first optical window;
  ii) a first light source rigidly fixed in the first housing for transmitting a first excitation beam to the chamber through the first optical window;
  iii) a first detector rigidly fixed in the first housing for detecting light emitted from the chamber; and
  iv) a first set of filters rigidly fixed in the first housing for filtering portions of the first excitation beam that are outside of a first excitation wavelength range, for filtering portions of the emitted light that are outside of a first emission wavelength range, and for directing the light in the first emission wavelength range to the first detector; and b) a second optics assembly comprising:
 i) a second housing having at least a second optical window;
 ii) a second light source rigidly fixed in the second housing for transmitting a second excitation beam to the chamber through the second optical window;
 iii) a second detector rigidly fixed in the second housing for detecting light emitted from the chamber; and
 iv) a second set of filters rigidly fixed in the second housing for filtering portions of the second excitation beam that are outside of a second excitation wavelength range different than the first excitation wavelength range, for filtering portions of the emitted light that are outside of a second emission wavelength range different than the first emission wavelength range, and for directing the light in the second emission wavelength range to the second detector.

29. The apparatus of claim 28, wherein the first optics assembly further includes a third detector rigidly fixed in the first housing, and wherein the first set of filters includes at least one filter for filtering portions of the emitted light that are outside of a third emission wavelength range different than the first and second emission wavelength ranges and for directing the light in the third emission wavelength range to the third detector.

30. The apparatus of claim 29, wherein the second optics assembly further includes a fourth detector rigidly fixed in the second housing, and wherein the second set of filters includes at least one filter for filtering portions of the emitted light that are outside of a fourth emission wavelength range different than the first, second, and third emission wavelength ranges and for directing the light in the fourth emission wavelength range to the fourth detector.

31. The apparatus of claim 28, wherein the vessel has at least first and second optically transmissive walls defining the chamber, the first and second optically transmissive walls are angularly offset from each other by about 90°, and the optics assemblies are positioned to provide about a 90° angle between the path of the first excitation beam entering the chamber through the first optically transmissive wall and the path of the emitted light detected through the second optically transmissive wall and to provide about a 90° angle between the path of the second excitation beam entering the chamber through the second optically transmissive wall and the path of the emitted light detected through the first optically transmissive wall.

32. The apparatus of claim 28, wherein the vessel includes at least first and second optically transmissive walls defining the chamber, the apparatus includes a slot for receiving the chamber of the vessel, and the first and second optics assemblies are positioned such that when the vessel is placed in the slot, the first and second optics assemblies are in optical communication with the first and second walls, respectively.

33. The apparatus of claim 32, wherein the first optics assembly further comprises a first lens positioned in the first optical window for focusing the first excitation beam and for collimating light emitted from the chamber through the first wall, and wherein the second optics assembly further comprises a second lens positioned in the second optical window for focusing the second excitation beam and for collimating light emitted from the chamber through the second wall.

34. The apparatus of claim 32, further comprising:
a) opposing plates defining the slot between them; and
b) a heating element coupled to at least one of the plates.

35. The apparatus of claim 34, wherein the plates, heating element, and optics assemblies are incorporated into a heat-exchanging module, the apparatus further comprises a base instrument for receiving the heat-exchanging module, and the base instrument includes electronics for controlling the operation of the module.

36. The apparatus of claim 35, wherein the heat-exchanging module further comprises a housing and a cooling device disposed within the housing for cooling the reaction mixture contained in the chamber.

37. The apparatus of claim 35, wherein the base instrument is constructed to receive and control a plurality of such heat-exchanging modules.

38. The apparatus of claim 37, further comprising at least one computer for controlling the base instrument.

39. An apparatus for optically interrogating a reaction mixture, the apparatus comprising:
a) a reaction vessel having a chamber for holding the mixture, wherein the vessel includes at least first and second optically transmissive walls defining the chamber;
b) a first light source for transmitting a first excitation beam to the mixture through the first wall;
c) a first detector for detecting light emitted from the chamber through the first wall;
d) a first set of filters for filtering portions of the first excitation beam that are outside of a first excitation wavelength range, for filtering portions of the light emitted through the first wall that are outside of a first emission wavelength range, and for directing the light in the first emission wavelength range to the first detector;
e) a second light source for transmitting a second excitation beam to the mixture through the second wall;
f) a second detector for detecting light emitted from the chamber through the second wall; and
g) a second set of filters for filtering portions of the second excitation beam that are outside of a second excitation wavelength range different than the first excitation wavelength range, for filtering portions of the light emitted through the second wall that are outside of a second emission wavelength range different than the first emission wavelength range, and for directing the light in the second emission wavelength range to the second detector.

40. The apparatus of claim 39, further comprising a third detector for detecting light emitted from the chamber through the first wall, wherein the first set of filters includes at least one filter for filtering portions of the light emitted through the first wall that are outside of a third emission wavelength range different than the first and second emission wavelength ranges and for directing the emitted light in the third emission wavelength range to the third detector.

41. The apparatus of claim 40, further comprising a fourth detector for detecting light emitted from the chamber through the second wall, wherein the second set of filters includes at least one filter for filtering portions of the light emitted through the second wall that are outside of a fourth emission wavelength range different than the first, second, and third emission wavelength ranges and for directing the light in the fourth emission wavelength range to the fourth detector.

42. The apparatus of claim 39, wherein the first and second optically transmissive walls of the vessel are angularly offset from each other by about 90°, and wherein the light sources, filters, and detectors are positioned to provide about a 90° angle between the path of the first excitation beam entering the vessel through the first optically transmissive wall and the path of the emitted light detected through the second optically transmissive wall and to provide about a 90° angle between the path of the second excitation beam entering the vessel through the second optically transmissive wall and the path of the emitted light detected through the first optically transmissive wall.

43. The apparatus of claim 39, further comprising:
   a) opposing plates positioned to receive the chamber of the vessel between them; and
   b) a heating element coupled to at least one of the plates.

44. The apparatus of claim 39, further comprising:
   a) a first housing for holding the first light source, the first detector, and the first set of filters, wherein the first light source, the first detector, and the first set of filters are rigidly fixed in the first housing; and
   b) a second housing for holding the second light source, the second detector, and the second set of filters, wherein the second light source, the second detector, and the second set of filters are rigidly fixed in the second housing.

45. The apparatus of claim 44, wherein the first housing has at least one optical window through which the first excitation beam is transmitted and through which light emitted from the chamber through the first wall is received, and wherein the apparatus further comprises a lens positioned in the optical window.

46. The apparatus of claim 44, wherein the second housing has at least one optical window through which the second excitation beam is transmitted and through which light emitted from the chamber through the second wall is received, and wherein the apparatus further comprises a lens positioned in the optical window.

47. The apparatus of claim 39, further comprising a controller for controlling the operation of the light sources and detectors.

48. The apparatus of claim 39, wherein the thickness of the chamber is less than 5 mm, and wherein the ratio of the width of the chamber to the thickness of the chamber is at least 2:1.

49. An apparatus for thermally controlling and optically interrogating a reaction mixture contained in a reaction vessel, wherein the vessel has a chamber for holding the mixture, the apparatus comprising:
   a) at least one thermal surface for contacting a wall of the chamber;
   b) a heating element for heating the thermal surface; and
   c) first and second optics assemblies for optically interrogating the reaction mixture in the chamber;
   the first optics assembly comprising:
      i) a first housing having at least one optical window;
      ii) at least two light sources rigidly fixed in the first housing for transmitting excitation beams to the reaction mixture through the at least one optical window; and
      iii) a first set of filters rigidly fixed in the first housing for filtering the excitation beams such that each of the beams transmitted to the reaction mixture has a substantially distinct excitation wavelength range;
   and the second optics assembly comprising:
      i) a second housing having at least one optical window for receiving light emitted from the chamber;
      ii) at least two detectors rigidly fixed in the second housing for detecting the emitted light in at least two respective emission wavelength ranges; and
      iii) a second set of filters rigidly fixed in the second housing for separating the emitted light into the respective emission wavelength ranges.

50. The apparatus of claim 49, wherein the apparatus includes first and second thermal surfaces for contacting the vessel, and wherein the thermal surfaces are provided by opposing plates positioned to receive the chamber of the vessel between them.

51. The apparatus of claim 50, wherein the first and second optics assemblies are positioned such that when the vessel is inserted between the plates, each of the optics assemblies is in optical communication with the chamber through at least one optically transmissive wall of the vessel.

52. An apparatus for thermally controlling and optically interrogating a reaction mixture contained in a reaction vessel, wherein the vessel has a chamber for holding the mixture, the apparatus comprising:
   a) at least one thermal surface for contacting a wall of the chamber;
   b) a heating element for heating the thermal surface; and
   c) first and second optics assemblies for optically interrogating the reaction mixture in the chamber;
   the first optics assembly comprising:
      i) a first housing having a first optical window;
      ii) a first light source rigidly fixed in the first housing for transmitting a first excitation beam to the reaction mixture through the first window;
      iii) a first detector rigidly fixed in the first housing for receiving through the first window light emitted from the chamber; and
      iv) a first set of filters rigidly fixed in the first housing for filtering portions of the first excitation beam that are outside of a first excitation wavelength range, for filtering portions of the light received through the first window that are outside of a first emission wavelength range, and for directing the light in the first emission wavelength range to the first detector;
   and the second optics assembly comprising:
      i) a second housing having a second optical window;
      ii) a second light source rigidly fixed in the second housing for transmitting a second excitation beam to the reaction mixture through the window;
      iii) a second detector rigidly fixed in the second housing for receiving through the second window light emitted from the chamber; and
      iv) a second set of filters rigidly fixed in the second housing for filtering portions of the second excitation beam that are outside of a second excitation wavelength range different than the first excitation wavelength range, for filtering portions of the light received through the second window that are outside of a second emission wavelength range different than the first emission wavelength range, and for directing the light in the second emission wavelength range to the second detector.

53. The apparatus of claim 52, wherein the apparatus includes first and second thermal surfaces for contacting the vessel, and wherein the thermal surfaces are provided by opposing plates positioned to receive the chamber of the vessel between them.

54. The apparatus of claim 53, wherein the first and second optics assemblies are positioned such that when the vessel is inserted between the plates, each of the optics assemblies is in optical communication with the chamber through at least one optically transmissive wall of the vessel.

* * * * *

UNITED STATES PATENT AND TRADEMARK OFFICE
CERTIFICATE OF CORRECTION

PATENT NO.   : 6,369,893 B1                                Page 1 of 1
DATED        : April 9, 2002
INVENTOR(S)  : Christel et al.

It is certified that error appears in the above-identified patent and that said Letters Patent is hereby corrected as shown below:

<u>Title page,</u>
Item [63], Related U.S. Application Data, change
"Continuation-in-part of application No. 09/081,260, filed on May 19, 1998, now abandoned, and a continuation-in-part of application No. 09/194,374, filed on Jul. 25, 2000." to -- Continuation-in-part of application No. 09/081,260, filed on May 19, 1998, now abandoned, and a continuation-in-part of application No. 09/194,374, filed on Nov. 24, 1998, pending. --

Signed and Sealed this

Twenty-ninth Day of July, 2003

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,369,893 B1 | Page 1 of 1 |
| APPLICATION NO. | : 09/314605 | |
| DATED | : April 9, 2002 | |
| INVENTOR(S) | : Christel et al. | |

It is certified that error appears in the above-identified patent and that said Letters Patent is hereby corrected as shown below:

Please delete paragraph at column 1, lines 5 – 10 and replace with:

-- This application is a continuation-in-part of U.S. Ser. No. 09/081,260 filed May 19, 1998, abandoned, and a continuation-in-part of U.S. Ser. No. 09/194,374 filed November 24, 1998, pending, the disclosures of both of which are incorporated by reference herein. --

Signed and Sealed this

Fifth Day of June, 2007

JON W. DUDAS
*Director of the United States Patent and Trademark Office*